United States Patent
Embrey et al.

(10) Patent No.: US 11,413,292 B2
(45) Date of Patent: Aug. 16, 2022

(54) TRICYCLIC HETEROCYCLE COMPOUNDS USEFUL AS HIV INTEGRASE INHIBITORS

(71) Applicant: Merck Sharp & Dohme Corp., Rahway, NJ (US)

(72) Inventors: Mark W. Embrey, Harleysville, PA (US); Timothy John Hartingh, Richlandtown, PA (US); Marc Labroli, Moorestown, NJ (US); Izzat T. Raheem, Doylestown, PA (US)

(73) Assignee: Merck, Sharp & Dohme LLC, Rahway, NJ (US)

( * ) Notice: Subject to any disclaimer, the term of this patent is extended or adjusted under 35 U.S.C. 154(b) by 95 days.

(21) Appl. No.: 16/966,961

(22) PCT Filed: Feb. 11, 2019

(86) PCT No.: PCT/US2019/017409
§ 371 (c)(1),
(2) Date: Aug. 3, 2020

(87) PCT Pub. No.: WO2019/160783
PCT Pub. Date: Aug. 22, 2019

(65) Prior Publication Data
US 2021/0361662 A1 Nov. 25, 2021

Related U.S. Application Data

(60) Provisional application No. 62/630,974, filed on Feb. 15, 2018.

(51) Int. Cl.
| | | |
|---|---|---|
| *A61K 31/53* | (2006.01) | |
| *A61K 31/427* | (2006.01) | |
| *A61K 31/4418* | (2006.01) | |
| *A61K 31/505* | (2006.01) | |
| *A61K 31/513* | (2006.01) | |
| *A61K 31/52* | (2006.01) | |
| *A61K 31/5365* | (2006.01) | |
| *A61K 31/635* | (2006.01) | |
| *A61K 31/675* | (2006.01) | |
| *A61K 31/7068* | (2006.01) | |
| *C07D 471/18* | (2006.01) | |
| *C07D 498/18* | (2006.01) | |

(52) U.S. Cl.
CPC ............ *A61K 31/53* (2013.01); *A61K 31/427* (2013.01); *A61K 31/4418* (2013.01); *A61K 31/505* (2013.01); *A61K 31/513* (2013.01); *A61K 31/52* (2013.01); *A61K 31/5365* (2013.01); *A61K 31/635* (2013.01); *A61K 31/675* (2013.01); *A61K 31/7068* (2013.01); *C07D 471/18* (2013.01); *C07D 498/18* (2013.01)

(58) Field of Classification Search
CPC .................................................... A61K 31/53
USPC ......................................................... 514/243
See application file for complete search history.

(56) References Cited

U.S. PATENT DOCUMENTS

| | | | |
|---|---|---|---|
| 8,188,271 B2* | 5/2012 | Yoshida ............... | C07D 498/14 544/183 |
| 2012/0208998 A1 | 8/2012 | Yoshida et al. | |
| 2015/0329539 A1 | 11/2015 | Embrey et al. | |
| 2016/0317543 A1 | 11/2016 | Graham et al. | |
| 2017/0305923 A1 | 10/2017 | Embrey et al. | |
| 2017/0334924 A1 | 11/2017 | Embrey et al. | |
| 2017/0362252 A1 | 12/2017 | Graham et al. | |
| 2018/0051043 A1 | 2/2018 | Yu et al. | |
| 2018/0194774 A1 | 7/2018 | Yu et al. | |
| 2018/0325926 A1 | 11/2018 | Graham et al. | |
| 2018/0325927 A1 | 11/2018 | Graham et al. | |
| 2019/0040076 A1 | 2/2019 | Zhang et al. | |

FOREIGN PATENT DOCUMENTS

| | | |
|---|---|---|
| WO | 2009154870 A1 | 12/2009 |
| WO | 2015039348 A1 | 3/2015 |
| WO | 2015048363 A1 | 4/2015 |

OTHER PUBLICATIONS

Pearl, L.H., et al.,, "A Structural Model for the Retroviral Proteases", NATURE, 1987, pp. 351-354, vol. 329.
Power, M.D., et al.,, "Nucleotide Sequence of SRV-1, a Type D Simian", SCIENCE, 1986, pp. 1567-1572, vol. 231.
Ratner, L., et al.,, "Complete Nucleotide Sequence of AIDS Virus, HTLV-III", NATURE, 1985, pp. 277-284, vol. 313.
European search report, Application No. 19754182.4, 5 pages.

* cited by examiner

*Primary Examiner* — Nizal S Chandrakumar
(74) *Attorney, Agent, or Firm* — John C. Todaro

(57) ABSTRACT

The present invention relates to Tricyclic Heterocycle Compounds of Formula (I): and pharmaceutically acceptable salts or prodrug thereof, wherein X, Y, Z, $R^1$ and n are as defined herein. The present invention also relates to compositions comprising at least one Tricyclic Heterocycle Compound, and methods of using the Tricyclic Heterocycle Compounds for treating or preventing HIV infection in a subject.

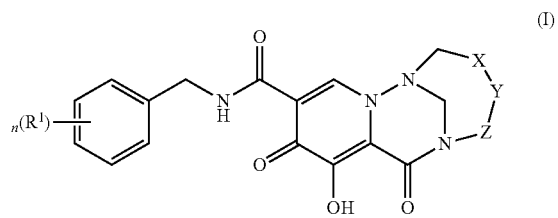

(I)

18 Claims, No Drawings

TRICYCLIC HETEROCYCLE COMPOUNDS USEFUL AS HIV INTEGRASE INHIBITORS

CROSS REFERENCE TO RELATED APPLICATIONS

This application is a U.S. National Phase application under 35 U.S.C. §371 of PCT Application No. PCT/US2019/017409 filed Feb. 11, 2019, which claims priority from U.S. Ser. No. 62/630,974 filed Feb. 15, 2018.

FIELD OF THE INVENTION

The present invention relates to Tricyclic Heterocycle Compounds, compositions comprising at least one Tricyclic Heterocycle Compound, and methods of using the Tricyclic Heterocycle Compounds for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA, and covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Rather, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication.

SUMMARY OF THE INVENTION

In one aspect, the present invention provides Compounds of Formula (I):

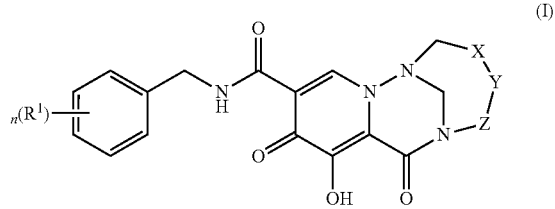

or a pharmaceutically acceptable salt thereof, wherein:

X is —$CR^2R^3$, —O— or —$NR^4$;
Y is —$CHR^4$—$CR^2R^3$, —$CR^2R^3$, —O— or —$NR^4$;
Z is —$CR^2R^3$—$CHR^4$, —$CR^2R^3$;
each occurrence of $R^1$ is independently selected from the group consisting of halo, hydroxyl, $C_{1-6}$ alkyl and —O—($C_1$-$C_6$ alkyl);
each occurrence of $R^2$ is independently selected from the group consisting of hydrogen, halo, hydroxyl, $C_{1-6}$ alkyl and —O—($C_1$-$C_6$ alkyl);
each occurrence of $R^3$ is independently selected from the group consisting of hydrogen, halo, hydroxyl, $C_{1-6}$ alkyl and —O—($C_1$-$C_6$ alkyl);
each occurrence of $R^4$ is independently selected from the group consisting of hydrogen or $C_{1-6}$ alkyl;
n is an integer between zero and three.

The Compounds of Formula (I) (also referred to herein as the "Tricyclic Heterocycle Compounds") and pharmaceutically acceptable salts or prodrugs thereof may be useful, for example, for inhibiting HIV viral replication or replicon activity, or for treating or preventing HIV infection in a subject. Without being bound by any specific theory, it is believed that the Tricyclic Heterocycle Compounds inhibit HIV viral replication by inhibiting HIV Integrase.

Accordingly, the present invention provides methods for treating or preventing HIV infection in a subject, comprising administering to the subject an effective amount of at least one Tricyclic Heterocycle Compound.

The details of the invention are set forth in the accompanying detailed description below.

Although any methods and materials similar to those described herein may be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes Tricyclic Heterocycle Compounds, compositions comprising at least one Tricyclic Heterocycle Compound, and methods of using the Tricyclic Heterocycle Compounds for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of Tricyclic Heterocycle Compound and/or an additional therapeutic agent, or a composition thereof that is effective in inhibiting HIV replication and in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The terms "treating" or "treatment" as used herein with respect to an HIV viral infection or AIDS, includes inhibiting the severity of HIV infection or AIDS a disease, i.e., arresting or reducing the development of the HIV infection or AIDS a disease or its clinical symptoms; or relieving the HIV infection or AIDS a disease, i.e., causing regression of the severity of HIV infection or AIDS a disease or its clinical symptoms.

The terms "preventing," or "prohylaxis," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., $R^2$ and $R^3$) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design,* (1987) Edward B. Roche, ed., American Pharmaceutical Association and Pergamon Press. The term "prodrug" means a compound (e.g., a drug precursor) that is transformed in vivo to provide a Tricyclic Heterocycle Compound or a pharmaceutically acceptable salt of the compound. The transformation may occur by various mechanisms (e.g., by metabolic or chemical processes), such as, for example, through hydrolysis in blood. For example, if a Tricyclic Heterocycle Compound or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as (3-dimethylaminoethyl), carbamoyl-($C_1$-$C_2$)alkyl, N,N-di ($C_1$-$C_2$) alkylcarbamoyl-($C_1$-$C_2$)alkyl and piperidino-, pyrrolidino- or morpholino($C_2$-$C_3$)alkyl, and the like.

Similarly, if a Tricyclic Heterocycle Compound contains an alcohol functional group, a prodrug can be formed by the replacement of one or more of the hydrogen atoms of the alcohol groups with a group such as, for example, ($C_1$-$C_6$) alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkyl, α-amino ($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a Tricyclic Heterocycle Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$)alkyl, ($C_3$-$C_7$) cycloalkyl, benzyl, a natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl; carboxy ($C_1$-$C_6$)alkyl; amino($C_1$-$C_4$)alkyl or mono-N- or di-N,N—($C_1$-$C_6$)alkylaminoalkyl; —C(Y$^4$)Y$^5$ wherein Y$^4$ is H or methyl and Y$^5$ is mono-N- or di-N,N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvates, hydrates and the like are described by E. C. van Tonder et al, *AAPS PharmSciTech.* 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Tricyclic Heterocycle Compounds can form salts which are also within the scope of this invention. Reference to a Tricyclic Heterocycle Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Tricyclic Heterocycle Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Tricyclic Heterocycle Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Tricyclic Heterocycle Compounds may be atropisomers (e.g., substituted biaryls) and are considered as part of this invention. Enantiomers can also be directly separated using chiral chromatographic techniques.

It is also possible that the Tricyclic Heterocycle Compounds may exist in different tautomeric forms, and all such forms are embraced within the scope of the invention. For example, all keto-enol and imine-enamine forms of the compounds are included in the invention.

Unless otherwise indicated, all stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Tricyclic Heterocycle Compound incorporates a double bond or a fused ring, both the cis- and trans-forms, as well as mixtures, are embraced within the scope of the invention.

When a substituent on a chiral carbon atom is depicted without stereospecificity (by using a straight line bond to a chiral center), it is to be understood that both the alpha and beta configurations of said substituent group are to be considered part of the present invention. For example, the compound of the present invention, which is drawn as follows:

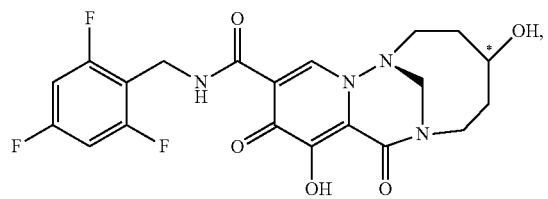

is understood to encompass both stereoisomers at the indicated chiral center, the structures of which are as follows:

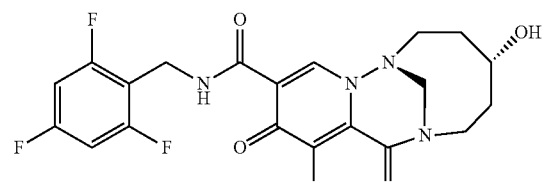

and

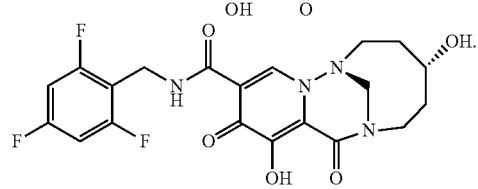

In the Examples section below, compounds of the present invention that have been purified as individual stereoisomers are sometimes depicted in non-stereospecific form but identified using one or more of the terms: "diastereomer 1," "diastereomer 2," "enantiomer A" and "enantiomer B." In this instance, the absolute stereochemistry of each isolated diastereomer and enantiomeric center has not been determined and the terms used above are used to represent each individual purified stereochemicacally pure compound.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may provide certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

The Tricyclic Heterocycle Compounds may be useful in human and veterinary medicine for treating or preventing HIV infection in a subject. In one embodiment, the Tricyclic Heterocycle Compounds can be inhibitors of HIV viral replication. In a specific embodiment, the Tricyclic Heterocycle Compounds are inhibitors of HIV-1. Accordingly, the Tricyclic Heterocycle Compounds may be useful for treating HIV infections and AIDS. In accordance with the invention, the Tricyclic Heterocycle Compounds can be administered to a subject in need of treatment or prevention of HIV infection.

Accordingly, in one embodiment, the invention provides methods for treating HIV infection in a subject comprising administering to the subject an effective amount of at least one Tricyclic Heterocycle Compound or a pharmaceutically acceptable salt thereof. In a specific embodiment, the present invention provides methods for treating AIDS in a subject comprising administering to the subject an effective amount of at least one Tricyclic Heterocycle Compound or a pharmaceutically acceptable salt thereof.

The Compounds of Formula (I)

The present invention provides Tricyclic Heterocycle Compounds of Formula (I):

$$\text{(I)}$$

and pharmaceutically acceptable salts thereof, wherein:

X is —$CR^2R^3$, —O— or —$NR^4$;
Y is —$CHR^4$—$CR^2R^3$, —$CR^2R^3$, —O— or —$NR^4$;
Z is —$CR^2R^3$—$CHR^4$, —$CR^2R^3$;
each occurrence of $R^1$ is independently selected from the group consisting of halo, hydroxyl, $C_{1-6}$ alkyl and —O—($C_1$-$C_6$ alkyl);
each occurrence of $R^2$ is independently selected from the group consisting of hydrogen, halo, hydroxyl, $C_{1-6}$ alkyl and —O—($C_1$-$C_6$ alkyl);
each occurrence of $R^3$ is independently selected from the group consisting of hydrogen, halo, hydroxyl, $C_{1-6}$ alkyl and —O—($C_1$-$C_6$ alkyl);
each occurrence of $R^4$ is independently selected from the group consisting of hydrogen or $C_{1-6}$ alkyl;
n is an integer between zero and three.

In an embodiment of the invention, X is —$CR^2R^3$. In a class of the embodiment, X is $CH_2$.

In an embodiment of the invention, Y is —$CHR^4$—$CR^2R^3$. In a class of the embodiment, Y is —$CH_2CH_2$. In another embodiment, Y is —$CR^2R^3$. In a class of the embodiment, Y is —$CHOCH_3$. In another class of the embodiment, Y is —$CHOH$. In another class of the embodiment, Y is —$CH_2$. In another class of the embodiment, Y is —$CF_2$. In another embodiment, Y is —O—. In another embodiment, Y is —$NR^4$. In a class of the embodiment, Y is —$NCH_3$.

In an embodiment of the invention, Z is —$CR^2R^3$—$CHR^4$. In a class of the embodiment, Z is —$CH_2CH_2$. In another embodiment, Z is —$CR^2R^3$. In a class of the embodiment, Z is —$CH_2$.

In an embodiment of the invention, each occurrence of $R^1$ is halo.

In an embodiment of the invention, each occurrence of $R^2$ is independently selected from the group consisting of hydrogen, halo, hydroxyl, and —$OCH_3$.

In an embodiment of the invention, $R^4$ is hydrogen or methyl.

In an embodiment of the invention, n is two. In another embodiment, n is three.

In one embodiment, variables X, Y, Z, $R^1$ and n for the Compounds of Formula (I) are selected independently of each other.

In another embodiment, the Compounds of Formula (I) are in substantially purified form.

It is to be understood that any of the aforementioned embodiments may be combined with one or more separate embodiments.

Other embodiments of the present invention include the following:

(a) A pharmaceutical composition comprising an effective amount of a Compound of Formula (I), and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors and HIV NNRTI inhibitors.

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors and HIV NNRTI inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors and HIV NNRTI inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

Additional embodiments of the present invention include the following:

(l) A pharmaceutical composition comprising an effective amount of a pharmaceutically acceptable salt of a Compound of Formula (I), and a pharmaceutically acceptable carrier.

(m) The pharmaceutical composition of (l), further comprising a second therapeutic agent selected from the group consisting of HIV antiviral agents, immunomodulators, and anti-infective agents.

(n) The pharmaceutical composition of (m), wherein the HIV antiviral agent is an antiviral selected from the group consisting of HIV protease inhibitors and HIV NNRTI inhibitors.

(o) A pharmaceutical combination that is (i) a pharmaceutically acceptable salt of a Compound of Formula (I) and (ii) a second therapeutic agent selected from the group consisting of HIV antiviral agents, immunomodulators, and anti-infective agents; wherein the pharmaceutically acceptable salt of the Compound of Formula (I) and the second therapeutic agent are each employed in an amount that renders the combination effective for inhibiting HIV replication, or for treating HIV infection and/or reducing the likelihood or severity of symptoms of HIV infection.

(p) The combination of (o), wherein the HIV antiviral agent is an antiviral selected from the group consisting of HIV protease inhibitors and HIV NNRTI inhibitors.

(q) A method of inhibiting HIV replication in a subject in need thereof which comprises administering to the subject an effective amount of a pharmaceutically acceptable salt of a Compound of Formula (I).

(r) A method of treating HIV infection and/or reducing the likelihood or severity of symptoms of HIV infection in a subject in need thereof which comprises administering to the subject an effective amount of a pharmaceutically acceptable salt of a Compound of Formula (I).

(s) The method of (r), wherein the pharmaceutically acceptable salt of the Compound of Formula (I) is administered in combination with an effective amount of at least one second therapeutic agent selected from the group consisting of HIV antiviral agents, immunomodulators, and anti-infective agents.

(t) The method of (s), wherein the HIV antiviral agent is an antiviral selected from the group consisting of HIV protease inhibitors and HIV NS5B polymerase inhibitors.

(u) A method of inhibiting HIV replication in a subject in need thereof which comprises administering to the subject the pharmaceutical composition of (1), (m) or (n) or the combination of (o) or (p).

(v) A method of treating HIV infection and/or reducing the likelihood or severity of symptoms of HIV infection in a subject in need thereof which comprises administering to the subject the pharmaceutical composition of (1), (m) or (n) or the combination of (o) or (p).

Further embodiments of the present invention include the following:

(w) A pharmaceutical composition comprising an effective amount of a Compound of Formula (I) or a pharmaceutically acceptable salt thereof, and a pharmaceutically acceptable carrier.

(x) The pharmaceutical composition of (w), further comprising a second therapeutic agent selected from the group consisting of HIV antiviral agents, immunomodulators, and anti-infective agents.

(y) The pharmaceutical composition of (x), wherein the HIV antiviral agent is an antiviral selected from the group consisting of HIV protease inhibitors and HIV NNRTI inhibitors.

(z) A pharmaceutical combination that is (i) a Compound of Formula (I) and (ii) or a pharmaceutically acceptable salt thereof, a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(aa) The combination of (z), wherein the HIV antiviral agent is an antiviral selected from the group consisting of HIV protease inhibitors and HIV NNRTI inhibitors.

(bb) A method of inhibiting HIV replication in a subject in need thereof which comprises administering to the subject an effective amount of a Compound of Formula (I) or a pharmaceutically acceptable salt thereof.

(cc) A method of treating HIV infection and/or reducing the likelihood or severity of symptoms of HIV infection in a subject in need thereof which comprises administering to the subject an effective amount of a Compound of Formula (I) or a pharmaceutically acceptable salt thereof.

(dd) The method of (cc), wherein the Compound of Formula (I) or pharmaceutically acceptable salt thereof, is administered in combination with an effective amount of at least one second therapeutic agent selected from the group consisting of HIV antiviral agents, immunomodulators, and anti-infective agents.

(ee) The method of (dd), wherein the HIV antiviral agent is an antiviral selected from the group consisting of HIV protease inhibitors and HIV NNRTI inhibitors.

(ff) A method of inhibiting HIV replication in a subject in need thereof which comprises administering to the subject the pharmaceutical composition of (w) (x) or (y) or the combination of (z) or (aa).

(gg) A method of treating HIV infection and/or reducing the likelihood or severity of symptoms of HIV infection in a subject in need thereof which comprises administering to the subject the pharmaceutical composition of (w) (x) or (y) or the combination of (z) or (aa).

The present invention also includes a compound of the present invention for use (i) in, (ii) as a medicament for, or (iii) in the preparation of a medicament for: (a) medicine; (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(gg) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (gg) above are understood to include all embodiments of the compounds, including such embodiments as result from combinations of embodiments.

Non-limiting examples of the Compounds of Formula (I) include compounds 1A-18B as set forth in the Examples below, and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in the Schemes below. Alternative synthetic pathways and analogous structures will be apparent to those skilled in the art of organic synthesis.

General List of Abbreviations

Abbreviations and acronyms employed herein include the following:

| | |
|---|---|
| Ac | Acetyl |
| aq | Aqueous |
| AUC | Area under the curve |
| BAST | Bis(2-methoxyethyl)aminosulfur trifluoride |
| Bu | Butyl |
| Bz | Benzoyl |
| DBDMH | 1,3-Dibromo-5,5-dimethylhydantoin |
| DCM | dichloromethane |
| DHP | 3,4-dihydro-2H-pyran |
| DIEA, DIPEA or Hünig's base | N,N-diisopropylethylamine |
| DMF | dimethylformamide |
| DMP | Dess-Martin periodinane |
| dppf | 1,1'-Bis(diphenylphosphino)ferrocene |
| DMSO | dimethyl sulfoxide |
| EDCI | N-ethyl-N'-(3-dimethylaminopropyl)carbodiimide hydrochloride |
| Et | Ethyl |
| EtOH | Ethanol |
| EtOAc | ethyl acetate |
| g | Grams |
| GI | gastrointenstinal |
| h | Hour |
| HIV | human immunodeficiency virus |
| HPBCD | hydroxypropyl β-cyclodextrin |
| HPLC | high-performance liquid chromatography |
| HOBT | |
| mCPBA | |
| Hz | hertz |
| IPA | isopropanol |
| IV | intravenous |
| iPr | isopropyl |
| L | liter |
| LC | liquid chromatography |
| LC/MS | liquid chromatography mass spectrometry |
| Me | methyl |
| MeOH | methanol |
| mg | milligrams |
| MHz | megahertz |
| min | minute |
| μL | microliters |
| mL | milliliters |
| mmol | millimoles |
| MS | mass spectrometry |
| NBS | N-Bromosuccinimide |
| NHS | normal human serum |
| NIS | N-Iodosuccinimide |
| NMR | nuclear magnetic resonance spectroscopy |
| PBMC | peripheral blood mononuclear cell |
| Ph | phenyl |
| P.O. | oral |
| PTSA | para-toluenesulfonic acid |
| Pr | propyl |
| RT or rt | room temperature (ambient, about 25° C.) |
| sat or sat'd | saturated |
| SFC | supercritical fluid chromatography |
| TBAF | Tetra-n-butylammonium fluoride |
| TBDPSCl | tert-Butyldiphenylchlorosilane |
| tBu | tert-butyl |
| TEA | triethylamine ($Et_3N$) |
| TEMED | tetramethylethylenediamine |
| TFA | trifluoroacetic acid |
| TFV | Tenofovir |
| TFV-MP | Tenofovir monophosphoate |
| TFV-DP | Tenofovir diphosphate |
| THF | tetrahydrofuran |
| TMS | tetramethylsilane |
| UPLC | ultrahigh pressure liquid chromatography |
| UV | ultraviolet |
| UV/VIS | ultraviolet/visible |

General Procedures

Starting materials and intermediates are purchased or are made using known procedures, or as otherwise illustrated. The general route applied to the synthesis of compounds of Formula I is described in the Schemes that follows. In some cases the order of carrying out the reaction steps in the schemes may be varied to facilitate the reaction or to avoid unwanted reaction products.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60E-254, layer thickness 0.25 mm or liquid chromatography-mass spectrometry (LC/MS).

Typically the analytical LC-MS system used consisted of a Waters ZQ™ platform with electrospray ionization in positive ion detection mode with an Agilent 1100 series HPLC with autosampler. The column was commonly a Waters Xterra MS C18, 3.0×50 mm, 5 μm or a Waters Acquity UPLC® BEH C18 1.0×50 mm, 1.7 μm. The flow rate was 1 mL/min, and the injection volume was 10 μL. UV detection was in the range 210-400 nm. The mobile phase consisted of solvent A (water plus 0.05% TFA) and solvent B (MeCN plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using either a mass spectrometry directed system or a non-mass guided system. Usually they were performed on a Waters Chromatography Workstation configured with LC-MS System consisting of: Waters ZQ™ single quad MS system with Electrospray Ionization, Waters 2525 Gradient Pump, Waters 2767 Injecto/Collector, Waters 996 PDA Detector, the MS Conditions of: 150-750 amu, Positive Electrospray, Collection Triggered by MS, and a Waters SUNFIRE® C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 μL, and the UV detection range was 210-400 nm. An alternate preparative HPLC system used was a Gilson Workstation consisting of: Gilson GX-281 Injector/Collector, Gilson UV/VIS-155 Detector, Gilson 333 and 334 Pumps, and either a Phenomenex Gemini-NX C-18 5 micron, 50 mm (id)×250 mm column or a Waters XBridge™ C-18 5 micron OBD™, 30 mm (id)×250 mm column. The mobile phases consisted of mixtures of acetonitrile (0-85%) in water containing 0.1% TFA. Flow rates were maintained at 50 mL/min for the Waters Xbridge™ column and 90 mL/min for the Phenomenex Gemini column. The injection volume ranged from 1000-8000 μL, and the UV detection range was 210-400 nm. Mobile phase gradients were optimized for the individual compounds. Reactions performed using microwave irradiation were normally carried out using an Emrys Optimizer manufactured by Personal Chemistry, or an Initiator manufactured by Biotage. Concentration of solutions was carried out on a rotary evaporator under reduced pressure. Flash chromatography was usually performed using either a Biotage® Flash Chromatography apparatus (Dyax Corp.), an ISCO CombiFlash® Rf apparatus, or an ISCO CombiFlash® Companion XL on silica gel (32-63 microns, 60 Å pore size) in pre-packed cartridges of the size noted. $^1$H NMR spectra were acquired at 500 MHz spectrometers in $CDCl_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz). Chiral analytical chromatography was most commonly performed on one of CHIRALPAK® AS, CHIRALPAK®AD, CHIRALCEL® OD, CHIRALCEL® IA, or CHIRALCEL® OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of CHIRALPAK AS, of CHIRALPAK AD, CHIRALCEL® OD, CHIRALCEL®IA, CHIRALCEL® OJ columns (20×250 mm) (Daicel Chemical Industries, Ltd.) with desired isocratic solvent systems identified on chiral analytical chromatography or by supercritical fluid (SFC) conditions.

Several methods for preparing the compounds of this invention are also described in the Examples. Starting materials and intermediates were purchased commercially from common catalog sources or were made using known procedures, or as otherwise illustrated.

Preparation of Intermediate A

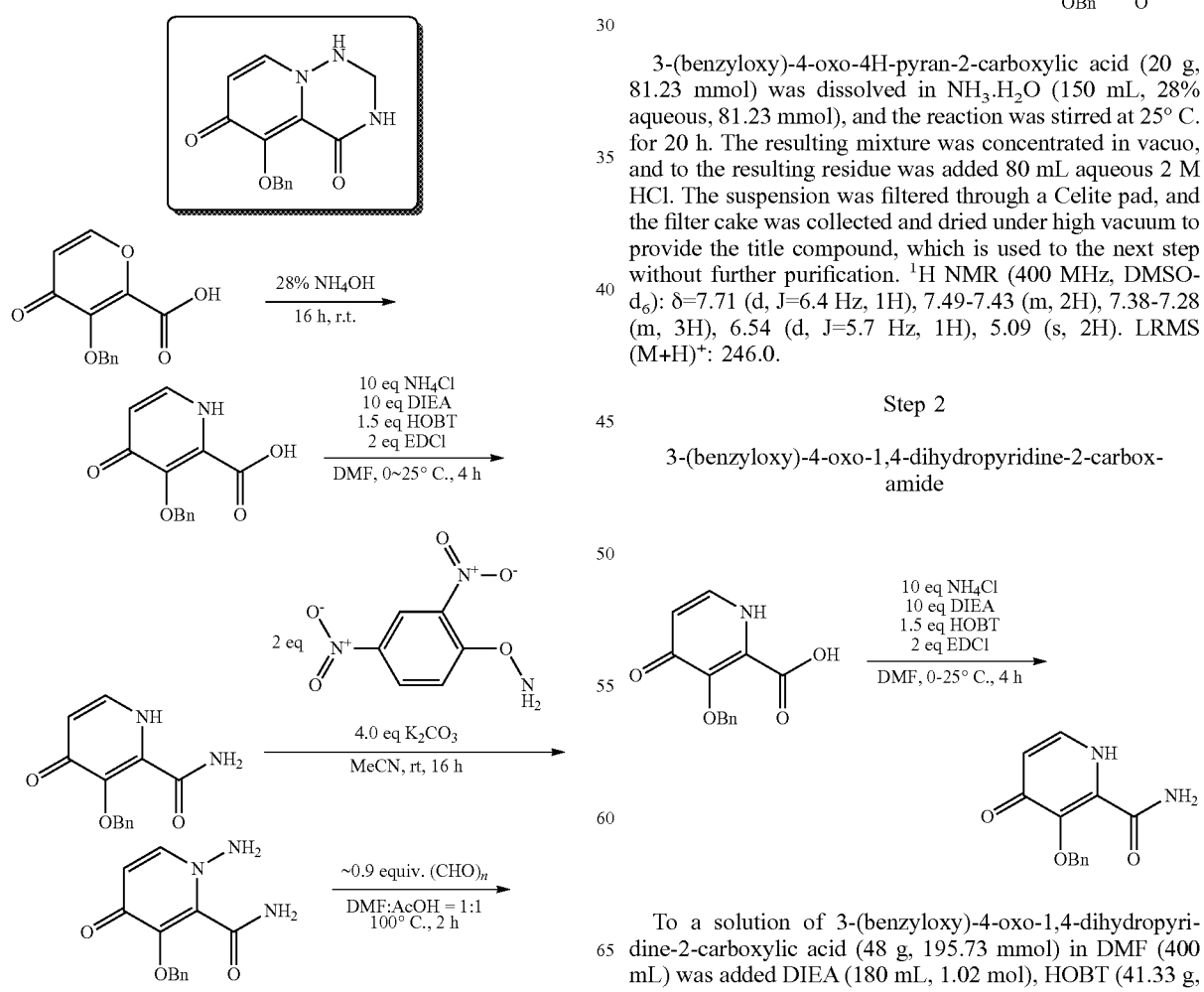

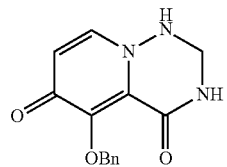

INTERMEDIATE A

Step 1

3-(benzyloxy)-4-oxo-1,4-dihydropyridine-2-carboxylic acid

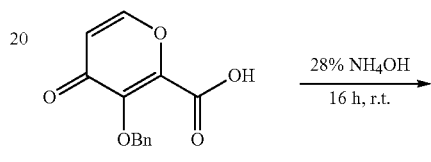

3-(benzyloxy)-4-oxo-4H-pyran-2-carboxylic acid (20 g, 81.23 mmol) was dissolved in NH$_3$.H$_2$O (150 mL, 28% aqueous, 81.23 mmol), and the reaction was stirred at 25° C. for 20 h. The resulting mixture was concentrated in vacuo, and to the resulting residue was added 80 mL aqueous 2 M HCl. The suspension was filtered through a Celite pad, and the filter cake was collected and dried under high vacuum to provide the title compound, which is used to the next step without further purification. $^1$H NMR (400 MHz, DMSO-d$_6$): δ=7.71 (d, J=6.4 Hz, 1H), 7.49-7.43 (m, 2H), 7.38-7.28 (m, 3H), 6.54 (d, J=5.7 Hz, 1H), 5.09 (s, 2H). LRMS (M+H)$^+$: 246.0.

Step 2

3-(benzyloxy)-4-oxo-1,4-dihydropyridine-2-carboxamide

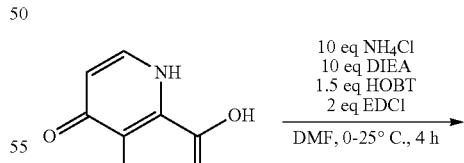

To a solution of 3-(benzyloxy)-4-oxo-1,4-dihydropyridine-2-carboxylic acid (48 g, 195.73 mmol) in DMF (400 mL) was added DIEA (180 mL, 1.02 mol), HOBT (41.33 g, 305.83 mmol), and EDC (78.17 g, 407.78 mmol) at 0° C.

The reaction mixture was stirred at 25° C. for 1 h, then solid NH₄Cl (54.53 g, 1.02 mol) was added in portions, and the reaction mixture was stirred at 25° C. for 3 h. The resulting mixture was filtered and the filtrate was concentrated in vacuo. The resulting residue was purified by preparative HPLC (Column: Phenomenex Synergi Max-RP 150*50 mm*10 μm; Conditions: water (0.1% TFA)/MeCN; begin B 0%, end B 30%; gradient time 20 min; 100% B hold time 5 min, flowrate 120 mL/min) to provide the title compound. ¹H NMR (400 MHz, CD₃OD): δ=7.91 (d, J=6.6 Hz, 1H), 7.47-7.41 (m, 2H), 7.35 (m, 3H), 6.88 (d, J=6.6 Hz, 1H), 5.47 (s, 2H). LRMS (M+H)⁺: 245.0.⁺

Step 3

1-amino-3-(benzyloxy)-4-oxo-1,4-dihydropyridine-2-carboxamide

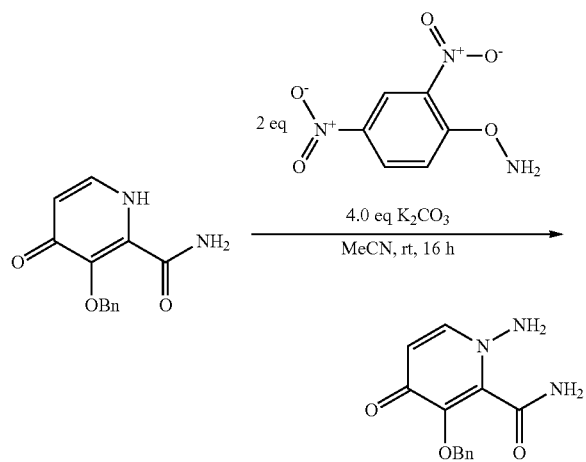

A mixture of 3-(benzyloxy)-4-oxo-1,4-dihydropyridine-2-carboxamide (1.5 g, 6.14 mmol) and K₂CO₃ (3.39 g, 24.56 mmol) in MeCN (30 mL) was cooled to 0° C. O-(2,4-dinitrophenyl)-hydroxylamine (2.45 g, 12.28 mmol) was then added as a solid in portions. The mixture was stirred at 28° C. for 16 h, and the resulting mixture was concentrated in vacuo directly. The resulting crude product was purified by gradient elutions on SiO₂ (ISCO, 40-g RediSep Gold column, 0 to 20% MeOH/DCM over 1 h, dry-loaded) to provide the title compound. LRMS (M+H)⁺: 260.0.

Step 4

5-(benzyloxy)-2,3-dihydro-1H-pyrido[2,1-f][1,2,4]triazine-4,6-dione (Intermediate A)

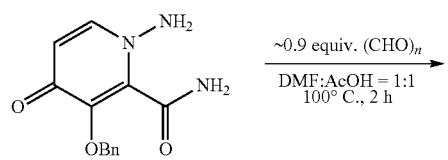

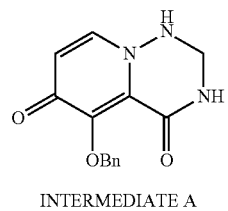

INTERMEDIATE A

To a solution of 1-amino-3-(benzyloxy)-4-oxo-1,4-dihydropyridine-2-carboxamide (2.0 g, 7.71 mmol) in DMF (30 mL) and AcOH (30 mL) was added paraformaldehyde (198 mg, ~0.9 eq). The mixture was stirred at 100° C. for 2 h, and then the resulting mixture was concentrated in vacuo. The resulting crude product was slurried with CH₂Cl₂ (20 mL), and the resulting suspension was filtered through a celite pad. The filter cake was collected and dried in vacuo to provide INTERMEDIATE A. ¹H NMR (400 MHz, DMSO-d₆): δ=8.96 (s, 1H), 7.73 (d, J=7.7 Hz, 1H), 7.60-7.50 (m, 2H), 7.40-7.26 (m, 4H), 6.21 (d, J=7.7 Hz, 1H), 5.09 (s, 2H), 4.38 (dd, J=3.6, 7.6 Hz, 2H). LRMS (M+H)⁺: 272.1.

Preparation of Intermediate B

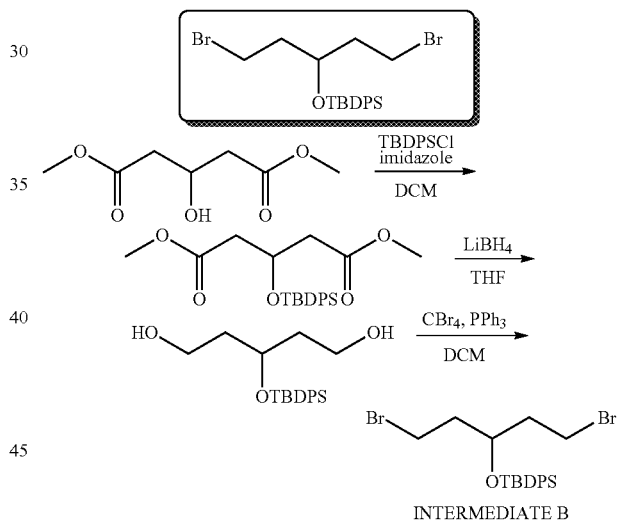

INTERMEDIATE B

Step 1

Dimethyl 3-((tert-butyldiphenylsilyl)oxy)pentanedioate

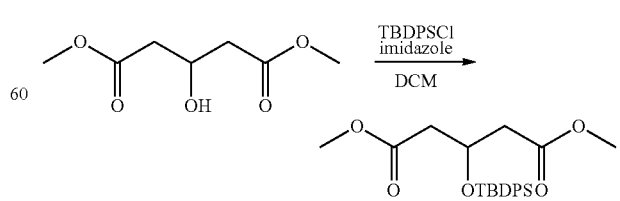

To a solution of dimethyl 3-hydroxypentanedioate (20 g, 114 mmol) in CH₂Cl₂ (100 mL) was added 1H-imidazole (15.46 g, 227 mmol) and TBDPSCl (46.8 g, 170 mmol) at 25° C. The solution was stirred at 25° C. for 3 h, and the mixture was filtrated and the filter cake was washed by CH$_2$Cl$_2$ (100 mL). The filtrate was concentrated in vacuo to afford the crude product, which was purified by gradient elution on SiO$_2$ (ISCO, 120 g RediSep Gold column, 0 to 10% EtOAc/Pet.ether over 90 min, dry-loaded) to afford the title compound. LRMS (M+H)$^+$: 437.2.

Step 2

3-((tert-butyldiphenylsilyl)oxy)pentane-1,5-diol

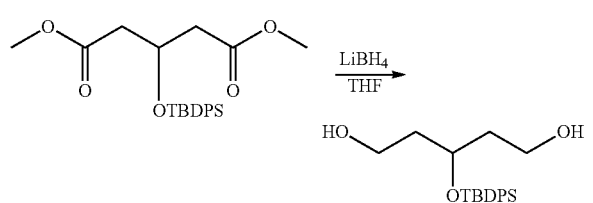

To a solution of dimethyl 3-((tert-butyldiphenylsilyl)oxy) pentanedioate (30.166 g, 72.8 mmol) in THF (125 mL) was added LiBH$_4$ (6.34 g, 291 mmol) at 0° C. The solution was stirred at 25° C. for 2 h, and then the reaction was quenched with 1M aq. HCl (20 mL) at 0° C. The mixture was extracted with ethyl acetate (3×50 mL), the combined organic layers were dried over Na$_2$SO$_4$, filtered, and concentrated in vacuo. The crude product was purified by gradient elution on SiO$_2$ (ISCO, 330 g RediSep Gold column, 0 to 50% EtOAc/Pet.ether over 90 min, dry-loaded) to afford the title compound. $^1$H NMR (400 MHz, CDCl$_3$): δ=7.64-7.72 (m, 4H), 7.33-7.46 (m, 6H), 4.07-4.12 (m, 1H), 3.52-3.65 (m, 4H), 1.64-1.87 (m, 4H), 1.05 (s, 9H). LRMS (M+H)$^+$: 359.0

Step 3

Tert-butyl((1,5-dibromopentan-3-yl)oxy)diphenylsilane

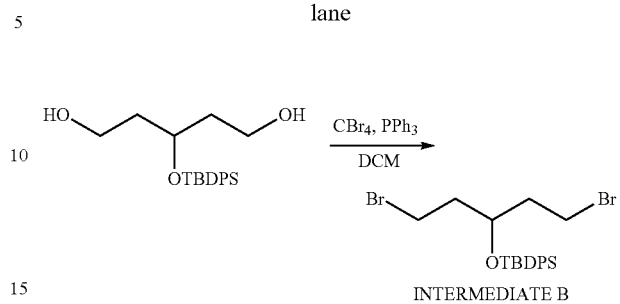

INTERMEDIATE B

To a solution of 3-((tert-butyldiphenylsilyl)oxy)pentane-1,5-diol (5.319 g, 14.83 mmol) in CH$_2$Cl$_2$ (100 mL) was added CBr$_4$ (14.76 g, 44.5 mmol) and PPh$_3$ (11.67 g, 44.5 mmol) at 0° C., the mixture was stirred at 25° C. for 6 h. The resulting mixture was quenched with saturated aq. Na$_2$SO$_3$ (30 mL), and the resulting mixture was extracted with EtOAc (3×100 mL), washed with brine (20 mL), dried over Na$_2$SO$_4$ and filtered. The crude product was purified by gradient elution on SiO$_2$ (ISCO, 330 g silica Flash Column, 0 to 10% EtOAc/Pet.ether over 90 min, dry-loaded) to provide the title compound. $^1$H NMR (400 MHz, CDCl$_3$): δ=7.69 (dd, J=7.9, 1.5 Hz, 4H), 7.37-7.48 (m, 6H), 4.02 (d, J=5.7 Hz, 1H), 3.33 (t, J=7.2 Hz, 4H), 1.94-2.10 (m, 4H), 1.07 (s, 9H).

PREPARATION OF EXAMPLES

Example 1

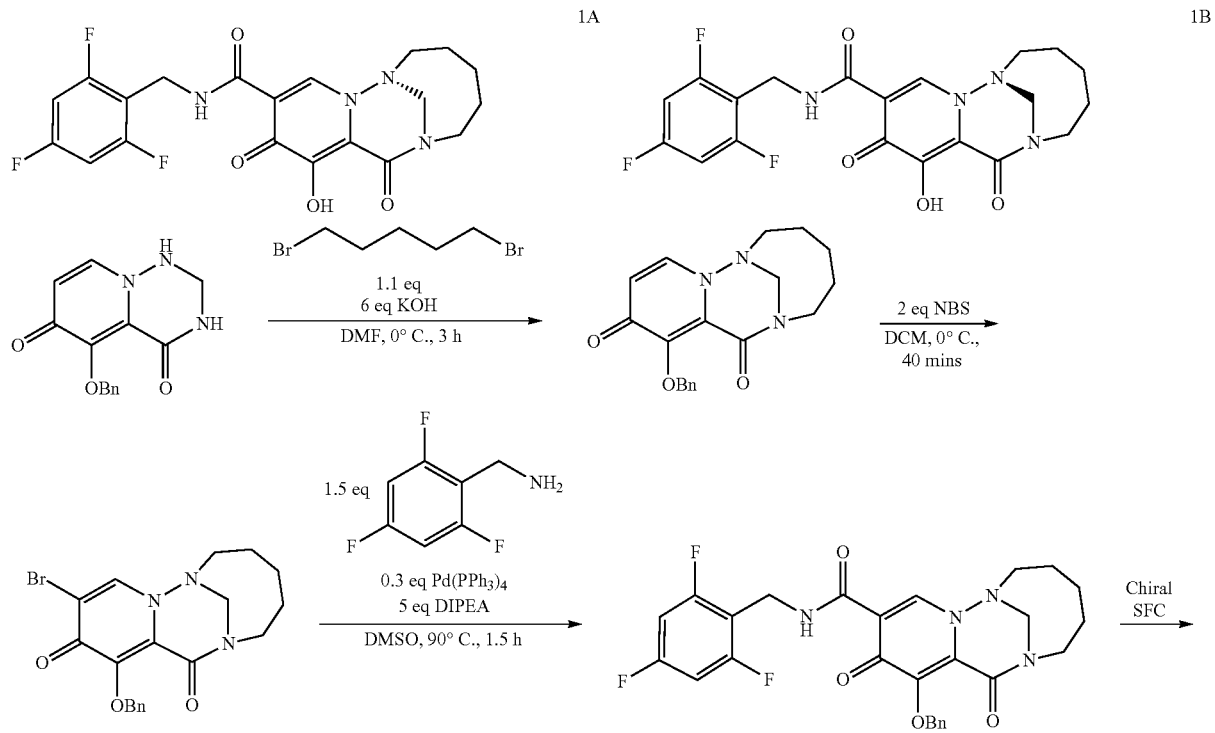

-continued

21

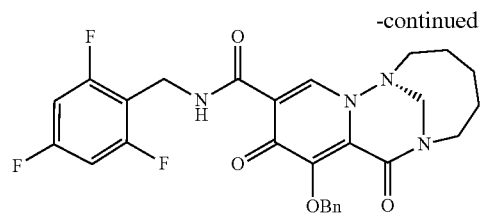

22

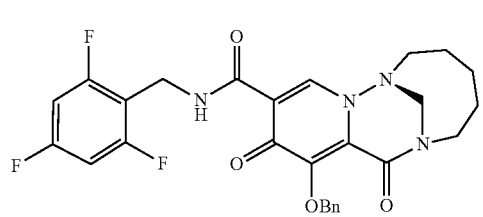

↓ 3 eq MgBr₂
CH₃CN. 20° C., 2 h

↓ 3 eq MgBr₂
CH₃CN. 20° C., 2 h

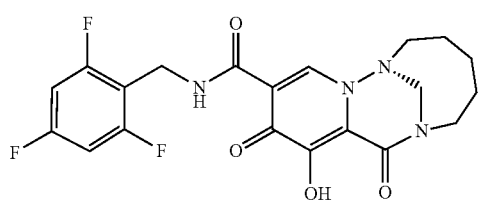

1A

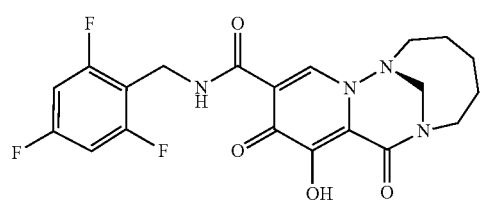

1B

Step 1

9-(benzyloxy)-3,4,5,6-tetrahydro-2H-1,7-methano-pyrido[1,2-b][1,2,5]triazecine-8,10-dione Step 2

9-(benzyloxy)-11-bromo-3,4,5,6-tetrahydro-2H-1,7-methanopyrido[1,2-b][1,2,5]triazecine-8,10-dione

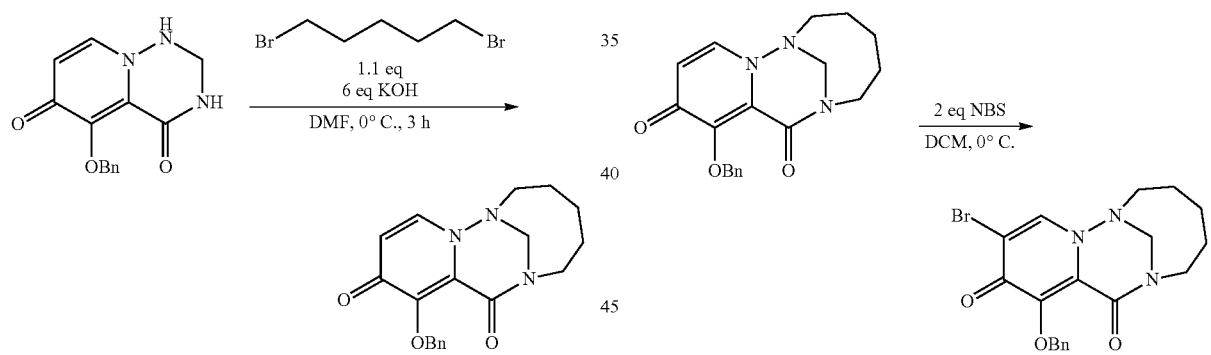

A mixture of INTERMEDIATE A (1.1 g, 4.05 mmol) and 1,5-dibromopentane (979.02 mg, 4.26 mmol) in DMF (100 mL) was cooled to 0° C. Powdered KOH (1.82 g, 32.44 mmol) was suspended in DMF (50 mL) and added dropwise (via syringe) to the stirred mixture at 0° C. over a period of 2 h. At this time, the resulting mixture was diluted with water (50 mL), extracted with CH₂Cl₂ (3×60 mL), washed with brine (20 mL), dried over Na₂SO₄ and filtered. The filtrate was concentrated in vacuo. The residue was purified by gradient elution on SiO₂ (ISCO, 40-g RediSep Gold column, 0 to 10% MeOH/EtOAc over 30 min, dry-loaded) to provide the title compound. $^1$H NMR (400 MHz, CDCl₃) δ=7.54 (d, J=7.7 Hz, 2H), 7.32-7.19 (m, 4H), 6.36-6.31 (m, 1H), 5.45 (dd, J=2.4, 10.4 Hz, 1H), 5.12 (dd, J=1.3, 10.1 Hz, 1H), 4.58-4.49 (m, 1H), 4.45-4.36 (m, 1H), 4.33-4.22 (m, 1H), 3.32 (dd, J=9.8, 11.8 Hz, 1H), 3.08-2.96 (m, 1H), 2.82-2.73 (m, 1H), 2.05-1.95 (m, 1H), 1.74-1.63 (m, 4H), 1.55 (m, 1H). LRMS (M+H)⁺: 340.1.

A mixture of 9-(benzyloxy)-3,4,5,6-tetrahydro-2H-1,7-methanopyrido[1,2-b][1,2,5]triazecine-8,10-dione (600 mg, 1.77 mmol) in CH₂Cl₂ (6 mL) was cooled to 0° C., then NBS (943.95 mg, 5.3 mmol) was added in portions as a solid. The mixture was stirred at 0° C. for 45 min, and the resulting mixture was quenched with saturated aq Na₂SO₃ (8 mL), extracted with CH₂Cl₂ (3×10 mL), washed with brine (10 mL), dried over Na₂SO₄ and filtered. The filtrate was concentrated in vacuo. The residue was purified by normal phase chromatography (ISCO, 20-g RediSep Gold column, 0 to 10% MeOH/EtOAc over 2 h, dry-loaded) to provide the title compound. $^1$H NMR (400 MHz, CDCl₃) δ=7.85 (s, 1H), 7.65 (d, J=6.6 Hz, 2H), 7.38-7.29 (m, 3H), 5.55 (d, J=10.1 Hz, 1H), 5.19 (d, J=10.1 Hz, 1H), 4.72-4.63 (m, 1H), 4.50 (d, J=14.5 Hz, 1H), 4.41-4.32 (m, 1H), 3.51-3.38 (m, 1H), 3.21-3.11 (m, 1H), 2.90-2.81 (m, 1H), 2.13-2.03 (m, 1H), 1.79 (br d, J=11.0 Hz, 4H), 1.64-1.59 (m, 3H). LRMS (M+H)⁺: 418.1.

Step 3

9-(benzyloxy)-8,10-dioxo-N-(2,4,6-trifluorobenzyl)-3,4,5,6,8,10-hexahydro-2H-1,7-methanopyrido[1,2-b][1,2,5]triazecine-11-carboxamide

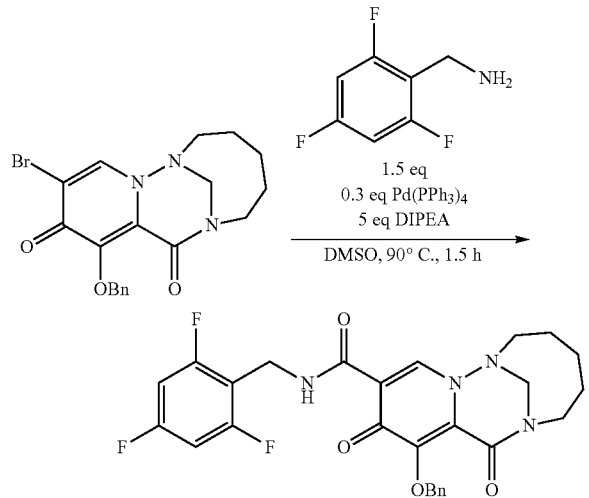

To a solution of 9-(benzyloxy)-11-bromo-3,4,5,6-tetrahydro-2H-1,7-methanopyrido[1,2-b][1,2,5]triazecine-8,10-dione (591 mg, 1.41 mmol) in DMSO (6 mL) was added (2,4,6-trifluorophenyl)methanamine (341.48 mg, 2.12 mmol), Pd(PPh$_3$)$_4$ (489.82 mg, 423.87 μmol) and DIEA (1.72 mL, 9.89 mmol). The mixture was stirred at 90° C. for 1.5 h under CO (15 psi). The mixture was filtered and purified by preparative HPLC (Column: Phenomenex Synergi Max-RP 150*50 mm, 10 μm; Conditions: water (0.1% TFA)/MeCN; begin B 0%, end B 30%; gradient time 20 min; 100% B hold time 5 min, flowrate 120 mL/min) to provide the title compound. $^1$H NMR (400 MHz, CDCl$_3$) δ=10.31 (t, J=5.4 Hz, 1H), 8.46 (s, 1H), 7.54-7.48 (m, 2H), 7.31-7.20 (m, 3H), 6.67-6.54 (m, 2H), 5.42 (d, J=10.1 Hz, 1H), 5.13 (d, J=9.9 Hz, 1H), 4.64-4.44 (m, 4H), 4.30 (br dd, J=7.6, 14.0 Hz, 1H), 3.47-3.33 (m, 1H), 3.1-3.03 (m, 1H), 2.84-2.75 (m, 1H), 2.00 (dd, J=6.2, 10.6 Hz, 1H), 1.70 (m, 3H), 1.60 (m, 2H). LRMS (M+H)$^+$: 527.2.

Step 4

9-(benzyloxy)-8,10-dioxo-N-(2,4,6-trifluorobenzyl)-3,4,5,6,8,10-hexahydro-2H-1,7-methanopyrido[1,2-b][1,2,5]triazecine-11-carboxamide

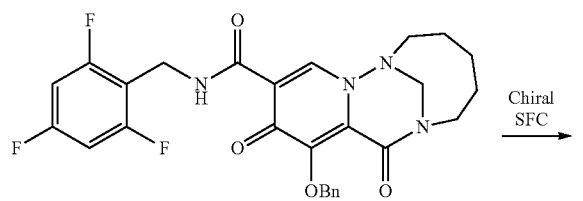

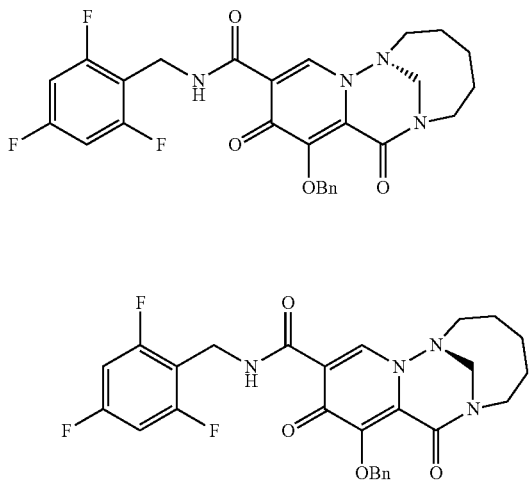

Enantiomers were separated by preparative chiral SFC (Column: YMC CHIRAL Amylose-C 250*30 mm, 5 μm; Conditions: CO$_2$/IPA (0.1% NH$_4$OH); begin B 40%, end B 40% (isocratic); flowrate 60 mL/min; time: 16.2 min; peak 1 rt=9.25 min, peak 2 rt=12.5 min) to provide 9-(benzyloxy)-8,10-dioxo-N-(2,4,6-trifluorobenzyl)-3,4,5,6,8,10-hexahydro-2H-1,7-methanopyrido[1,2-b][1,2,5]triazecine-11-carboxamide (PEAK 1, >99.9% ee) and 9-(benzyloxy)-8,10-dioxo-N-(2,4,6-trifluorobenzyl)-3,4,5,6,8,10-hexahydro-2H-1,7-methanopyrido[1,2-b][1,2,5]triazecine-11-carboxamide (PEAK 2, 99.6% ee). LRMS (M+H)$^+$: 527.2.

Step 5

9-hydroxy-8,10-dioxo-N-(2,4,6-trifluorobenzyl)-3,4,5,6,8,10-hexahydro-2H-1,7-methanopyrido[1,2-b][1,2,5]triazecine-11-carboxamide

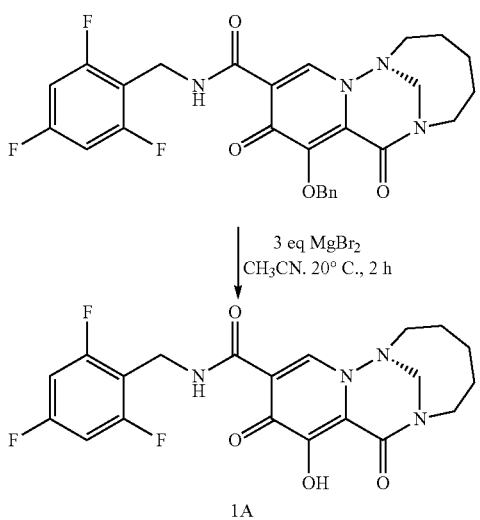

1A

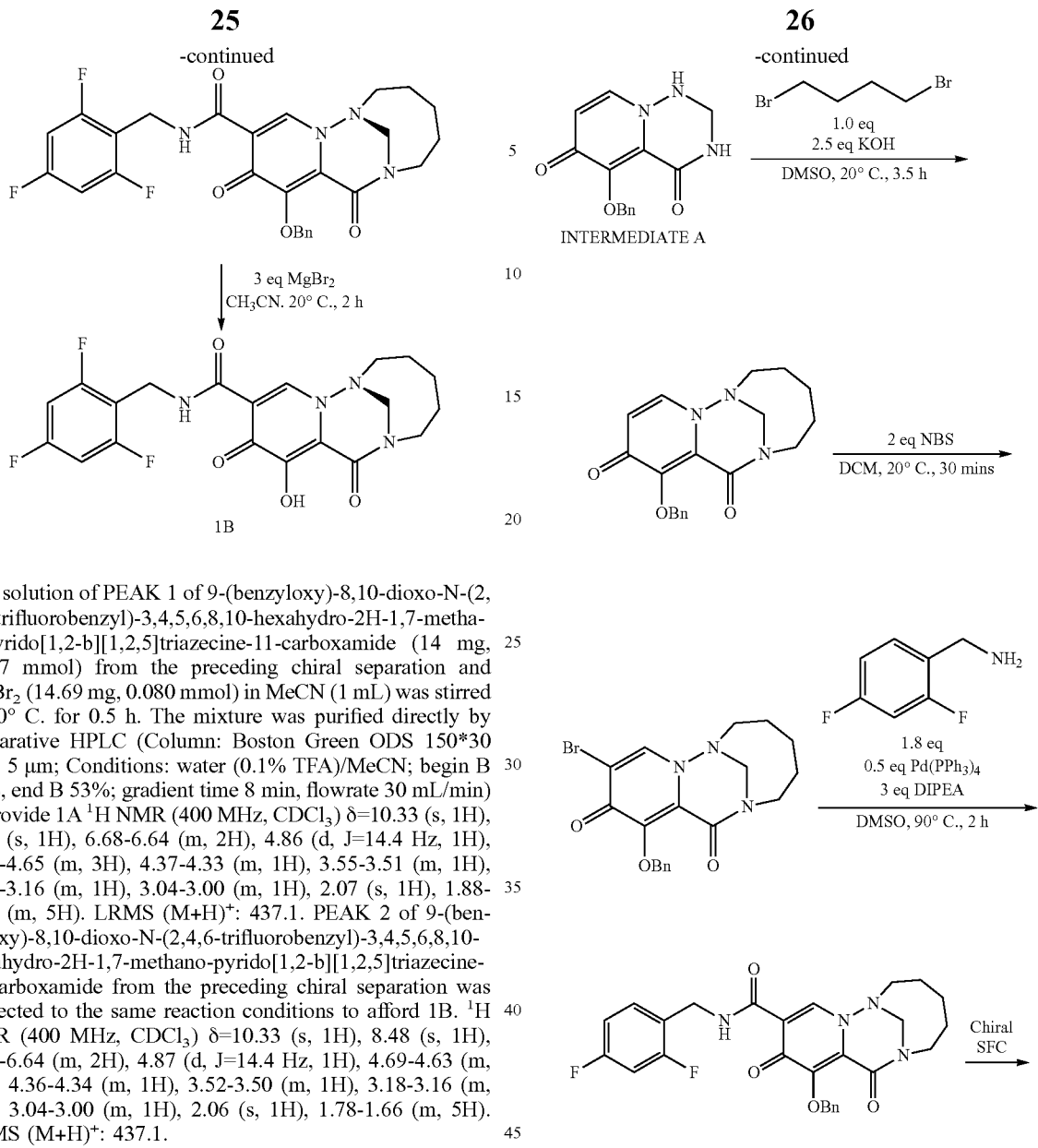

A solution of PEAK 1 of 9-(benzyloxy)-8,10-dioxo-N-(2,4,6-trifluorobenzyl)-3,4,5,6,8,10-hexahydro-2H-1,7-methanopyrido[1,2-b][1,2,5]triazecine-11-carboxamide (14 mg, 0.027 mmol) from the preceding chiral separation and MgBr$_2$ (14.69 mg, 0.080 mmol) in MeCN (1 mL) was stirred at 40° C. for 0.5 h. The mixture was purified directly by preparative HPLC (Column: Boston Green ODS 150*30 mm, 5 μm; Conditions: water (0.1% TFA)/MeCN; begin B 23%, end B 53%; gradient time 8 min, flowrate 30 mL/min) to provide 1A $^1$H NMR (400 MHz, CDCl$_3$) δ=10.33 (s, 1H), 8.48 (s, 1H), 6.68-6.64 (m, 2H), 4.86 (d, J=14.4 Hz, 1H), 4.69-4.65 (m, 3H), 4.37-4.33 (m, 1H), 3.55-3.51 (m, 1H), 3.18-3.16 (m, 1H), 3.04-3.00 (m, 1H), 2.07 (s, 1H), 1.88-1.68 (m, 5H). LRMS (M+H)$^+$: 437.1. PEAK 2 of 9-(benzyloxy)-8,10-dioxo-N-(2,4,6-trifluorobenzyl)-3,4,5,6,8,10-hexahydro-2H-1,7-methano-pyrido[1,2-b][1,2,5]triazecine-11-carboxamide from the preceding chiral separation was subjected to the same reaction conditions to afford 1B. $^1$H NMR (400 MHz, CDCl$_3$) δ=10.33 (s, 1H), 8.48 (s, 1H), 6.68-6.64 (m, 2H), 4.87 (d, J=14.4 Hz, 1H), 4.69-4.63 (m, 3H), 4.36-4.34 (m, 1H), 3.52-3.50 (m, 1H), 3.18-3.16 (m, 1H), 3.04-3.00 (m, 1H), 2.06 (s, 1H), 1.78-1.66 (m, 5H). LRMS (M+H)$^+$: 437.1.

Example 2

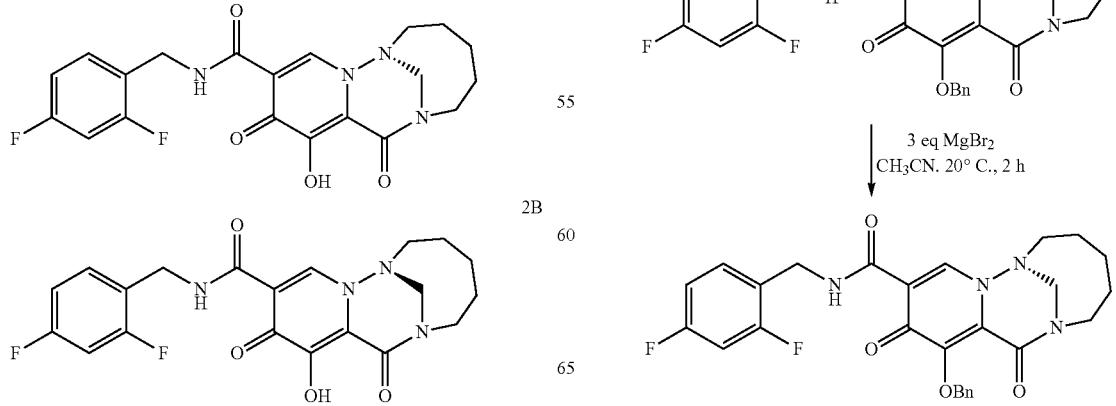

-continued

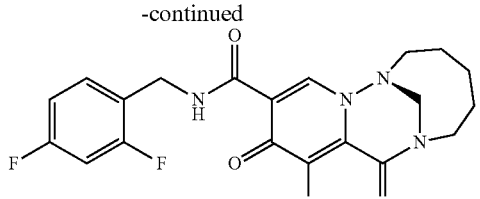

3 eq MgBr₂
CH₃CN, 20° C., 2 h

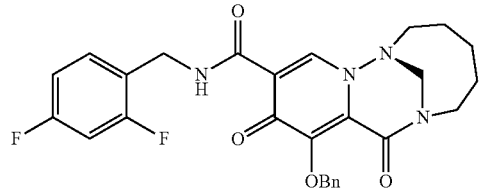

Step 1

8-(benzyloxy)-2,3,4,5-tetrahydro-1,6-methanopyrido[1,2-b][1,2,5]triazonine-7,9-dione

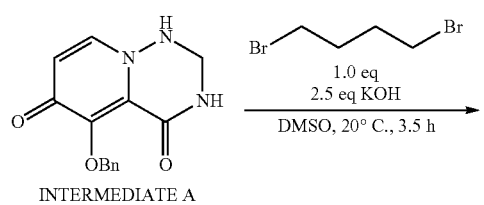

INTERMEDIATE A

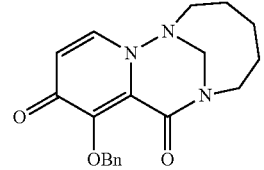

1.0 eq
2.5 eq KOH
DMSO, 20° C., 3.5 h

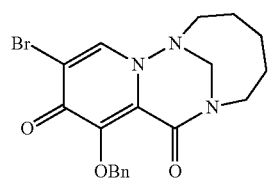

Solid KOH (0.776 g, 13.82 mmol) was suspended in DMSO (40 mL), and the solution was stirred at 70° C. until most solid particles disappeared. Then the cooled base solution was added dropwise into a solution of INTERMEDIATE A (1.271 g, 4.69 mmol) and 1,4-dibromobutane (1.01 g, 4.69 mmol) in DMSO (150 mL) over 2.5 h at 20° C. The reaction was stirred at 20° C. for another 1 h. The mixture was poured into water (200 mL) and extracted with MeOH/DCM (1:10, 3×200 mL). The combined organic layers were washed with brine, dried over Na₂SO₄, filtered, and concentrated in vacuo. The residue was purified by elution on SiO₂ (isocratic, 5% MeOH in CH₂Cl₂) to provide the title compound. ¹H NMR (400 MHz, CDCl₃) δ=7.87 (s, 1H), 7.43 (d, J=7.6 Hz, 2H), 7.36-7.32 (m, 4H), 5.32 (d, J=9.6 Hz, 1H), 5.27 (d, J=9.6 Hz, 1H), 4.63 (s, 1H), 4.47 (s, 1H), 4.30 (s, 1H), 3.39-3.47 (m, 2H), 3.13 (s, 1H), 2.24-2.21 (m, 1H), 1.87-1.56 (m, 3H). LRMS (M+H)⁺: 340.0.

Step 2

8-(benzyloxy)-10-bromo-2,3,4,5-tetrahydro-1,6-methanopyrido[1,2-b][1,2,5]triazonine-7,9-dione

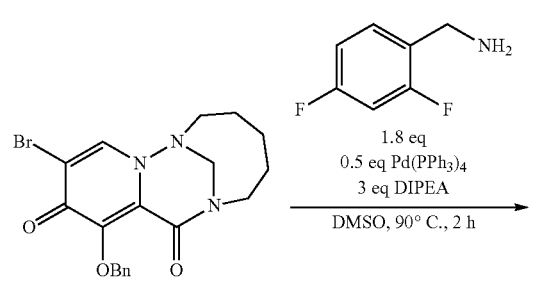

2 eq NBS
DCM, 20° C., 30 mins

To a stirred yellow solution of 8-(benzyloxy)-2,3,4,5-tetrahydro-1,6-methanopyrido[1,2-b][1,2,5]triazonine-7,9-dione (40 mg, 0.123 mmol) in CH₂Cl₂ (1 mL) was added NBS (43.8 mg, 0.246 mmol) at 0° C. The mixture was stirred at 20° C. for 0.5 h and then purified directly by preparative TLC eluting with 5% MeOH in CH₂Cl₂ to provide the title compound. ¹H NMR (400 MHz, CDCl₃) δ=7.89 (s, 1H), 7.14 (d, J=7.6 Hz, 2H), 7.36-7.29 (m, 3H), 5.61 (d, J=10.0 Hz, 1H), 5.16 (d, J=10.0 Hz, 1H), 4.55 (d, J=10.0 Hz, 1H), 4.43-4.21 (m, 1H), 4.19 (d, J=10.0 Hz, 1H), 3.37-3.30 (m, 2H), 3.27-3.26 (m, 1H), 2.18-2.16 (m, 1H), 1.81-1.58 (m, 3H). LRMS (M+H)⁺: 406.1.

Step 3

8-(benzyloxy)-N-(2,4-difluorobenzyl)-7,9-dioxo-2,3,4,5,7,9-hexahydro-1,6-methanopyrido[1,2-b][1,2,5]triazonine-10-carboxamide

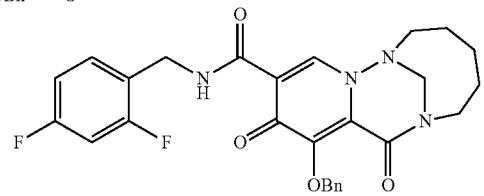

A mixture of 8-(benzyloxy)-10-bromo-2,3,4,5-tetrahydro-1,6-methanopyrido[1,2-b][1,2,5]triazonine-7,9-dione (52 mg, 0.129 mmol), (2,4-difluorophenyl)methanamine (33.1 mg, 0.232 mmol), Pd(PPh₃)₄ (74.3 mg, 0.064 mmol) and DIEA (0.067 mL, 0.386 mmol) in DMSO (1 mL) was stirred under CO balloon (15 psi) at 90° C. for 2 h. The mixture was filtered and the filtrate purified by preparative HPLC (Column: YMC-Actus Pro C18 150*30 mm, 5 μm; Conditions: water (0.1% TFA)/MeCN; begin B 0%, end B 30%; gradient time 11 min; 100% B hold time 1.1 min, flowrate 40 mL/min) to provide the title compound. LRMS (M+H)$^+$: 495.2.

Step 4

8-(benzyloxy)-N-(2,4-difluorobenzyl)-7,9-dioxo-2,3,4,5,7,9-hexahydro-1,6-methanopyrido[1,2-b][1,2,5]triazonine-10-carboxamide

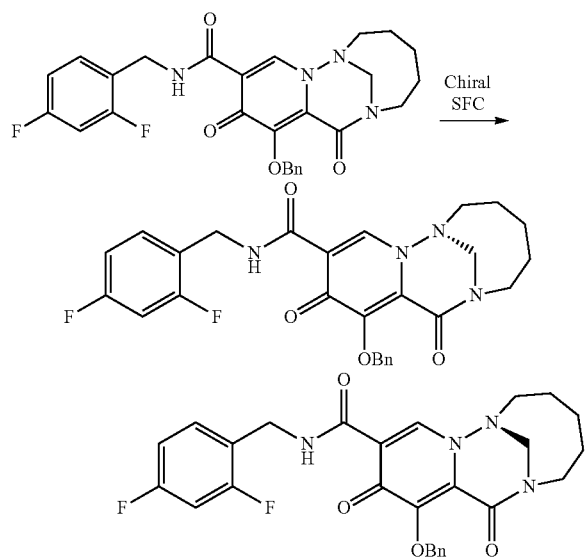

Enantiomers were separated by preparative chiral SFC (Column: CHIRALCEL-AS 250*30 mm, 5 μm; Conditions: isocratic CO$_2$/EtOH (0.1% NH$_4$OH); begin B 45%, end B 45% (isocratic); flowrate 50 mL/min; peak 1 rt=0.8 min, peak 2 rt=1.2 min) to provide 8-(benzyloxy)-N-(2,4-difluorobenzyl)-7,9-dioxo-2,3,4,5,7,9-hexahydro-1,6-methanopyrido[1,2-b][1,2,5]triazonine-10-carboxamide (PEAK 1, >99.9% ee) and 8-(benzyloxy)-N-(2,4-difluorobenzyl)-7,9-dioxo-2,3,4,5,7,9-hexahydro-1,6-methanopyrido[1,2-b][1,2,5]triazonine-10-carboxamide (PEAK 2, >99.9% ee). LRMS (M+H)$^+$: 495.2.

Step 5

N-(2,4-difluorobenzyl)-8-hydroxy-7,9-dioxo-2,3,4,5,7,9-hexahydro-1,6-methanopyrido[1,2-1)][1,2,5]triazonine-10-carboxamide

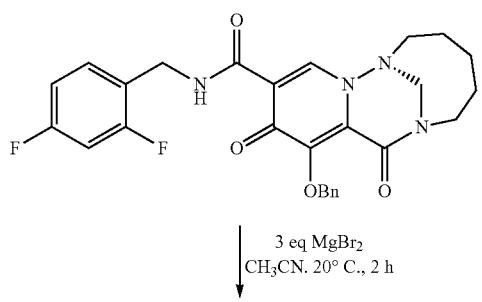

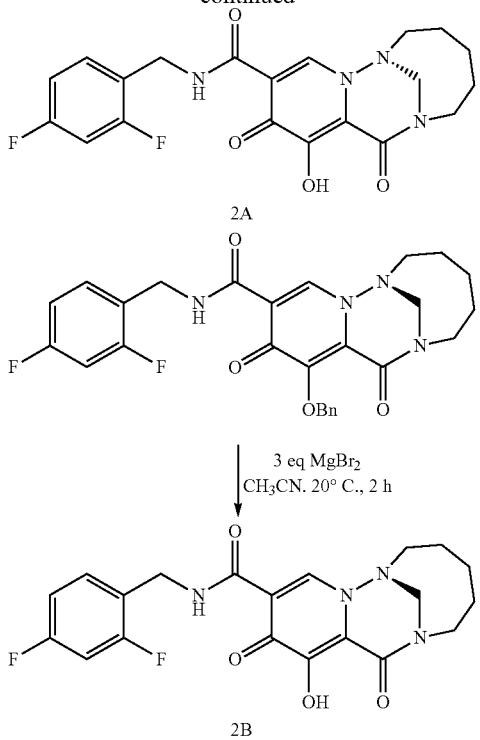

A solution of PEAK 1 of 8-(benzyloxy)-N-(2,4-difluorobenzyl)-7,9-dioxo-2,3,4,5,7,9-hexahydro-1,6-methanopyrido[1,2-b][1,2,5]triazonine-10-carboxamide (10 mg, 0.020 mmol) and MgBr$_2$ (11.17 mg, 0.061 mmol) in MeCN (1 mL) was stirred at 20° C. for 2 h. The mixture was purified directly by preparative HPLC (Column: DuraShell 150*30 mm, 5 μm; Conditions: water (0.1% TFA)/MeCN; begin B 28%, end B 58%; gradient time 10 min, 100% B hold time 2.5 min, flowrate 30 mL/min) to provide 2A. $^1$H NMR (400 MHz, CDCl$_3$) δ=10.34 (s, 1H), 8.57 (s, 1H), 7.40-7.34 (m, 1H), 6.85-6.70 (m, 2H), 4.85 (d, J=14 Hz, 1H), 4.46 (s, 2H), 4.43-4.37 (m, 2H), 3.41-4.39 (m, 2H), 3.31-3.23 (m, 1H), 2.31-2.25 (m, 1H), 1.76-1.75 (m, 1H), 1.74-1.58 (m, 2H). LRMS (M+H)$^+$: 405.1. PEAK 2 of 8-(benzyloxy)-N-(2,4-difluorobenzyl)-7,9-dioxo-2,3,4,5,7,9-hexahydro-1,6-methanopyrido[1,2-b][1,2,5]triazonine-10-carboxamide from the preceding chiral separation was subjected to the same reaction conditions to afford 2B. $^1$H NMR (400 MHz, CDCl$_3$) δ=10.34 (s, 1H), 8.57 (s, 1H), 7.40-7.34 (m, 1H), 6.85-6.79 (m, 2H), 4.82 (d, J=14 Hz, 1H), 4.66 (s, 2H), 4.43-4.37 (m, 2H), 3.41-3.39 (m, 2H), 3.31-3.23 (m, 1H), 2.31-2.25 (m, 1H), 1.76-1.75 (m, 1H), 1.74-1.60 (m, 2H). LRMS (M+H)$^+$: 405.1.

Example 3

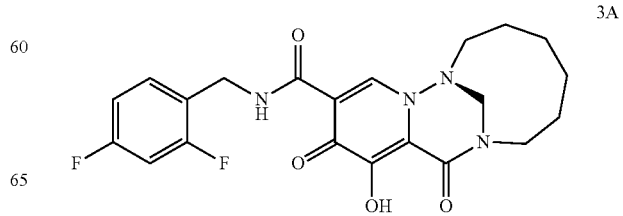

3B
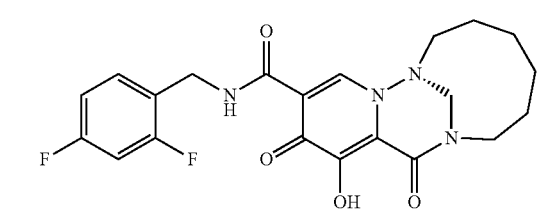
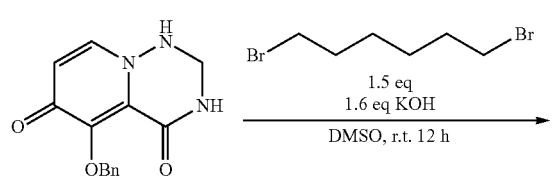
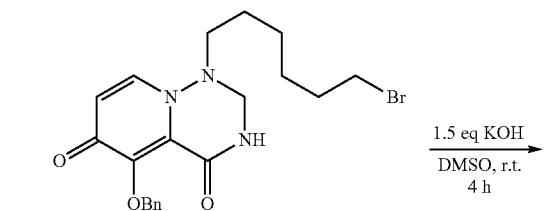
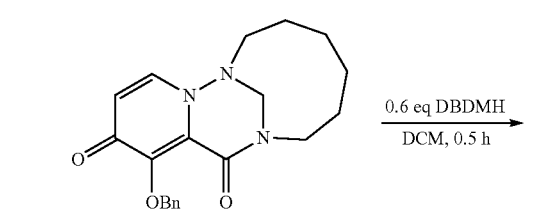
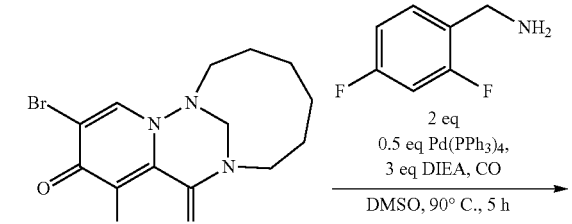
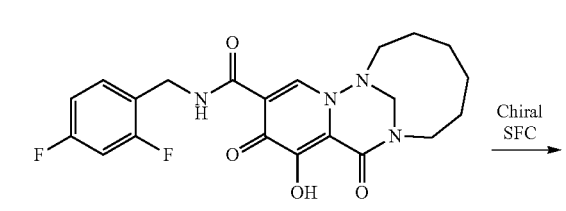
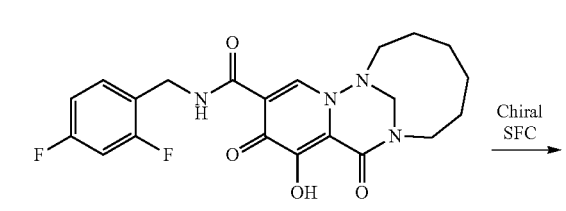
Step 1
5-(benzyloxy)-1-(6-bromohexyl)-2,3-dihydro-1H-pyrido[2,1-f][1,2,4]triazine-4,6-dione Solid KOH (0.371 g, 6.61 mmol) was suspended in DMSO (20 mL), and the solution was stirred at 70° C. until most solid particles disappeared. INTERMEDIATE A (1.4 g, 5.16 mmol) and 1,6-dibromohexane (1.89 g, 7.74 mmol) were added, and the reaction mixture was stirred at 20° C. for 8 h. The mixture was poured into water (5 mL) and extracted with CH$_2$Cl$_2$ (3×5 mL). The combined organic layers were dried over Na$_2$SO$_4$, filtered, concentrated in vacuo and the crude product was purified by gradient elution on SiO$_2$ (isocratic, 0% to 10% MeOH in 3:1 EtOAc/EtOH) to provide the title compound. LRMS (M+H)$^+$: 434.0, 436.0.

Step 2

10-(benzyloxy)-2,3,4,5,6,7-hexahydro-1,8-methanopyrido[1,2-b][1,2,5]triazacycloundecine-9,11-dione

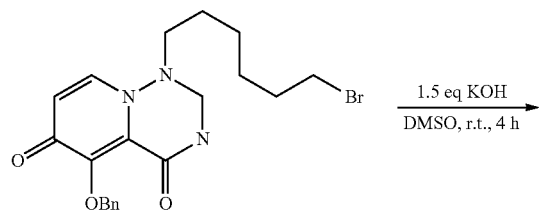

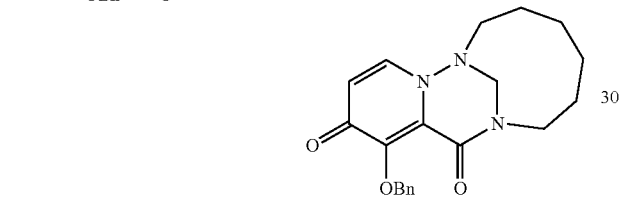

To a solution of 5-(benzyloxy)-1-(6-bromohexyl)-2,3-dihydro-1H-pyrido[2,1-f][1,2,4]triazine-4,6-dione (1.1 g, 2.53 mmol) in DMSO (20 mL) was added powdered KOH (0.213 g, 3.80 mmol) in one portion at 20° C. and stirred at this temperature for 4 h. The mixture was poured into water (10 mL) and extracted with CH$_2$Cl$_2$ (3×10 mL). The combined organic layers were purified directly by preparative HPLC (Phenomenex Luna C18 250*80 mm, 10 μm; Conditions: water (0.1% TFA)/MeCN; begin B 15%, end B 35%; flowrate 250 mL/min) to provide the title compound. $^1$H NMR (400 MHz, CDCl$_3$) δ=7.95 (br d, J=7.3 Hz, 1H), 7.59 (br d, J=7.3 Hz, 1H), 7.49-7.56 (m, 2H), 7.33-7.41 (m, 3H), 5.40 (d, J=9.9 Hz, 1H), 5.29 (d, J=9.9 Hz, 1H) 4.72 (s, 2H), 4.30-4.47 (m, 1H), 3.23-3.46 (m, 2H), 2.76-2.86 (m, 1H), 1.48-2.11 (m, 8H). LRMS (M+H)$^+$: 354.2.

Step 3

10-(benzyloxy)-12-bromo-2,3,4,5,6,7-hexahydro-1,8-methanopyrido[1,2-b][1,2,5]triazacycloundecine-9,11-dione

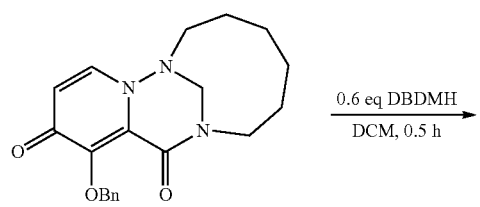

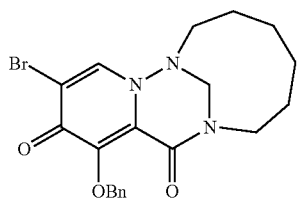

To a stirred solution of 10-(benzyloxy)-2,3,4,5,6,7-hexahydro-1,8-methanopyrido[1,2-b][1,2,5]triazacycloundecine-9,11-dione (350 mg, 0.990 mmol) in CH$_2$Cl$_2$ (5 mL) was added 1,3-dibromo-5,5-dimethylimidazolidine-2,4-dione (170 mg, 0.594 mmol) in one portion at 20° C., and the mixture was stirred at 20° C. for 0.5 h. The reaction mixture was purified directly by preparative TLC eluting with EtOAc to provide the title compound. $^1$H NMR (400 MHz, CDCl$_3$) δ=7.86 (s, 1H), 7.65 (d, J=7.1 Hz, 2H), 7.28-7.38 (m, 3H), 5.51 (d, J=9.9 Hz, 1H), 5.19 (d, J=9.9 Hz, 1H), 4.58-4.74 (m, 2H), 3.16-3.35 (m, 2H), 2.67-2.77 (m, 2H), 1.48-1.99 (m, 8H). LRMS (M+H)$^+$: 432.0, 434.0.

Step 4

10-(benzyloxy)-N-(2,4-difluorobenzyl)-9,11-dioxo-2,3,4,5,6,7,9,11-octahydro-1,8-methanopyrido[1,2-b][1,2,5]triazacycloundecine-12-carboxamide

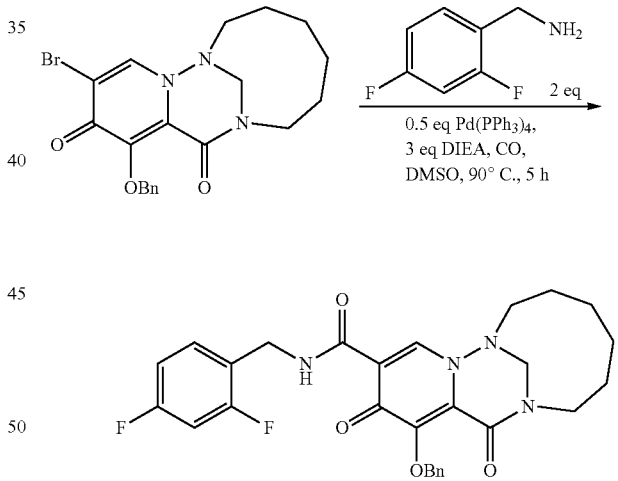

A mixture of 10-(benzyloxy)-12-bromo-2,3,4,5,6,7-hexahydro-1,8-methanopyrido[1,2-b][1,2,5]triazacycloundecine-9,11-dione (100 mg, 0.231 mmol), (2,4-difluorophenyl)-methanamine (66.2 mg, 0.463 mmol), Pd(Ph$_3$P)$_4$ (134 mg, 0.116 mmol) and DIEA (0.121 mL, 0.694 mmol) in DMSO (0.5 mL) was stirred under CO balloon (15 psi) at 90° C. for 5 h. The mixture was filtered and the filtrate was diluted with water (5 mL) and extracted with EtOAc (3×10 mL). The combined organic layer was washed with brine (5 mL), dried over anhydrous Na$_2$SO$_4$ and filtered. The organic layer was concentrated in vacuo and purified by preparative TLC eluting with EtOAc to provide the title compound. LRMS (M+H)$^+$: 523.2.

Step 5

10-(benzyloxy)-N-(2,4-difluorobenzyl)-9,11-dioxo-2,3,4,5,6,7,9,11-octahydro-1,8-methanopyrido[1,2-b][1,2,5]triazacycloundecine-12-carboxamide

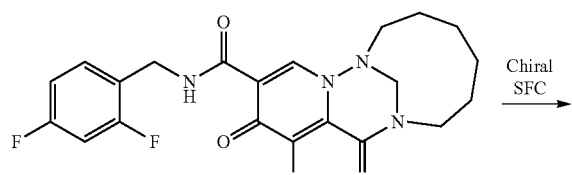

Enantiomers were separated by preparative chiral SFC (Column: CHIRALCEL-OD 250*30 mm, 10 μm; Conditions: isocratic CO$_2$/EtOH (0.1% NH$_4$OH); begin B 50%, end B 50% (isocratic); flowrate 80 mL/min; peak 1 rt=0.74 min, peak 2 rt=1.26 min) to provide 10-(benzyloxy)-N-(2,4-difluorobenzyl)-9,11-dioxo-2,3,4,5,6,7,9,11-octahydro-1,8-methanopyrido[1,2-b][1,2,5]tria-zacycloundecine-12-carboxamide (PEAK 1, >99.9% ee) and 10-(benzyloxy)-N-(2,4-difluorobenzyl)-9,11-dioxo-2,3,4,5,6,7,9,11-octahydro-1,8-methanopyrido[1,2-b][1,2,5]triaza-cycloundecine-12-carboxamide (PEAK 2, 99.02% ee). LRMS (M+H)$^+$: 523.2.

Step 6

N-(2,4-difluorobenzyl)-10-hydroxy-9,11-dioxo-2,3,4,5,6,7,9,11-octahydro-1,8-methanopyrido[1,2-b][1,2,5]triazacycloundecine-12-carboxamide

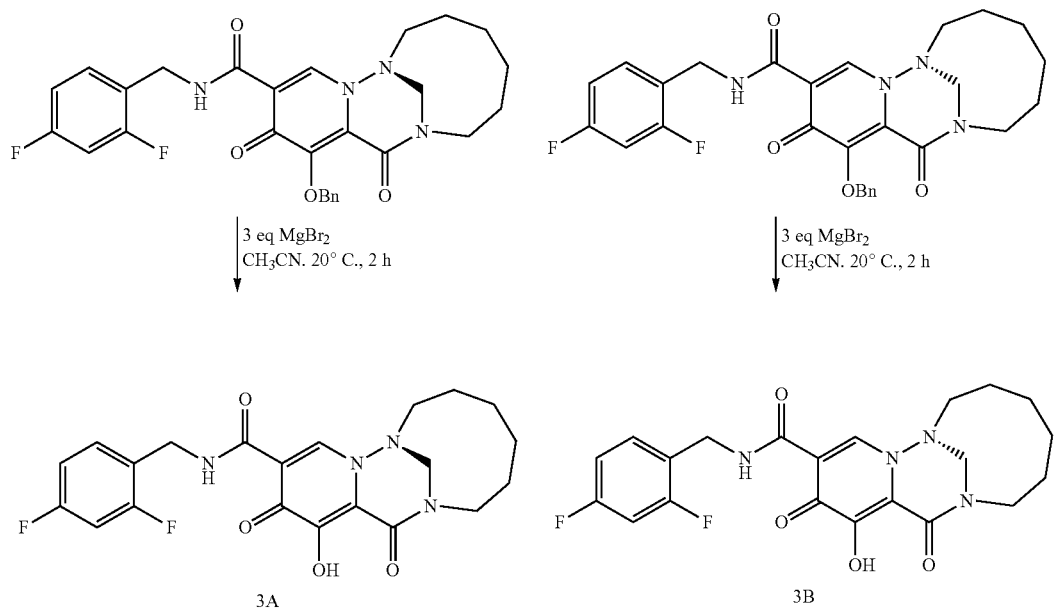

-continued

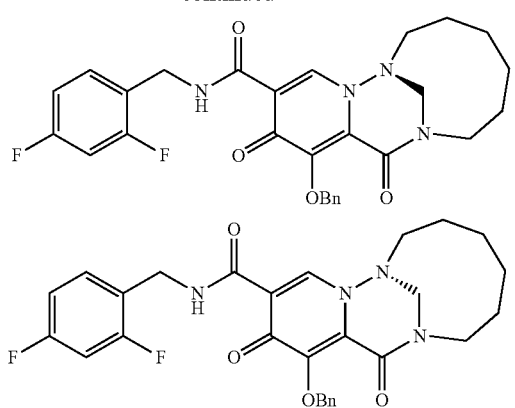

To a solution of PEAK 1 of 10-(benzyloxy)-N-(2,4-difluorobenzyl)-9,11-dioxo-2,3,4,5,6,7,9,11-octahydro-1,8-methanopyrido[1,2-b][1,2,5]triazacycloundecine-12-carboxamide (40 mg, 0.077 mmol) in MeCN (2 mL) was added MgBr$_2$ (14.09 mg, 0.077 mmol), and the mixture was stirred at 40° C. for 2 h. The mixture was filtered and purified directly by reverse phase preparative HPLC (Column: Boston Green ODS 150*30 mm, 5 μm; Conditions: water (0.1% TFA)/MeCN; begin B 38%, end B 68%; gradient time 10 min; 100% B hold time 2.5 min, flowrate 25 mL/min) to provide 3A. $^1$H NMR (400 MHz, CDCl$_3$) δ=10.39 (br s, 1H), 8.46 (s, 1H), 7.30-7.41 (m, 1H), 6.71-6.86 (m, 2H), 4.72-4.91 (m, 2H), 4.55-4.67 (m, 2H), 4.32-4.44 (m, 1H), 3.19-3.32 (m, 2H), 2.77-2.88 (m, 1H), 1.75-1.92 (m, 3H), 1.46-1.66 (m, 5H). LRMS (M+H)$^+$: 433.2. PEAK 2 of 10-(benzyloxy)-N-(2,4-difluorobenzyl)-9,11-dioxo-2,3,4,5,-

6,7,9,11-octahydro-1,8-methanopyrido[1,2-b][1,2,5]triaza-cycloundecine-12-carboxamide from the preceding chiral separation was subjected to the same reaction conditions to afford 3B. $^1$H NMR (400 MHz, CDCl$_3$) δ=10.32-10.48 (m, 1H), 8.47 (s, 1H), 7.30-7.42 (m, 1H), 6.72-6.87 (m, 2H), 4.83-4.90 (m, 1H), 4.73-4.80 (m, 1H), 4.58-4.68 (m, 2H), 4.34-4.43 (m, 1H), 3.20-3.31 (m, 2H), 2.80-2.86 (m, 1H), 1.77-1.99 (m, 3H), 1.47-1.73 (m, 5H). LRMS (M+H)$^+$: 433.2.
Example 4
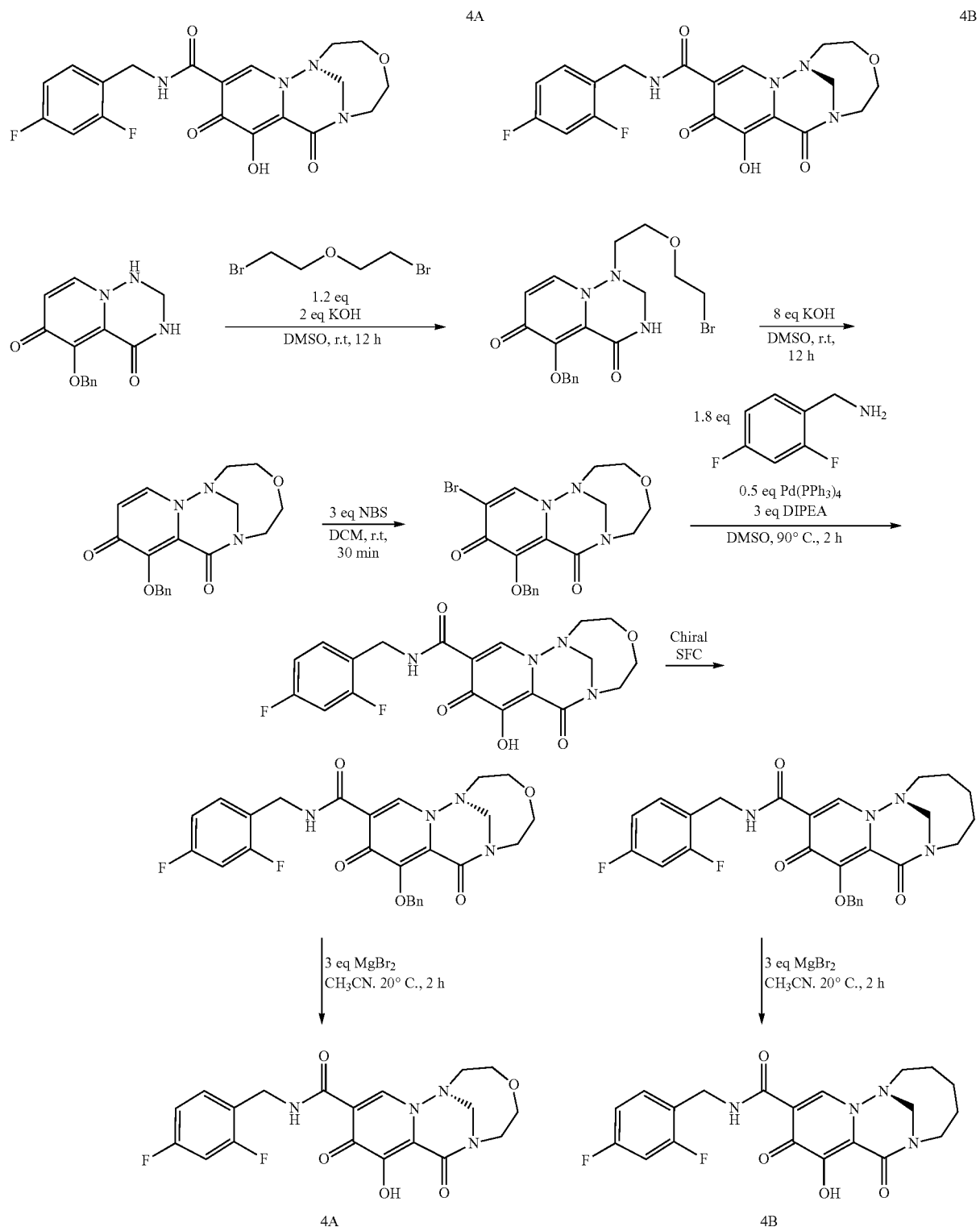

Step 1

5-(benzyloxy)-1-(2-(2-bromoethoxy)ethyl)-2,3-di-hydro-1H-pyrido[2,1-f][1,2,4]triazine-4,6-dione

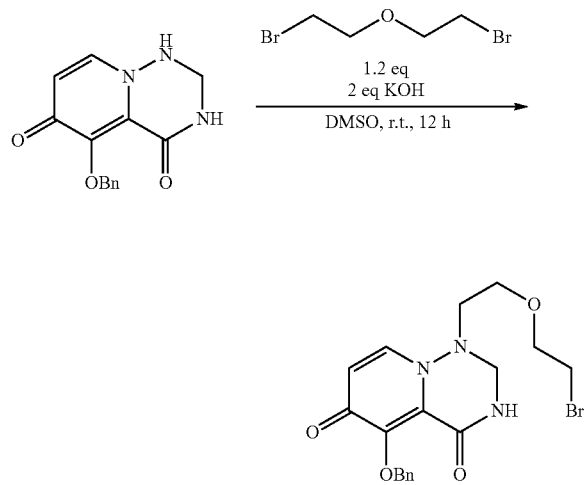

Solid KOH (124 mg, 2.21 mmol) was suspended in DMSO (25 mL), and the solution was stirred at 70° C. until most solid particles disappeared. INTERMEDIATE A (300 mg, 1.11 mmol) and 1-bromo-2-(2-bromoethoxy)ethane (308 mg, 1.33 mmol) were added, and the reaction mixture was stirred at 20° C. for 3 h. The mixture was poured into water (10 mL) and extracted with DCM (3×10 mL). The combined organic layers were washed with brine, dried over $Na_2SO_4$, filtered, the filtrate was concentrated in vacuo. The crude residue was purified by preparative TLC eluting with 10% MeOH in $CH_2Cl_2$ to provide the title compound. $^1H$ NMR (400 MHz, $CDCl_3$) δ=7.79 (d, J=7.6 Hz, 1H), 7.51-7.46 (m, 2H), 7.36-7.32 (m, 3H), 7.15 (d, J=7.2 Hz, 1H), 5.24 (s, 2H), 4.62 (s, 1H), 3.80-3.78 (m, 2H), 3.68 (s, 4H), 3.51-3.49 (m, 2H). LRMS (M+H)$^+$: 424.1.

Step 2

9-(benzyloxy)-2,3,5,6-tetrahydro-1,7-methanopyrido[1,2-e][1,4,5,8]oxatriazecine-8,10-dione

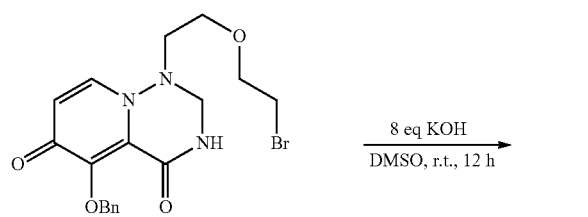

To a stirred yellow solution of 5-(benzyloxy)-1-(2-(2-bromoethoxy)ethyl)-2,3-dihydro-1H-pyrido[2,1-f][1,2,4]triazine-4,6-dione (40 mg, 0.095 mmol) in DMSO (1 mL) was added KOH (42.5 mg, 0.76 mmol) in one portion at 20° C., and then the mixture was stirred at 20° C. for 12 h. The mixture was poured into water (10 mL) and extracted with DCM (3×10 mL). The combined organic layers were dried over $Na_2SO_4$ and filtered. The filtrate was concentrated under reduced pressure and purified by preparative HPLC (Column: YMC-Actus Pro C18 150*30 mm, 5 μm; Conditions: water (0.1% TFA)/MeCN; begin B 10%, end B 40%; gradient time 11 min; 100% B hold time 1.1 min, flowrate 40 mL/min) to provide the title compound. $^1H$ NMR (400 MHz, $CDCl_3$) δ=7.52-7.51 (m, 2H), 7.33 (d, J=7.6 Hz, 1H), 7.28-7.21 (m, 3H), 6.36 (d, J=7.6 Hz, 1H), 5.45 (d, J=10.4 Hz, 1H), 5.13 (d, J=10.4 Hz, 1H), 4.78-4.67 (m, 2H), 4.12-4.00 (m, 1H), 3.96-3.92 (m, 2H), 3.84-3.82 (m, 1H), 3.56-3.55 (m, 1H), 3.41-3.40 (m, 1H), 3.24-3.23 (m, 1H), 2.98-2.97 (m, 1H). LRMS (M+H)$^+$: 342.2.

Step 3

9-(benzyloxy)-11-bromo-2,3,5,6-tetrahydro-1,7-methanopyrido[1,2-e][1,4,5,8]oxatriazecine-8,10-dione

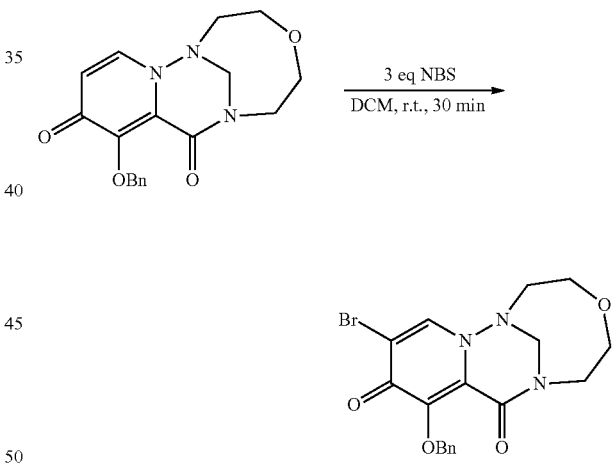

To a stirred solution of 9-(benzyloxy)-2,3,5,6-tetrahydro-1,7-methanopyrido[1,2-e][1,4,5,8]oxatriazecine-8,10-dione (25 mg, 0.073 mmol) in $CH_2Cl_2$ (1 mL) was added NBS (39.1 mg, 0.22 mmol) in one portion at 0° C. The mixture was stirred at 20° C. for 0.5 h. The mixture was purified by preparative TLC eluting with 5% MeOH in $CH_2Cl_2$ to provide the title compound. $^1H$ NMR (400 MHz, $CDCl_3$) δ=7.89 (s, 1H), 7.14 (d, J=7.6 Hz, 2H), 7.36-7.29 (m, 3H), 5.56 (d, J=10.4 Hz, 1H), 5.18 (d, J=10.4 Hz, 1H), 4.69-4.52 (m, 1H), 4.52-4.40 (m, 1H), 4.35 (d, J=14.5 Hz, 1H), 4.04-3.98 (m, 2H), 3.96-3.92 (m, 1H), 3.68-3.49 (m, 2H), 3.41-3.32 (m, 1H), 3.10-3.00 (m, 1H). LRMS (M+H)$^+$: 420.1.

Step 4

9-(benzyloxy)-N-(2,4-difluorobenzyl)-8,10-dioxo-2,
3,5,6,8,10-hexahydro-1,7-methanopyrido[1,2-e][1,4,
5,8]oxatriazecine-11-carboxamide Step 5

9-(benzyloxy)-N-(2,4-difluorobenzyl)-8,10-dioxo-2,
3,5,6,8,10-hexahydro-1,7-methanopyrido[1,2-e][1,4,
5,8]oxatriazecine-11-carboxamide

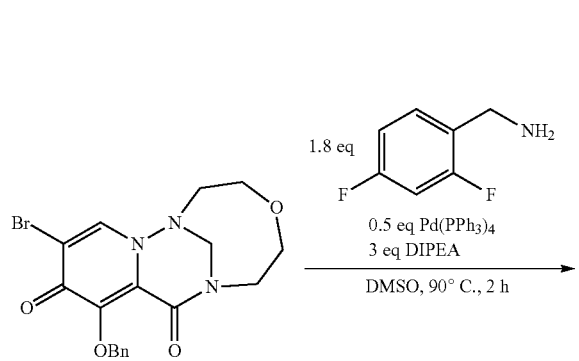

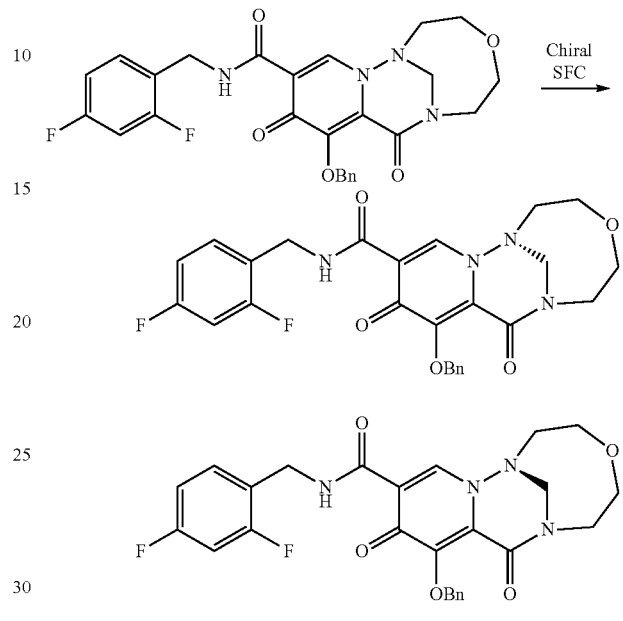

A mixture of 9-(benzyloxy)-11-bromo-2,3,5,6-tetrahydro-1,7-methanopyrido[1,2-e][1,4,5,8]oxatriazecine-8,10-dione (20 mg, 0.048 mmol), (2,4-difluorophenyl)methanamine (12.26 mg, 0.086 mmol), Pd(PPh$_3$)$_4$ (27.5 mg, 0.024 mmol) and DIEA (0.025 mL, 0.14 mmol) in DMSO (1 mL) was stirred under CO balloon (15 psi) at 90° C. for 2 h. The mixture was filtered and the filtrate was purified by preparative HPLC (Column: YMC-Actus Pro C18 150*30 mm, 5 µm; Conditions: water (0.1% TFA)/MeCN; begin B 30%, end B 60%; gradient time 11 min; 100% B hold time 1.1 min, flowrate 40 mL/min) to provide the title compound. LRMS (M+H)$^+$: 511.0.

Enantiomers were separated by preparative chiral SFC (Column: CHIRALCEL-AS 250*30 mm, 5 µm; Conditions: isocratic CO$_2$/EtOH (0.1% NH$_4$OH); begin B 40%, end B 40% (isocratic); flowrate 50 mL/min; peak 1 rt=3.59 min, peak 2 rt=4.36 min) to provide 9-(benzyloxy)-N-(2,4-difluorobenzyl)-8,10-dioxo-2,3,5,6,8,10-hexahydro-1,7-methanopyrido[1,2-e][1,4,5,8]-oxa-triazecine-11-carboxamide (PEAK 1, >99.9% ee) and 9-(benzyloxy)-N-(2,4-difluorobenzyl)-8,10-dioxo-2,3,5,6,8,10-hexahydro-1,7-methanopyrido[1,2-e][1,4,5,8]oxa-triazecine-11-carboxamide (PEAK 2, 99.02% ee). LRMS (M+H)$^+$: 511.0.

Step 6

N-(2,4-difluorobenzyl)-9-hydroxy-8,10-dioxo-2,3,5,
6,8,10-hexahydro-1,7-methanopyrido[1,2-e][1,4,5,8]
oxatriazecine-11-carboxamide

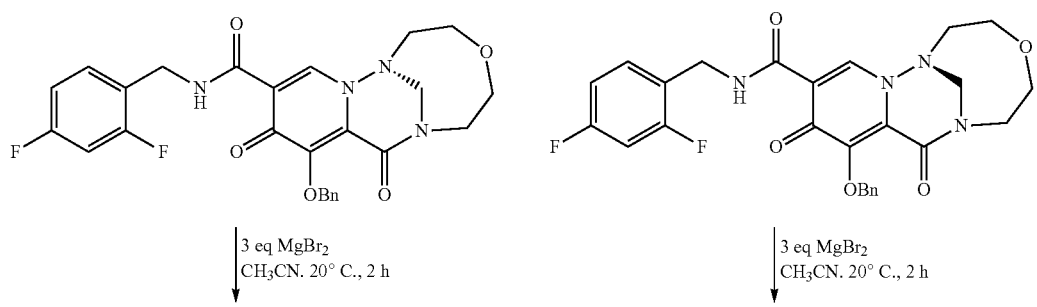

-continued

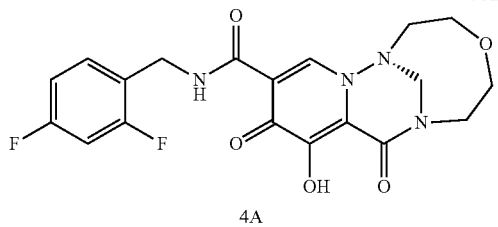

4A

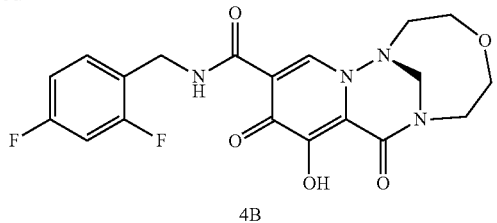

4B

To a solution of PEAK 1 of 9-(benzyloxy)-N-(2,4-difluorobenzyl)-8,10-dioxo-2,3,5,6,8,10-hexahydro-1,7-methanopyrido[1,2-e][1,4,5,8]oxatriazecine-11-carboxamide (8 mg, 0.016 mmol) in MeCN (1 mL) was added MgBr$_2$ (14.43 mg, 0.078 mmol), and the mixture was stirred at 40° C. for 2 h. The mixture was filtered and purified directly by reverse phase preparative HPLC (Column: Boston Green ODS 150*30 mm, 5 µm; Conditions: water (0.1% TFA)/MeCN; begin B 23%, end B 53%; gradient time 8 min; flowrate 30 mL/min) to provide 4A. $^1$H NMR (400 MHz, CDCl$_3$) δ=10.33 (s, 1H), 8.52 (s, 1H), 7.39-7.33 (m, 1H), 6.84-6.78 (m, 2H), 5.09 (d, J=13.6 Hz, 1H), 4.92 (d, J=13.6 Hz, 1H), 4.65-4.63 (m, 2H), 4.32-4.28 (m, 1H), 4.03-4.00 (m, 2H), 3.99-3.97 (m, 1H), 3.66-3.60 (m, 2H), 3.35-3.32 (m, 1H), 3.18-3.16 (m, 1H). LRMS (M+H)$^+$: 421.0. PEAK 2 of 9-(benzyloxy)-N-(2,4-difluorobenzyl)-8,10-dioxo-2,3,5,6,8,10-hexahydro-1,7-methanopyrido[1,2-e][1,4,5,8]-oxa-triazecine-11-carboxamide from the preceding chiral separation was subjected to the same reaction conditions to afford 4B. $^1$H NMR (400 MHz, CDCl$_3$) δ=10.32 (s, 1H), 8.51 (s, 1H), 7.38-7.32 (m, 1H), 6.83-6.77 (m, 2H), 5.08 (d, J=13.6 Hz, 1H), 4.91 (d, J=13.6 Hz, 1H), 4.64-4.63 (m, 2H), 4.31-4.27 (m, 1H), 4.02-3.99 (m, 2H), 3.98-3.97 (m, 1H), 3.65-3.59 (m, 2H), 3.35-3.31 (m, 1H), 3.17-3.15 (m, 1H). LRMS (M+H)$^+$: 421.0.

Example 5

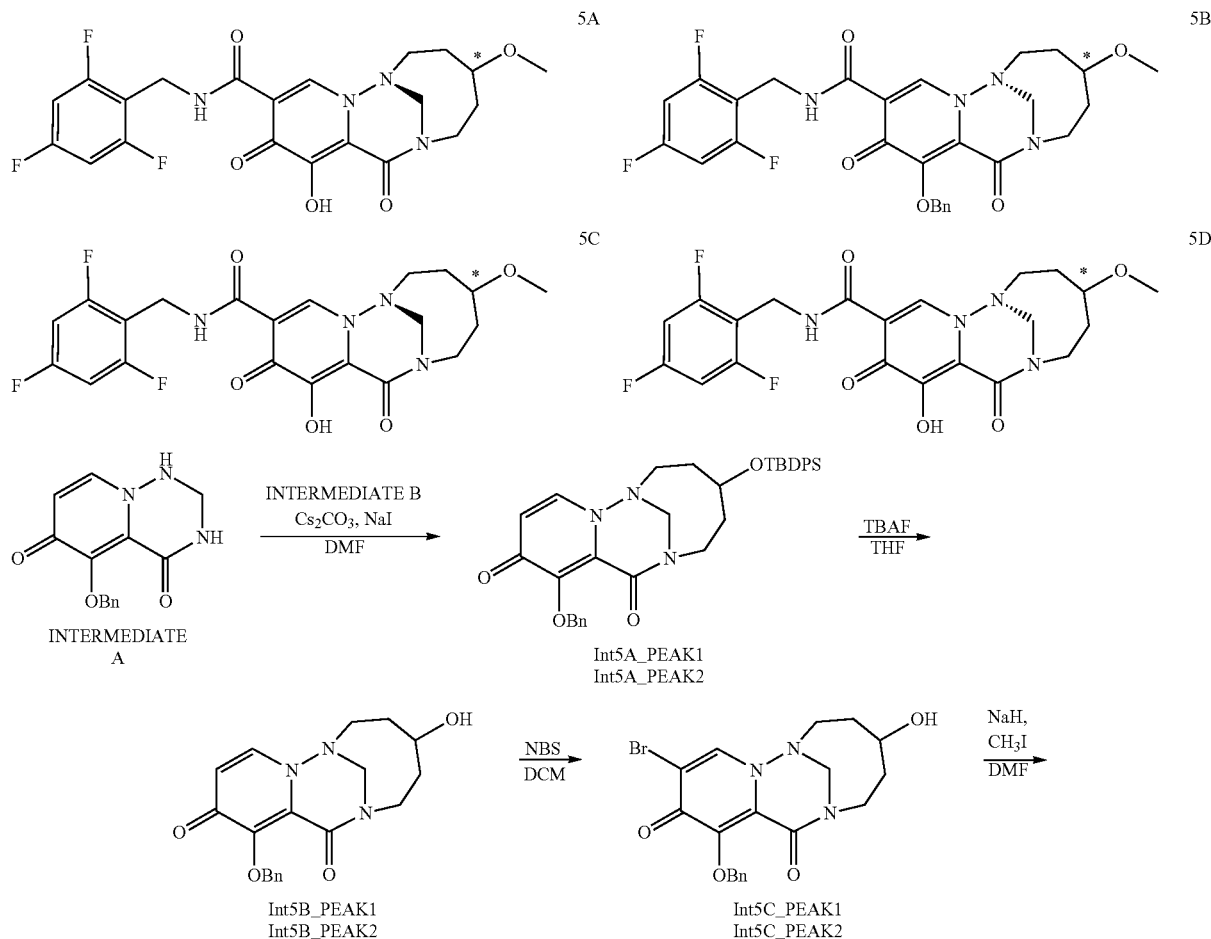

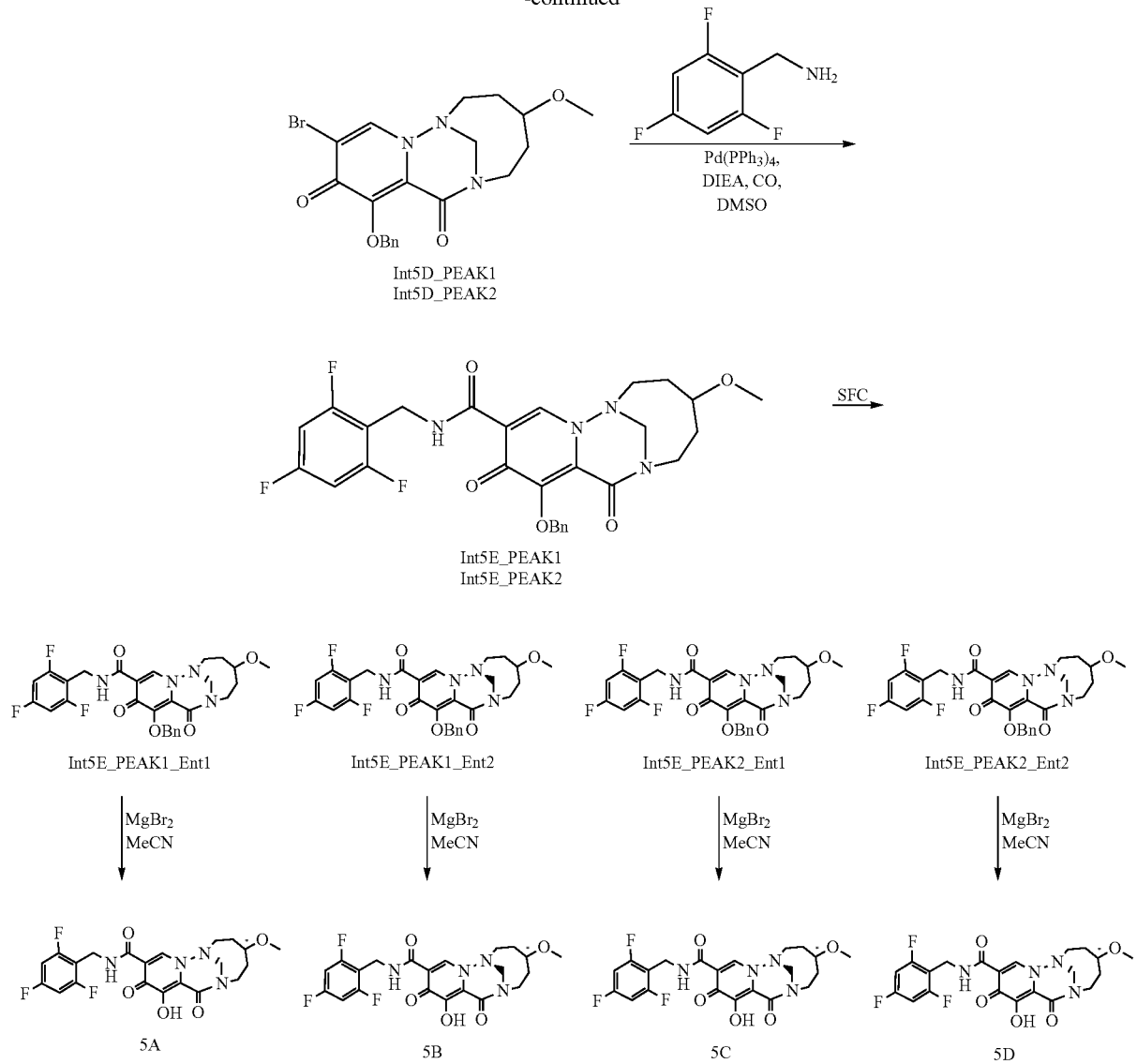

Step 1

9-(benzyloxy)-4-((tert-butyldiphenylsilyl)oxy)-3,4,5,6-tetrahydro-2H-1,7-methanopyrido[1,2-b][1,2,5]triazecine-8,10-dione

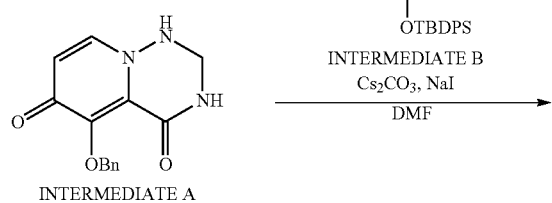

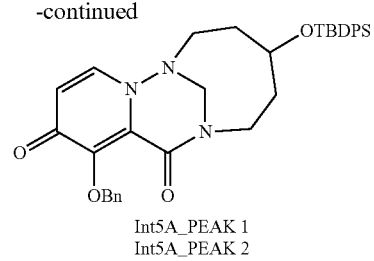

To a solution of INTERMEDIATE B (2.33 g, 4.81 mmol) in DMF (60 mL) was added INTERMEDIATE A (0.563 g, 2.075 mmol), cesium carbonate (2.70 g, 8.30 mmol) and sodium iodide (0.622 g, 4.15 mmol). The mixture was stirred at 40° C. under $N_2$ balloon for 13 h. LCMS showed the reaction was completed. Then the mixture was diluted with EtOAc (100 mL) and washed with water (3×100 mL), followed by brine (20 mL). The mixture was concentrated in vacuo and the crude product was purified by gradient elution on SiO₂ (ISCO, 120-g RediSep Gold column, 0 to 10% CH₂Cl₂/MeOH over 60 min, dry-loaded) to provide Int5A_PEAK1 (the firsted eluting isomer) and Int5A_PEAK2 (the second eluting isomer). Int5A_PEAK1: NMR (400 MHz, CDCl₃) δ=7.55-7.65 (m, 6H), 7.28-7.53 (m, 10H), 6.42 (d, J=7.9 Hz, 1H), 5.52 (d, J=10.5 Hz, 1H), 5.18 (d, J=10.1 Hz, 1H), 4.88 (br d, J=12.3 Hz, 1H), 4.67 (d, J=14.0 Hz, 1H), 4.25 (br s, 1H), 4.04-4.15 (m, 1H), 2.98-3.15 (m, 2H), 2.06-2.20 (m, 1H), 1.61 (br d, J=8.8 Hz, 4H), 1.13 (s, 9H). LRMS (M+H)⁺: 594.3. Int5A_PEAK2: ¹H NMR (400 MHz, CDCl₃) δ=7.58-7.70 (m, 7H), 7.29-7.42 (m, 9H), 6.37 (d, J=7.5 Hz, 1H), 5.52 (d, J=10.1 Hz, 1H), 5.20-5.29 (m, 2H), 3.49 (s, 3H), 3.15-3.30 (m, 2H), 2.66-2.76 (m, 1H), 2.01-2.18 (m, 2H), 1.79 (br t, J=10.1 Hz, 2H), 1.62 (br s, 3H), 1.07 (s, 9H). LRMS (M+H)⁺: 594.3.

Step 2

9-(benzyloxy)-4-hydroxy-3,4,5,6-tetrahydro-2H-1,7-methanopyrido[1,2-b][1,2,5]triazecine-8,10-dione

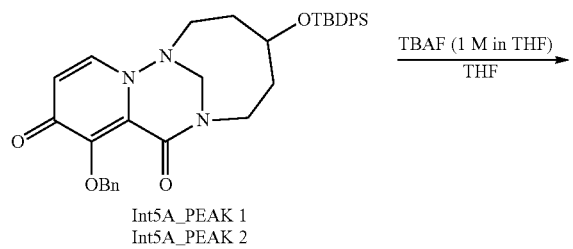

To a solution of Int5A_PEAK1 (1.66 g, 2.80 mmol) in THF (30 mL) was added tetrabutylammonium fluoride (6.99 mL, 6.99 mmol)(1 M in THF) under N₂, and then the mixture was stirred at 30° C. for 2 h. The mixture was concentrated in vacou. The crude product was purified by reverse phase preparative HPLC (column: Phenomenex Synergi Max-RP 150 mm*50 mm, 10 µm; Conditions: water (0.1% TFA)/MeCN; begin B 0%, end B 30%; gradient time 23 min; flowrate: 120 mL/min) to afford Int5B_PEAK1. ¹H NMR (400 MHz, CDCl₃) δ=7.76 (d, J=7.5 Hz, 1H), 7.50-7.58 (m, 2H), 7.26-7.37 (m, 4H), 5.44 (d, J=10.1 Hz, 1H), 5.23 (d, J=10.1 Hz, 1H), 4.11-4.26 (m, 1H), 3.72-3.91 (m, 1H), 3.14-3.20 (m, 4H), 1.53-1.61 (m, 4H). LRMS (M+H)⁺: 356.1. Int5A_PEAK2 was used to prepare Int5B_PEAK2 in an analogous manner. ¹H NMR (400 MHz, CDCl₃) δ=7.79 (br d, J=7.1 Hz, 1H), 7.52 (br d, J 6.2 Hz, 2H), 7.28-7.38 (m, 4H), 5.33-5.48 (m, 1H), 5.24 (br d, J=9.7 Hz, 1H), 4.40-4.50 (m, 2H), 4.07-4.17 (m, 1H), 3.97 (s, 4H), 3.12 (br s, 4H), 3.04 (br dd, J=8.4, 4.2 Hz, 3H), 2.17-2.31 (m, 1H), 1.85-2.04 (m, 3H), 1.57 (br s, 4H), 1.52-1.73 (m, 19H), 1.30-1.46 (m, 23H), 0.86-1.10 (m, 34H). LRMS (M+H)⁺: 356.1

Step 3

9-(benzyloxy)-4-hydroxy-3,4,5,6-tetrahydro-2H-1,7-methanopyrido[1,2-b][1,2,5]triazecine-8,10-dione

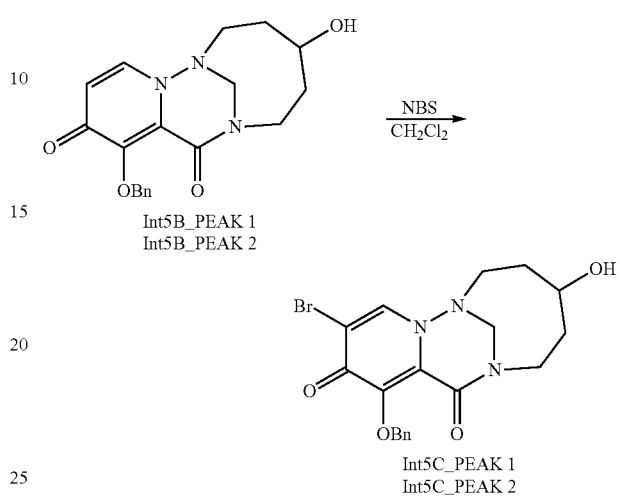

To a solution of Int5B_PEAK1 (2.2 g, 6.19 mmol) in CH₂Cl₂ (80 mL) was added NBS (2.20 g, 12.38 mmol), and the mixture was stirred at 30° C. for 2 h. The mixture was quenched with Na₂SO₃ solution (30 mL), extracted with EtOAc (3×10 mL), the organic layer was dried over Na₂SO₄ and filtered. The filtrate was concentrated in vacuo. The residue was purified by gradient elution on SiO₂ (ISCO, 4-g RediSep Gold column, 0 to 10% EtOAc/MeOH over 60 min, dry-loaded) to provide Int5C_PEAK1. ¹H NMR (400 MHz, CDCl₃) δ=7.87 (s, 1H), 7.62 (d, J=6.8 Hz, 2H), 7.30-7.41 (m, 3H), 5.50 (d, J=9.8 Hz, 1H), 5.20 (d, J=10.3 Hz, 1H), 4.18-4.25 (m, 2H), 3.57-3.79 (m, 1H), 3.43-3.57 (m, 1H), 3.04-3.20 (m, 2H), 2.88-2.99 (m, 1H), 1.74-2.01 (m, 4H). LRMS (M+H)⁺: 435.8. Int5B_PEAK2 was used to prepare Int5C_PEAK2 in an analogous manner. ¹H NMR (400 MHz, CDCl₃) δ=7.83 (s, 1H), 7.58-7.64 (m, 2H), 7.26-7.38 (m, 3H), 5.50 (d, J=9.9 Hz, 1H), 5.19 (d, J=9.9 Hz, 1H), 4.31 (d, J=14.3 Hz, 1H), 3.48 (s, 1H), 2.86 (ddd, J=14.3, 6.8, 4.2 Hz, 2H), 2.20-2.37 (m, 1H), 1.59 (br d, J=6.8 Hz, 2H). LRMS (M+H)⁺: 435.8

Step 4

9-(benzyloxy)-11-bromo-4-methoxy-3,4,5,6-tetrahydro-2H-1,7-methanopyrido[1,2-b][1,2,5]triazecine-8,10-dione

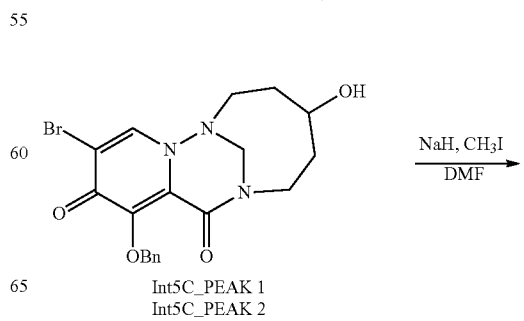

-continued

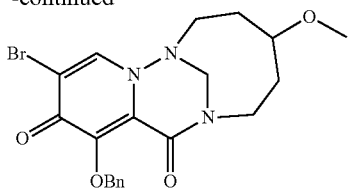

Int5D_PEAK 1
Int5D_PEAK 2

To a solution of Int5C_PEAK1 (70 mg, 0.16 mmol) in DMF (2 mL), cooled to 0° C., was added sodium hydride (12.89 mg, 0.32 mmol) and iodomethane (0.020 mL, 0.32 mmol). The mixture was stirred under $N_2$ for 2 h at 30° C. The mixture was quenched with 1N HCl (0.5 mL), diluted with MeOH (2 mL), and purified by reverse phase preparative HPLC (Column: Phenomenex Synergi C18 150 mm*30 mm, 4 μm; Conditions: water (0.1% TFA)/MeCN; begin B 24%, end B 47%; gradient time 10 min; flowrate: 25 mL/min) to afford Int5D_PEAK1. LRMS (M+H)$^+$: 448.1. Int5C_PEAK2 was used to prepare Int5D_PEAK2 in an analogous manner. LRMS (M+H)$^+$: 448.1.

Step 5: 9-(benzyloxy)-4-methoxy-8,10-dioxo-N-(2,4,6-trifluorobenzyl)-3,4,5,6,8,10-hexahydro-2H-1,7-methano-pyrido[1,2-b][1,2,5]triazecine-11-carboxamide

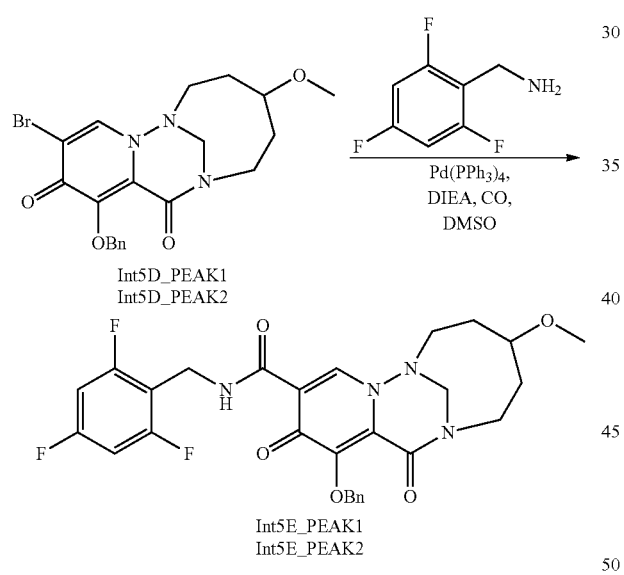

Int5D_PEAK1
Int5D_PEAK2

Int5E_PEAK1
Int5E_PEAK2

To a solution of Int5D_PEAK1 (42 mg, 0.094 mmol) in DMSO (1 mL) was added (2,4,6-trifluorophenyl)methanamine (0.023 mL, 0.19 mmol), N-ethyl-N-isopropylpropan-2-amine (0.082 mL, 0.47 mmol) and Pd(PPh$_3$)$_4$ (54.1 mg, 0.047 mmol), and the mixture was degassed under vacuum and purged with CO (3×). The mixture was stirred at 85° C. under balloon CO (15 psi) for 3 h. The mixture was diluted with EtOAc (10 mL), filtered, washed with water (3×10 mL), followed by brine (20 mL). The combined organic layers was dried over Na$_2$SO$_4$ and filtered. The filtrate was concentrated in vacuo, and the residue was purified by isocratic elution on SiO$_2$ (CH$_2$Cl$_2$:EtOAc=5:1) to provide crude product, which was further purified by reverse phase preparative HPLC (Column: YMC-Actus Pro C18 150 mm*30 mm, 4 μm; Conditions: water (0.1% TFA)/MeCN; begin B 43%, end B 73%; gradient time 10 min; flowrate: 40 mL/min) to afford Int5E_PEAK1. LRMS (M+H)$^+$: 557.2. Int5D_PEAK2 was used to prepare Int5E_PEAK2 in an analogous manner. LRMS (M+H)$^+$: 557.2

Step 6a 9-(benzyloxy)-4-methoxy-8,10-dioxo-N-(2,4,6-trifluorobenzy)-3,4,5,6,8,10-hexahydro-2H-1,7-methanopyrido[1,2-b][1,2,5]triazecine-11-carboxamide Enantiomers were separated by preparative chiral SFC (Column: CHIRALPAK-AS 250*50 mm, 10 μm; Conditions: isocratic CO$_2$/EtOH (0.1% NH$_4$OH); begin B 40%, end B 40% (isocratic); flowrate 45 mL/min) to provide Int5E_PEAK1_Ent1 (PEAK 1, >99.9% ee) and Int5E_PEAK1_Ent2 (PEAK 2, 99.02% ee). LRMS (M+H)$^+$: 557.2

Step 6b 9-(benzyloxy)-4-methoxy-8,10-dioxo-N-(2,4,6-trifluorobenzy)-3,4,5,6,8,10-hexahydro-2H-1,7-methanopyrido[1,2-b][1,2,5]triazecine-11-carboxamide

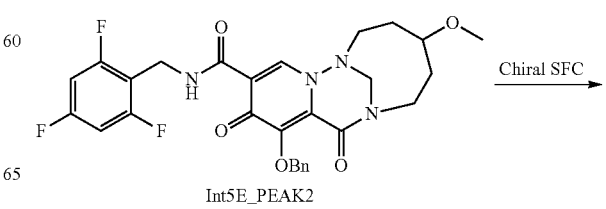

Int5E_PEAK2

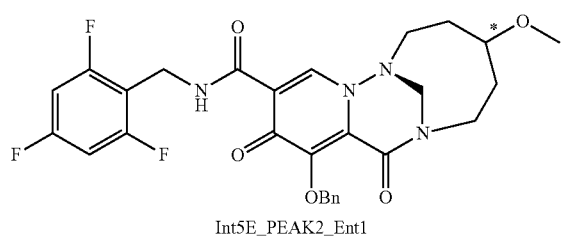

Int5E_PEAK2_Ent1

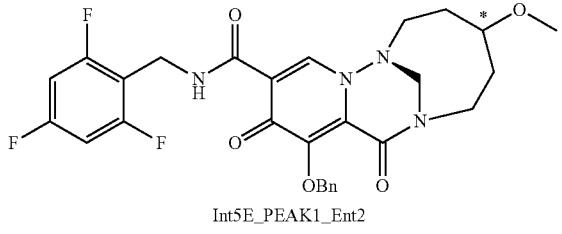

Int5E_PEAK1_Ent2

MgBr₂ | MeCN

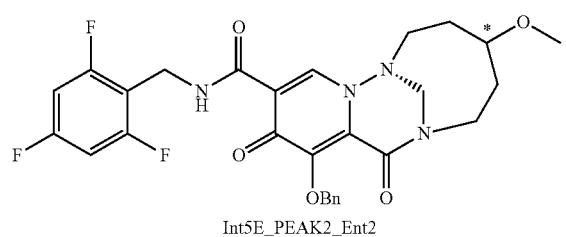

Int5E_PEAK2_Ent2

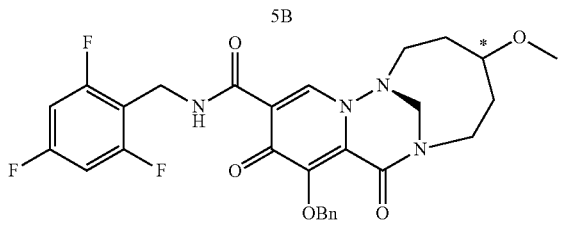

5B

Enantiomers were separated by preparative chiral SFC (Column: CHIRALPAK-AS 250*50 mm, 10 μm; Conditions: isocratic CO₂/EtOH (0.1% NH₄OH); begin B 40%, end B 40% (isocratic); flowrate 45 mL/min) to provide IntSE_PEAK2_Ent1 (PEAK 1, >99.9% ee) and Int5E_PEAK2_Ent2 (PEAK 2, 99.1% ee). LRMS (M+H)⁺: 557.2

Step 7

9-hydroxy-4-methoxy-8,10-dioxo-N-(2,4,6-trifluorobenzyl)-3,4,5,6,8,10-hexahydro-2H-1,7-methanopyrido[1,2-b][1,2,5]triazecine-11-carboxamide

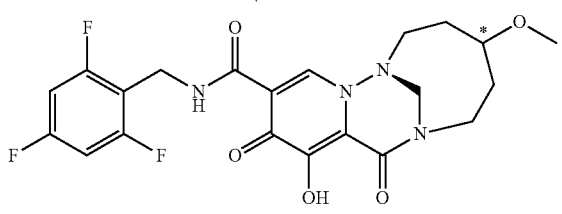

Int5E_PEAK2_Ent1

MgBr₂ | MeCN

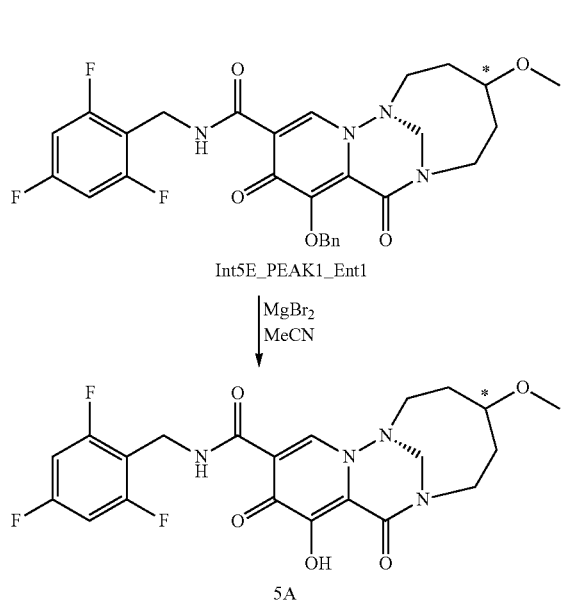

Int5E_PEAK1_Ent1

MgBr₂ | MeCN

5A

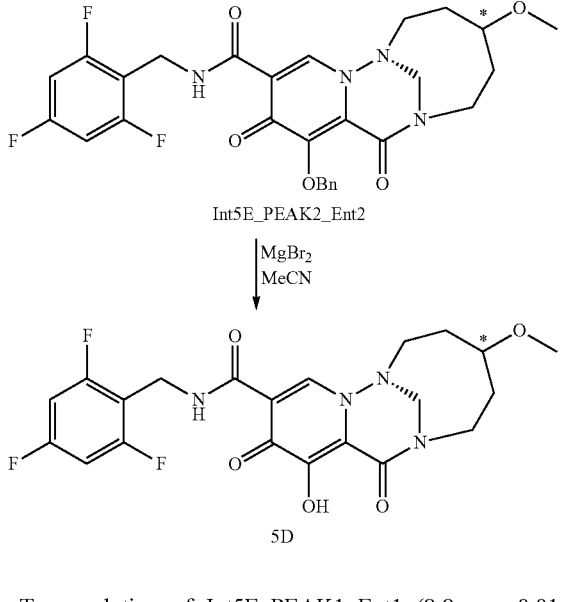

Int5E_PEAK2_Ent2

MgBr₂ | MeCN

5D

To a solution of Int5E_PEAK1_Ent1 (8.8 mg, 0.016 mmol) in MeCN (5 mL) was added magnesium bromide (29.1 mg, 0.16 mmol). The mixture was stirred at 30° C. for 2 h. The mixture was concentrated in vacuo. The residue was diluted with MeOH (3 mL), filtered, and the crude product was purified by reverse phase preparative HPLC (Column: Boston Green ODS 150 mm*30 mm, 5 μm; Conditions: water (0.1% TFA)/MeCN; begin B 40%, end B 70%; gradient time 10 min; flowrate: 25 mL/min) to afford 5A. $^1$H NMR (400 MHz, CDCl$_3$) δ=10.33 (br s, 1H), 8.46 (s, 1H), 6.65 (t, J=8.2 Hz, 2H), 4.79-4.92 (m, 2H), 4.57-4.74 (m, 2H), 4.22 (br d, J=14.1 Hz, 1H), 3.74-3.86 (m, 1H), 3.67 (br d, J=6.2 Hz, 1H), 3.41 (s, 3H), 3.03-3.21 (m, 2H), 1.93-2.21 (m, 4H). LRMS (M+H)$^+$: 467.0. Int5E_PEAK1_Ent2 was used to prepare 5B in an analogous manner. $^1$H NMR (400 MHz, CDCl$_3$) δ=10.34 (br s, 1H), 8.47 (s, 1H), 8.45-8.48 (m, 1H), 6.65 (t, J=8.0 Hz, 2H), 4.79-4.92 (m, 2H), 4.58-4.74 (m, 2H), 4.22 (br d, J=13.0 Hz, 1H), 3.75-3.85 (m, 1H), 3.68 (br s, 1H), 3.41 (s, 3H), 3.04-3.20 (m, 2H), 1.93-2.17 (m, 4H). LRMS (M+H)$^+$: 467.0. IntSE_PEAK2_Ent1 was used to prepare 5C in an analogous manner. $^1$H NMR (400 MHz, CDCl$_3$) δ=10.23 (br s, 1H), 8.40 (s, 1H), 6.59 (t, J 8.2 Hz, 2H), 4.54-4.74 (m, 3H), 4.38-4.53 (m, 2H), 3.18-3.29 (m, 6H), 2.94 (br d, J=13.7 Hz, 1H), 2.22 (br s, 2H), 1.94 (s, 2H). MS (M+H)$^+$: 467.0. Int5E_PEAK2_Ent2 was used to prepare 5D in an analogous manner. $^1$H NMR (400 MHz, CDCl$_3$) δ=10.30 (br s, 1H), 8.46 (s, 1H), 6.65 (t, J=8.0 Hz, 2H), 4.65 (br dd, J=10.1, 6.0 Hz, 2H), 4.45-4.58 (m, 2H), 3.30 (s, 6H), 3.00 (dt, J=14.3, 5.1 Hz, 1H), 2.23-2.37 (m, 2H), 1.93-2.05 (m, 2H). MS (M+H)$^+$: 467.0.

Example 6

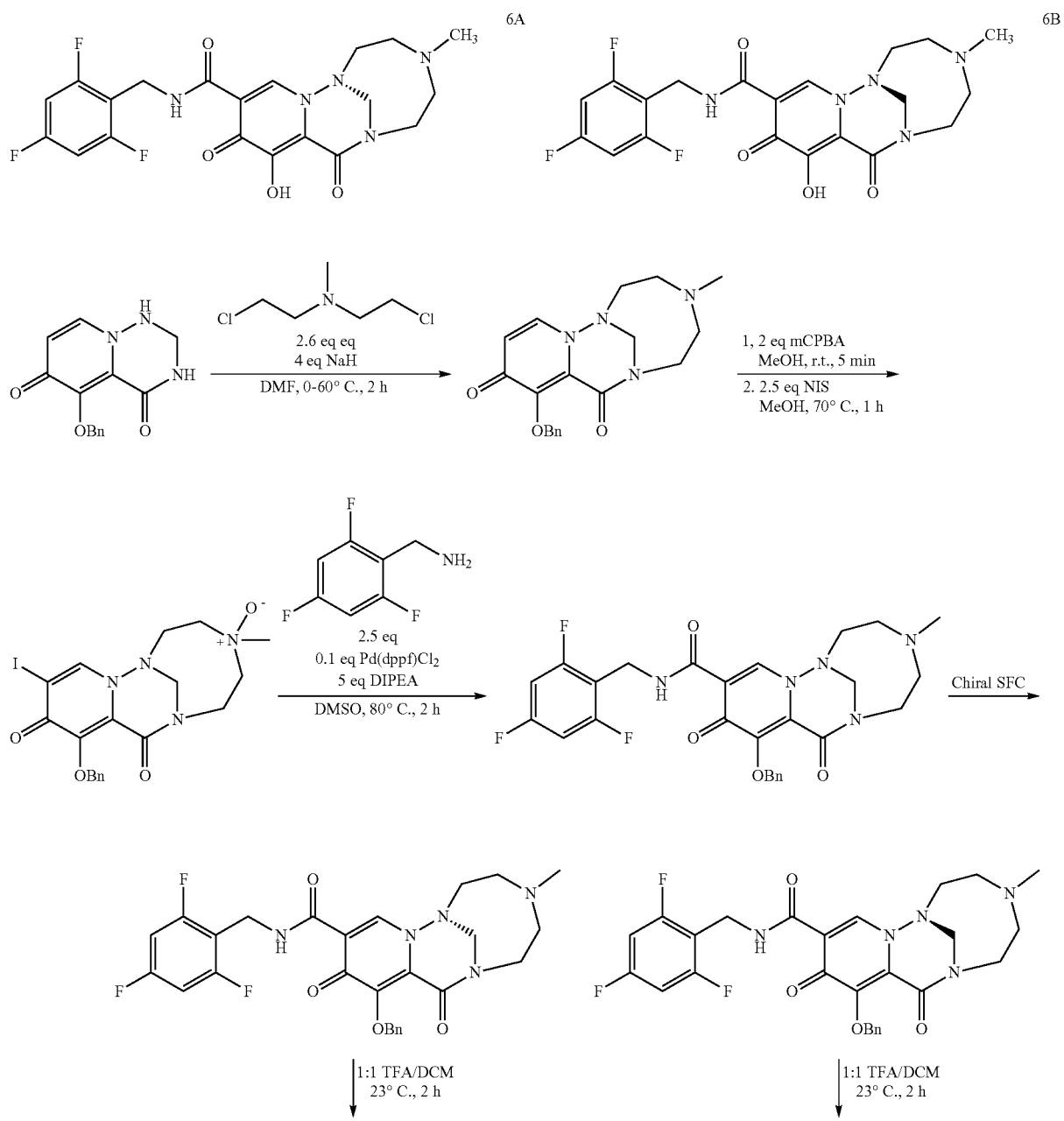

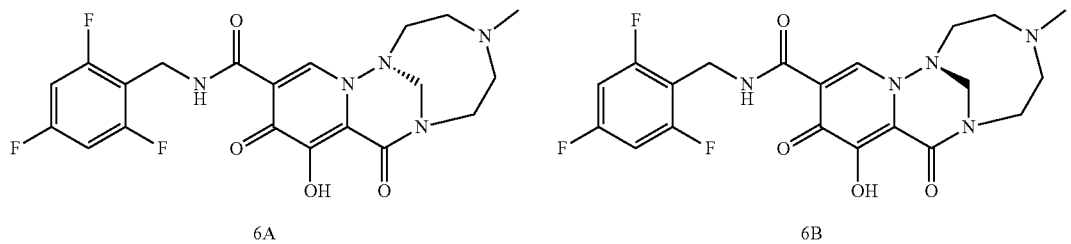

Step 1

9-(benzyloxy)-4-methyl-8,10-dioxo-3,4,5,6,8,10-hexahydro-2H-1,7-methanopyrido[1,2-b][1,2,5,8]tetrazecin-4-ium 2,2,2-trifluoroacetate

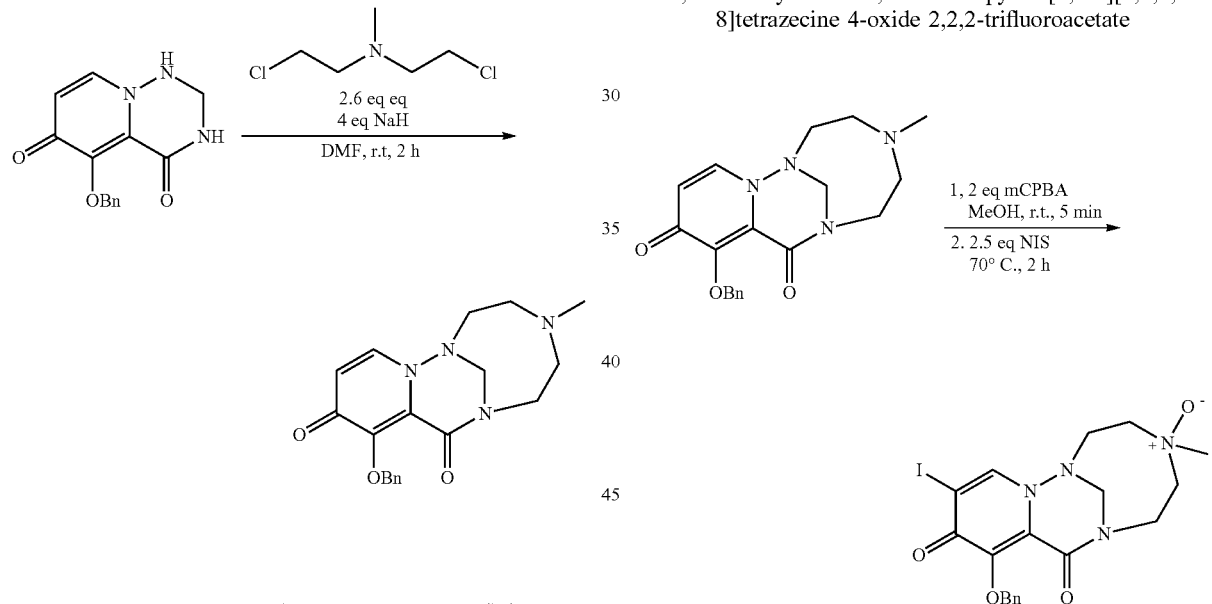

To INTERMEDIATE A (600 mg, 1.212 mmol) in DMF (15 mL) cooled to 0° C. was added sodium hydride (354 mg, 8.85 mmol), and the reaction mixture was stirred at the same temperature for 30 minutes. 2-chloro-N-(2-chloroethyl)-N-methylethanamine hydrochloride (1107 mg, 5.75 mmol) was added, and the reaction mixture was heated to 60° C. for 90 minutes. The mixture was cooled to 0° C. and sodium hydride (354 mg, 8.85 mmol) was added again, and the mixture heated to 60° C. after the addition for 20 minutes. The mixture was cooled to room temperature and quenched with 1:1 MeCN/water (3 mL) and then diluted with water (250 mL). The mixture in water was purified directly by preparative HPLC (Column: Phenomenex Luna C18 250*50 mm, 10 μm; Conditions: water (0.1% TFA)/MeCN; begin B 0%, end B 50%; gradient time 25 min; flowrate 90 mL/min) to provide the title compound. $^1$H NMR (500 MHz, CD$_3$OD) δ=7.98 (d, J=7 Hz, 1H), 7.52 (m, 2H), 7.37 (m, 3H), 6.64 (d, J=7 Hz, 1H), 5.34 (d, J=10.5 Hz, 1H), 5.21 (d, J=11 Hz, 1H), 4.98 (d, J=15.5 Hz, 1H), 4.88 (m, 1H), 4.02 (m, 1H), 3.75-3.69 (m, 2H), 3.47-3.33 (m, 3H), 3.01 (s, 3H). LRMS (M+H)$^+$: 355.4.

Step 2

9-(benzyloxy)-11-iodo-4-methyl-8,10-dioxo-3,4,5,6,8,10-hexahydro-2H-1,7-methanopyrido[1,2-b][1,2,5,8]tetrazecine 4-oxide 2,2,2-trifluoroacetate To a stirred solution of 9-(benzyloxy)-4-methyl-8,10-dioxo-3,4,5,6,8,10-hexahydro-2H-1,7-methanopyrido[1,2-b][1,2,5,8]tetrazecin-4-ium 2,2,2-trifluoroacetate (360 mg, 0.769 mmol) in MeOH (7.7 mL) was added mCPBA (265 mg, 1.54 mmol). The reaction mixture stirred for 5 minutes at room temperature. NIS (432 mg, 1.92 mmol) was then added in one portion, and the mixture was stirred at 70° C. for 2 h. The mixture was concentrated. The residue was dissolved in 1:1 MeCN/water (8 mL) and purified by preparative HPLC (Column: Waters XBridge C18 250*30 mm, 5 μm; Conditions: water (0.1% TFA)/MeCN; begin B 5%, end B 75%; gradient time 20 min; 100% B hold time 1.1 min, flowrate 50 mL/min) to afford the title compound. LRMS (M+H)$^+$: 497.4.

Step 3

9-(benzyloxy)-4-methyl-8,10-dioxo-N-(2,4,6-trifluorobenzyl)-3,4,5,6,8,10-hexahydro-2H-1,7-methanopyrido[1,2-b][1,2,5,8]tetrazecine-11-carboxamide

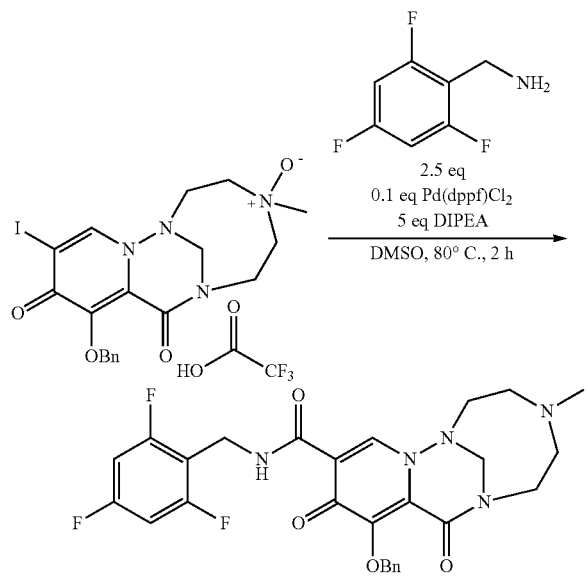

A mixture of 9-(benzyloxy)-11-iodo-4-methyl-8,10-dioxo-3,4,5,6,8,10-hexahydro-2H-1,7-methanopyrido[1,2-b][1,2,5,8]tetrazecine 4-oxide 2,2,2-trifluoroacetate (70 mg, 0.12 mmol), Pd(dppf)Cl$_2$ (8.4 mg, 0.011 mmol) and DIEA (0.074 mL, 0.57 mmol) in DMSO (1.1 mL) was stirred under CO balloon (15 psi) at 80° C. for 4 h. The mixture was diluted with DMSO (2 mL) and purified directly by preparative HPLC (Column: Waters Sunfire C18 150*30 mm, 5 μm; Conditions: water (0.1% TFA)/MeCN; begin B 15%, end B 85%; gradient time 20 min; 100% B hold time 1.1 min, flowrate 40 mL/min) and fractions containing product were neutralized with NaHCO$_3$ (aq), extracted with DCM (2×30 mL) and concentrated to afford the title compound. LRMS (M+H)$^+$: 542.5.

Step 4

9-(benzyloxy)-4-methyl-8,10-dioxo-N-(2,4,6-trifluorobenzyl)-3,4,5,6,8,10-hexahydro-2H-1,7-methanopyrido[1,2-b][1,2,5,8]tetrazecine-11-carboxamide

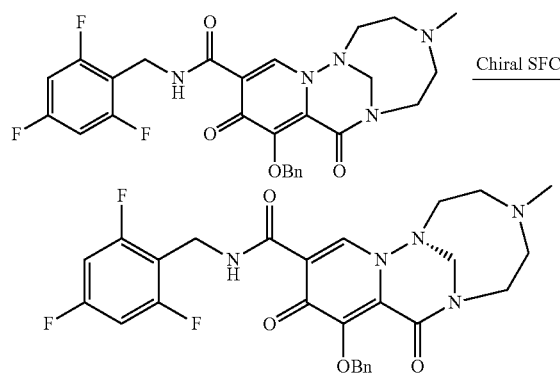

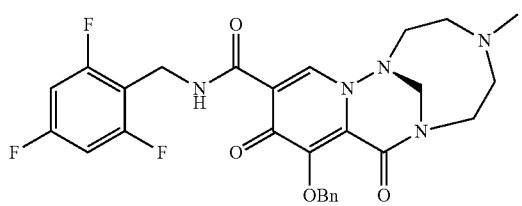

Enantiomers of 9-(benzyloxy)-4-methyl-8,10-dioxo-N-(2,4,6-trifluorobenzyl)-3,4,5,6,8,10-hexahydro-2H-1,7-methanopyrido[1,2-b][1,2,5,8]tetrazecine-11-carboxamide (29 mg, 0.054 mmol) were separated by preparative chiral SFC (Column: AS-H column 250*20 mm, 5 μm; Conditions: isocratic CO$_2$/MeOH (0.1% DEA); begin B 40%, end B 40% (isocratic); flowrate 60 mL/min; peak 1 rt=1.55 min, peak 2 rt=2.56 min) to provide (1R)-9-(benzyloxy)-4-methyl-8,10-dioxo-N-(2,4,6-trifluorobenzyl)-3,4,5,6,8,10-hexahydro-2H-1,7-methanopyrido[1,2-b][1,2,5,8]tetrazecine-11-carboxamide (PEAK 1, >99.5% ee) and (1S)-9-(benzyloxy)-4-methyl-8,10-dioxo-N-(2,4,6-trifluorobenzyl)-3,4,5,6,8,10-hexahydro-2H-1,7-methanopyrido[1,2-b][1,2,5,8]tetrazecine-11-carboxamide (PEAK 2, >99.5% ee). LRMS (M+H)$^+$: 542.5.

Step 5

9-hydroxy-4-methyl-8,10-dioxo-N-(2,4,6-trifluorobenzyl)-3,4,5,6,8,10-hexahydro-2H-1,7-methanopyrido[1,2-b][1,2,5,8]tetrazecine-11-carboxamide 2,2,2-trifluoroacetate

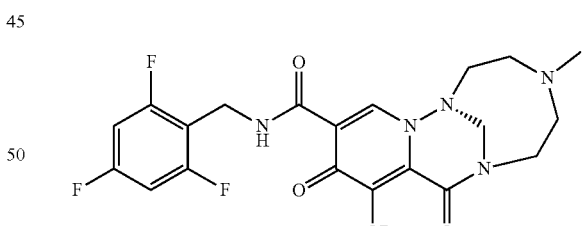

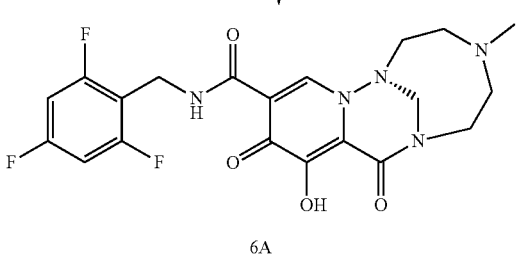

6A

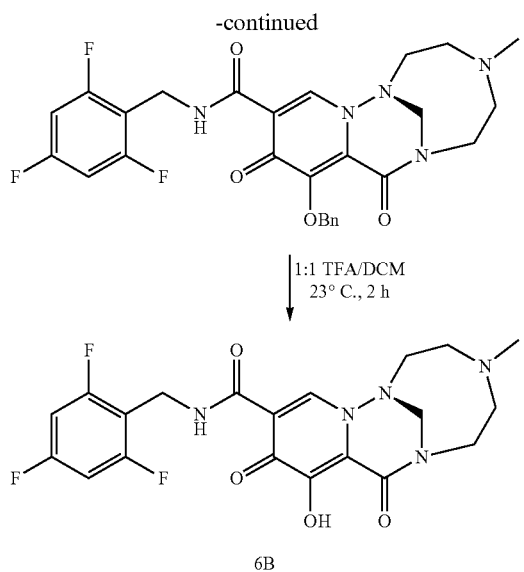

To a solution of PEAK 1 of 9-(benzyloxy)-4-methyl-8,10-dioxo-N-(2,4,6-trifluorobenzyl)-3,4,5,6,8,10-hexahydro-2H-1,7-methanopyrido[1,2-b][1,2,5,8]tetrazecine-11-carboxamide (10 mg, 0.018 mmol) in DCM (0.5 mL) was added TFA (0.5 mL, 6.49 mmol) and the mixture was stirred at 23° C. for 2 h. LCMS showed the reaction was completed. The mixture was concentrated. The residue was dissolved in 1:1 MeCN/water (2 mL) and purified by prep HPLC HPLC (Column: Waters Sunfire C18 150*30 mm, 5 μm; Conditions: water (0.1% TFA)/MeCN; begin B 15%, end B 85%; gradient time 20 min; 100% B hold time 1.1 min, flowrate 40 mL/min) to give 9-hydroxy-4-methyl-8,10-dioxo-N-(2,4,6-trifluorobenzyl)-3,4,5,6,8,10-hexahydro-2H-1,7-methanopyrido[1,2-b][1,2,5,8]tetrazecine-11-carboxamide 2,2,2-trifluoroacetate 6A. $^1$H NMR (600 MHz, CD$_3$OD) δ=10.43 (s, 1H), 8.47 (s, 1H), 6.89 (m, 2H), 5.14 (d, J=14.4 Hz, 1H), 5.03 (d, J=14.4 Hz, 1H), 4.65 (m, 2H), 4.58 (d, J=16.2 Hz, 1H), 3.99 (m, 1H), 3.76 (m, 1H), 3.63 (brs, 2H), 3.50 (m, 1H), 3.37 (m, 2H), 2.95 (s, 3H). LRMS (M+H)$^+$: 452.5. PEAK 2 of 9-(benzyloxy)-4-methyl-8,10-dioxo-N-(2,4,6-trifluorobenzyl)-3,4,5,6,8,10-hexahydro-2H-1,7-methanopyrido[1,2-b][1,2,5,8]tetrazecine-11-carboxamide (10 mg, 0.018 mmol) from the preceding chiral separation was subjected to the same reaction conditions to afford 6B. $^1$H NMR (600 MHz, CD$_3$OD) δ=10.43 (s, 1H), 8.47 (s, 1H), 6.89 (m, 2H), 5.14 (d, J=14.4 Hz, 1H), 5.03 (d, J=14.4 Hz, 1H), 4.65 (m, 2H), 4.58 (d, J=16.2 Hz, 1H), 3.99 (m, 1H), 3.76 (m, 1H), 3.63 (brs, 2H), 3.50 (m, 1H), 3.37 (m, 2H), 2.95 (s, 3H). LRMS (M+H)$^+$: 452.5.

Example 7

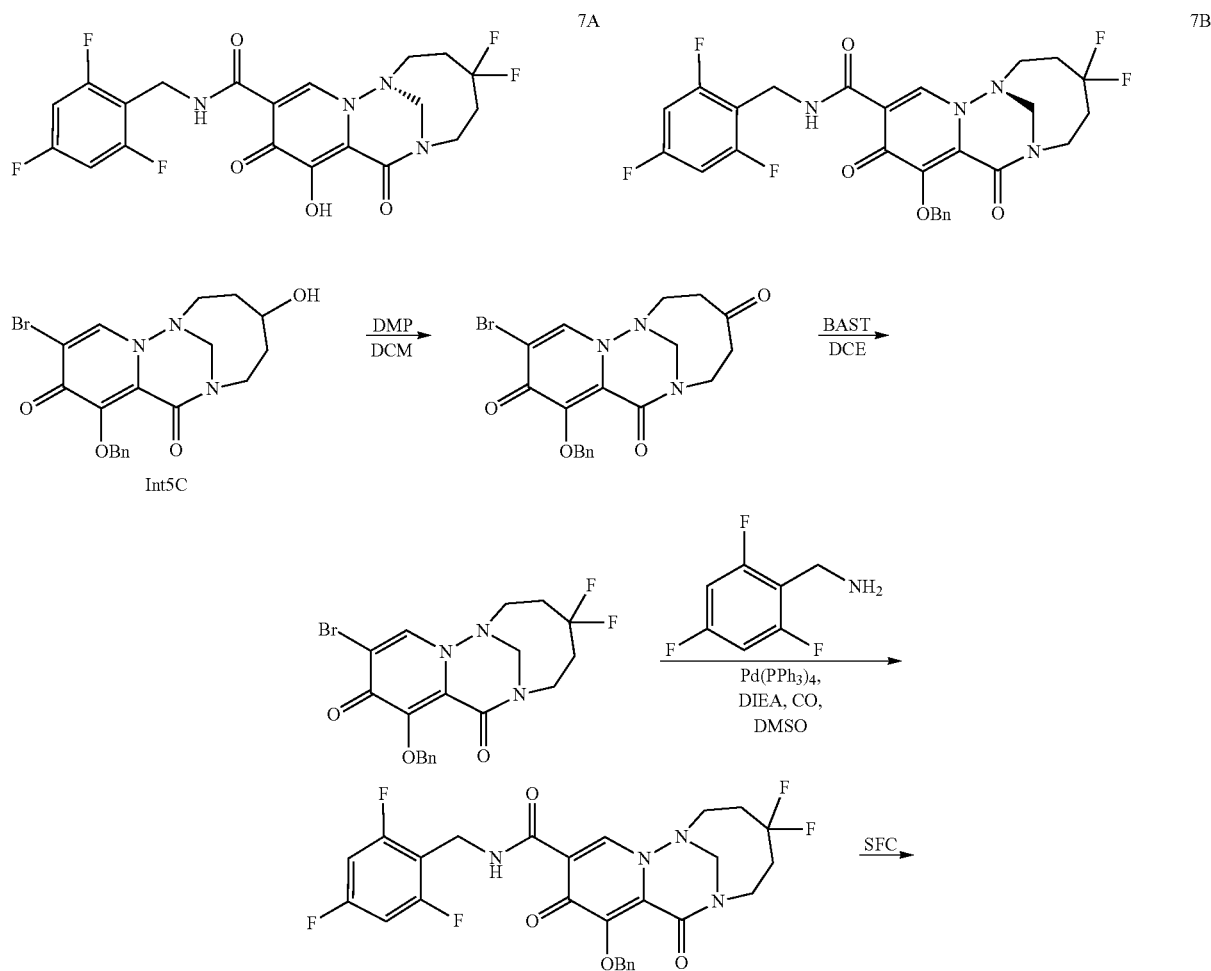

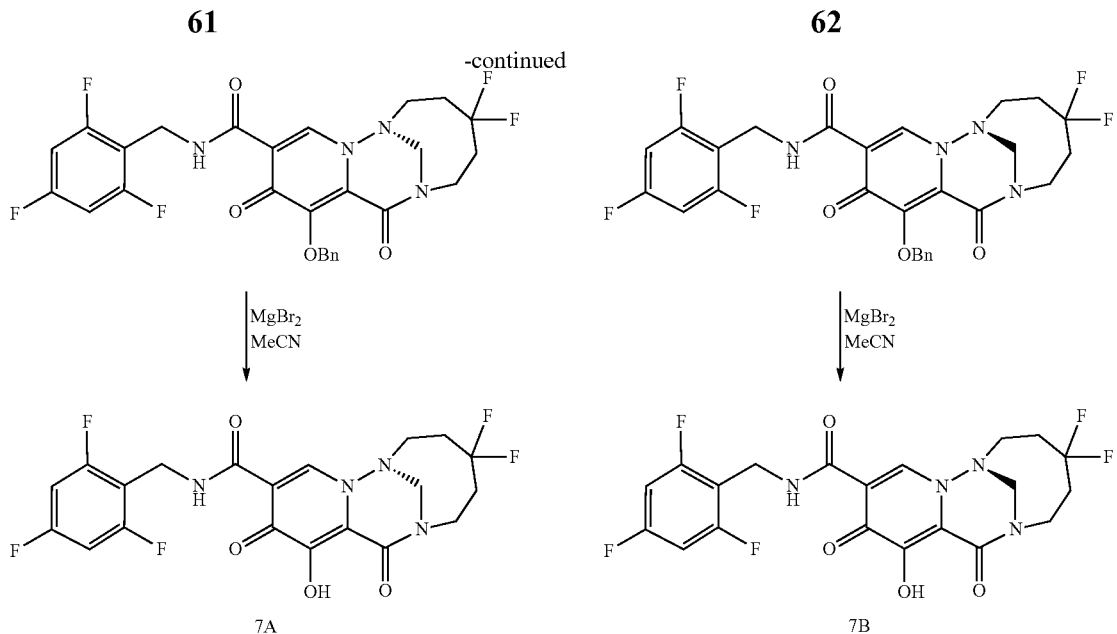

-continued 3.99 (d, J=15.2 Hz, 1H), 3.32-3.70 (m, 3H), 3.00 (br s, 1H), 2.72 (br s, 1H), 2.45 (br s, 1H), 2.28 (br d, J=11.0 Hz, 1H). MS (ESI) m/z: 432.1, 434.1 [M+H⁺].

Step 2

9-(benzyloxy)-11-bromo-4,4-difluoro-3,4,5,6-tetrahydro-2H-1,7-methanopyrido[1,2-b][1,2,5]triazecine-8,10-dione

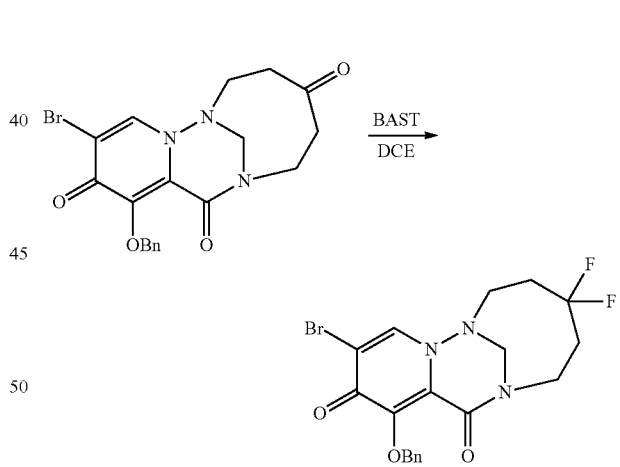

Step 1

9-(benzyloxy)-11-bromo-5,6-dihydro-2H-1,7-methanopyrido[1,2-b][1,2,5]triazecine-4,8,10(3H)-trione

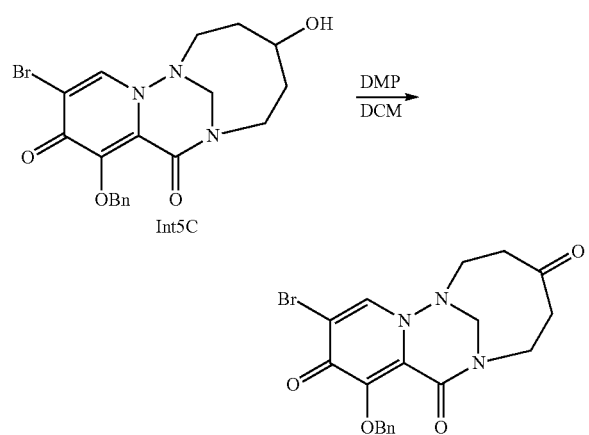

To a solution of 9-(benzyloxy)-11-bromo-4-hydroxy-3,4,5,6-tetrahydro-2H-1,7-methanopyrido[1,2-b][1,2,5]triazecine-8,10-dione (60 mg, 0.14 mmol) in CH₂Cl₂ (5 mL) was added DMP (58.6 mg, 0.14 mmol) at 0° C. The mixture was stirred at 0° C. for 2 h. LCMS showed starting material was consumed and the desired MS was observed, then the reaction was quenched with MeOH, diluted with water (5 mL) and extracted with DCM/MeOH (10/1) (20 mL×3). The combined organic phase was washed with brine (10 mL), dried over Na₂SO₄, filtered and concentrated in vacuo, the crude product was purified by normal phase chromatography (ISCO, 4 g RediSep Gold column, 0-10% EtOAc/MeOH, 30 min, dry loaded) to afford 9-(benzyloxy)-11-bromo-5,6-dihydro-2H-1,7-methanopyrido[1,2-b][1,2,5]triazecine-4,8,10(3H)-trione. ¹H NMR (CHLOROFORM-d) δ: 7.80 (s, 1H), 7.54 (br d, J=6.6 Hz, 2H), 7.20-7.32 (m, 3H), 5.52 (d, J=10.1 Hz, 1H), 5.17 (d, J=10.1 Hz, 1H), 4.53-4.72 (m, 2H), To a solution of 9-(benzyloxy)-11-bromo-5,6-dihydro-2H-1,7-methanopyrido[1,2-b][1,2,5]triazecine-4,8,10(3H)-trione (45 mg, 0.104 mmol) in ClCH₂CH₂Cl (5 mL) was added BAST (0.096 ml, 0.521 mmol) at 0° C., the mixture was stirred at 28° C. for 4 h, LCMS showed there was ~20% conversion, then the reaction mixture was stirred at 28° C. for another 24 h. LCMS showed there was ~80% conversion. The reaction was quenched with aq NaHCO₃ (0.5 mL) at 0° C., diluted with water (5 mL) and extracted with DCM/MeOH=10/1 (10 mL×3), the combined organic was dried over Na₂SO₄, filtered and concentrated in vacuo. The residue was purified by preparative TLC plate eluting with 6.7% MeOH/DCM to give 9-(benzyloxy)-11-bromo-4,4- difluoro-3,4,5,6-tetrahydro-2H-1,7-methanopyrido[1,2-b][1,2,5]triazecine-8,10-dione. ¹H NMR (CHLOROFORM-d) δ: 7.73-7.88 (m, 1H), 7.48-7.59 (m, 2H), 7.22-7.31 (m, 3H), 5.49 (d, J=10.1 Hz, 1H), 5.07-5.18 (m, 1H), 4.70-4.87 (m, 1H), 4.24-4.39 (m, 2H), 3.25-3.74 (m, 3H), 3.01 (ddd, J=14.4, 10.7, 3.7 Hz, 1H), 1.98-2.41 (m, 3H). MS (ESI) m/z: 454.1, 456.1 [M+H⁺].

Step 3

9-(benzyloxy)-4,4-difluoro-8,10-dioxo-N-(2,4,6-trifluorobenzyl)-3,4,5,6,8,10-hexahydro-2H-1,7-methanopyrido[1,2-b][1,2,5]triazecine-11-carboxamide To a solution of 9-(benzyloxy)-11-bromo-4,4-difluoro-3,4,5,6-tetrahydro-2H-1,7-methanopyrido[1,2-b][1,2,5]triazecine-8,10-dione (20 mg, 0.044 mmol) in DMSO (2 mL) was added (2,4,6-trifluorophenyl)methanamine (21.28 mg, 0.132 mmol), Pd(Ph₃P)₄ (5.09 mg, 4.40 μmol) and DIEA (0.038 mL, 0.22 mmol), then the reaction mixture was degassed and purged with CO for three times. The mixture was stirred at 85° C. for 2 h under CO balloon. LCMS showed the reaction was completed. The reaction mixture was diluted with EtOAc (10 mL), filtered and washed with HCl (5 mL, 1M/L). The HCl layers was extracted with EtOAc (10 mL×3), the combined the organic layer was dried over Na₂SO₄ and filtered, concentrated in vacuo, the residue was purified by preparative TLC plate eluting with 100% EtOAc to afford 9-(benzyloxy)-4,4-difluoro-8,10-dioxo-N-(2,4,6-trifluorobenzyl)-3,4,5,6,8,10-hexahydro-2H-1,7-methanopyrido[1,2-b][1,2,5]triazecine-11-carboxamide. ¹H NMR (CHLOROFORM-d) δ: 10.24 (br s, 1H), 8.43-8.57 (m, 1H), 7.43-7.57 (m, 2H), 7.23-7.35 (m, 3H), 6.59-6.64 (m, 1H), 6.59 (q, J=8.2 Hz, 2H), 5.44 (d, J=10.4 Hz, 1H), 5.16 (d, J=9.9 Hz, 1H), 4.52-4.80 (m, 3H), 4.24-4.38 (m, 3H), 3.65 (s, 1H), 3.33-3.52 (m, 1H), 3.04 (br d, J=11.5 Hz, 1H), 2.02-2.75 (m, 2H). MS (ESI) m/z: 563.0 [M+H⁺].

Step 4

9-(benzyloxy)-4,4-difluoro-8,10-dioxo-N-(2,4,6-trifluorobenzyl)-3,4,5,6,8,10-hexahydro-2H-1,7-methanopyrido[1,2-b][1,2,5]triazecine-11-carboxamide

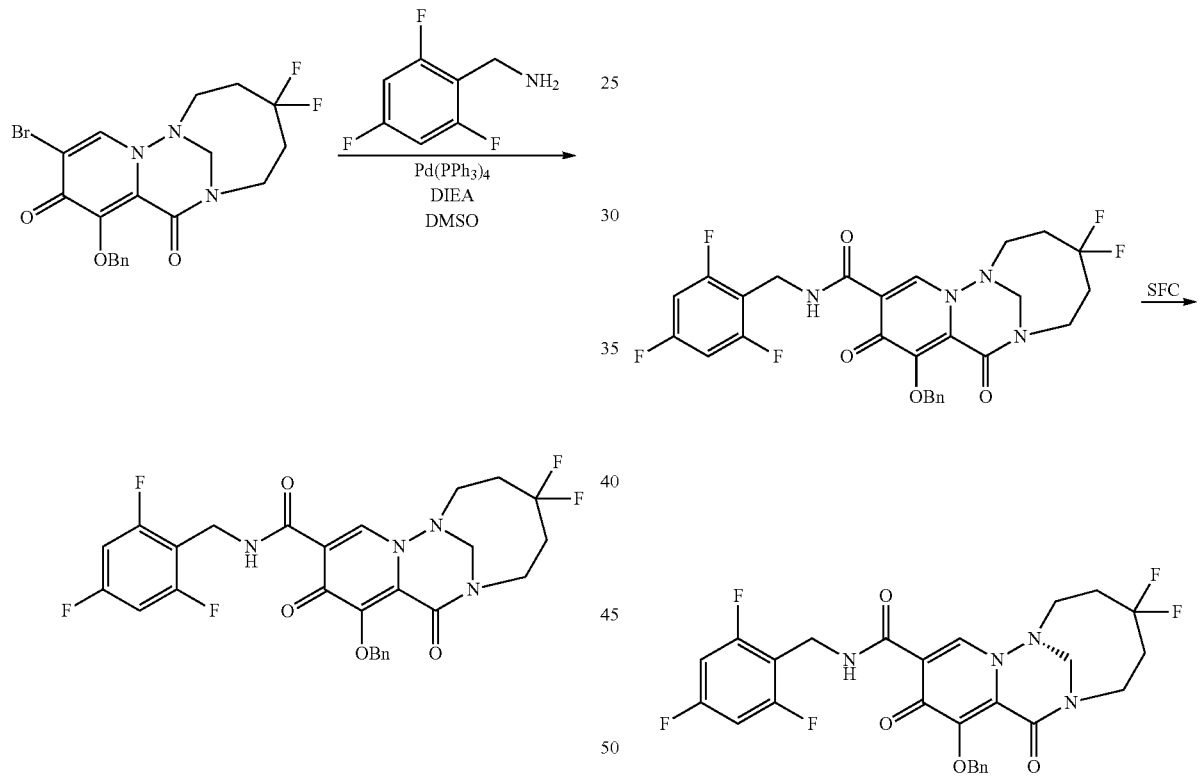

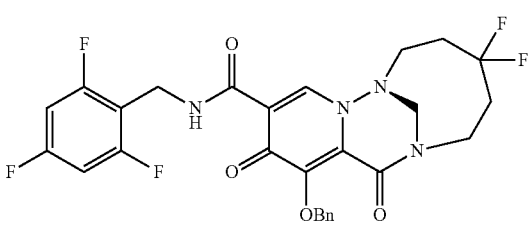

Resolution to the enantiomer 9-(benzyloxy)-4,4-difluoro-8,10-dioxo-N-(2,4,6-trifluorobenzyl)-3,4,5,6,8,10-hexahydro-2H-1,7-methanopyrido[1,2-b][1,2,5]triazecine-11-carboxamide (20 mg, 0.036 mmol) was accomplished with SFC (Column: DAICEL CHIRALPAK AS (250 mm*50 mm, 10 μm); Mobile phase: 35% Base-EtOH (contained 0.1% NH$_3$H$_2$O) in CO$_2$; Flow rate: 50 mL/min; injection: 150) to give 9-(benzyloxy)-4,4-difluoro-8,10-dioxo-N-(2,4,6-trifluorobenzyl)-3,4,5,6,8,10-hexahydro-2H-1,7-methanopyrido[1,2-b][1,2,5]triazecine-11-carboxamide as the first eluting isomer (PEAK 1) and 9-(benzyloxy)-4,4-difluoro-8,10-dioxo-N-(2,4,6-trifluorobenzyl)-3,4,5,6,8,10-hexahydro-2H-1,7-methanopyrido[1,2-b][1,2,5]triazecine-11-carboxamide as the second eluting isomer (PEAK 2). MS (ESI) m/z: 563.0 [M+H$^+$].

Step 5

9-(benzyloxy)-4,4-difluoro-8,10-dioxo-N-(2,4,6-trifluorobenzyl)-3,4,5,6,8,10-hexahydro-2H-1,7-methanopyrido[1,2-b][1,2,5]triazecine-11-carboxamide

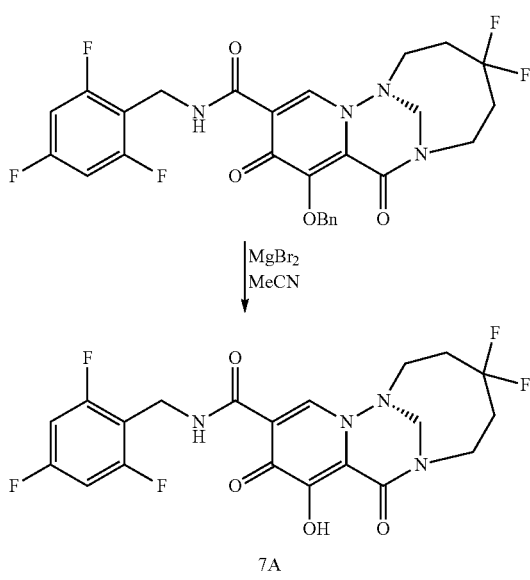

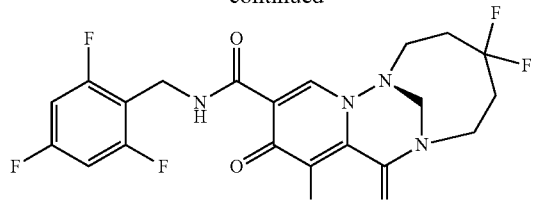

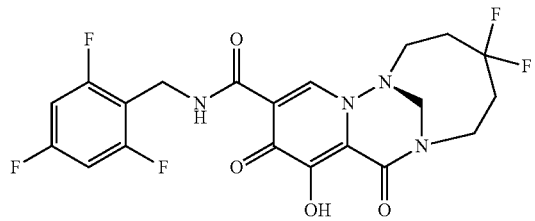

7B

To a solution of PEAK 1 of 9-(benzyloxy)-4,4-difluoro-8,10-dioxo-N-(2,4,6-trifluorobenzyl)-3,4,5,6,8,10-hexahydro-2H-1,7-methanopyrido[1,2-b][1,2,5]triazecine-11-carboxamide (9 mg, 0.016 mmol) in MeCN (3 mL) was added magnesium bromide (14.73 mg, 0.080 mmol). The mixture was stirred at 22° C. for 2 h. LCMS showed the reaction was completed. The mixture was concentrated in vacuo and the residue was diluted with MeOH (2 mL), filtrated, the crude product was purified by preparative HPLC (column: Boston Green ODS 150 mm*30 mm, 5 μm; condition: water (0.1% TFA)-MeCN begin B 37, end B 67; gradient time (min): 10; 100% B Hold time (min): 2; FlowRate (mL/min)L 25) to give 4,4-difluoro-9-hydroxy-8,10-dioxo-N-(2,4,6-trifluorobenzyl)-3,4,5,6,8,10-hexahydro-2H-1,7-methanopyrido[1,2-b][1,2,5]triazecine-11-carboxamide 7A and which was Co-evaporated with toluene to afford the free base. $^1$H NMR (CHLOROFORM-d) δ: 10.11 (br s, 1H), 8.42 (s, 1H), 6.59 (t, J=8.2 Hz, 2H), 4.90 (br d, J=14.1 Hz, 1H), 4.52-4.68 (m, 2H), 4.25-4.46 (m, 2H), 3.72 (br d, J=11.7 Hz, 1H), 3.28-3.47 (m, 1H), 3.03-3.20 (m, 1H), 2.50-2.75 (m, 1H), 2.02-2.38 (m, 3H). MS (ESI) m/z: 472.9 [M+H$^+$]PEAK 2 of 9-(benzyloxy)-4,4-difluoro-8,10-dioxo-N-(2,4,6-trifluorobenzyl)-3,4,5,6,8,10-hexahydro-2H-1,7-methanopyrido[1,2-b][1,2,5]triazecine-11-carboxamide (9 mg, 0.016 mmol) from the preceding chiral separation was subjected to the same reaction conditions to afford 7B. $^1$H NMR (CHLOROFORM-d) δ: 10.12 (br s, 1H), 8.42 (s, 1H), 6.59 (t, J=8.0 Hz, 2H), 4.90 (br d, J=13.5 Hz, 1H), 4.52-4.69 (m, 2H), 4.34-4.48 (m, 2H), 3.74 (br s, 1H), 3.39 (br s, 1H), 3.14 (br t, J=10.7 Hz, 1H), 2.49-2.77 (m, 1H), 2.06-2.31 (m, 3H). MS (ESI) m/z: 472.9 [M+H$^+$]

The compounds in Table 1 were prepared in an analogous fashion to that described in the examples above. The isomers were separated by either preparative HPLC, preparative chiral HPLC, or preparative chiral SFC. Assigned stereochemistry is done so by analogy to compounds 1A and 1B. Unknown and unassigned strerochemistry is denoted by an asterisk (*).

TABLE 1

| Ex. No. | Structure | Preparative Method(s) Used | LRMS (ESI) [M + 1]+ |
|---|---|---|---|
| 8A | 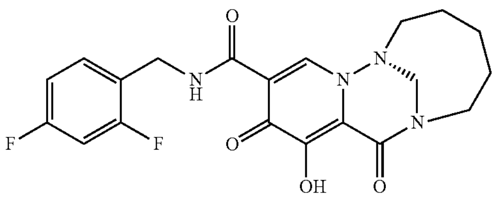 | Example 1 | 419 |
| 8B | 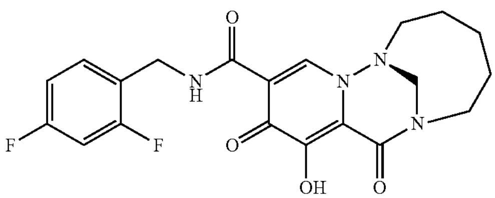 | Example 1 | 419 |
| 9A | 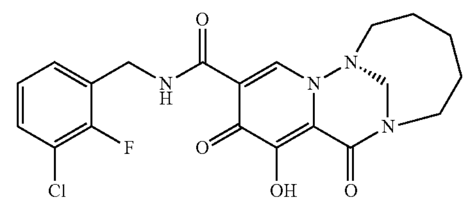 | Example 1 | 435 |
| 9B | 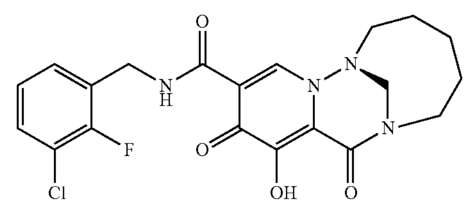 | Example 1 | 435 |
| 10A | 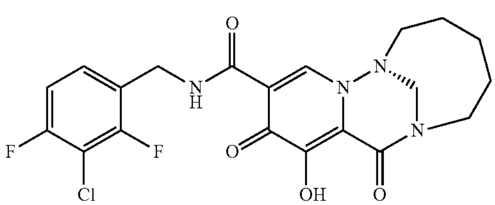 | Example 1 | 453 |
| 10B | 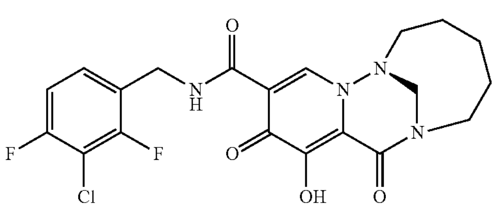 | Example 1 | 453 |
| 11A | 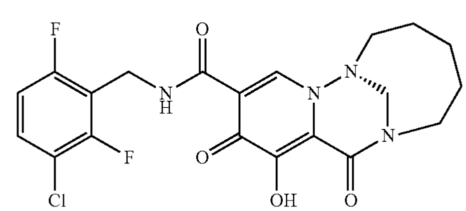 | Example 1 | 453 |

TABLE 1-continued

| Ex. No. | Structure | Preparative Method(s) Used | LRMS (ESI) [M + 1]+ |
|---|---|---|---|
| 11B | 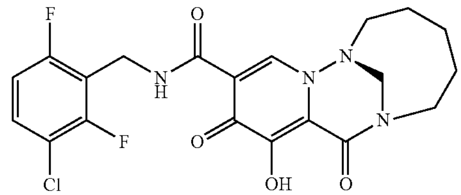 | Example 1 | 453 |
| 12A | 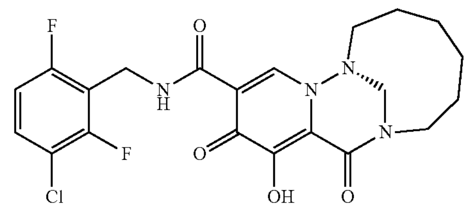 | Example 3 | 467 |
| 12B | 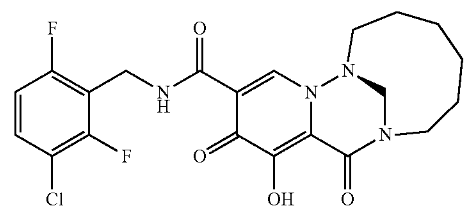 | Example 3 | 467 |
| 13A | 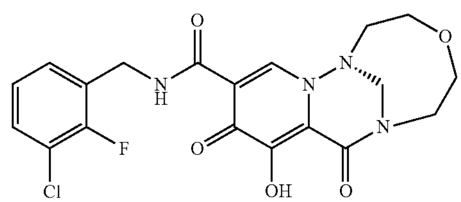 | Example 4 | 437 |
| 13B | 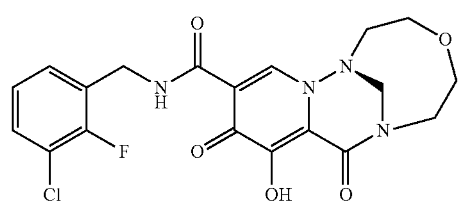 | Example 4 | 437 |
| 14A | 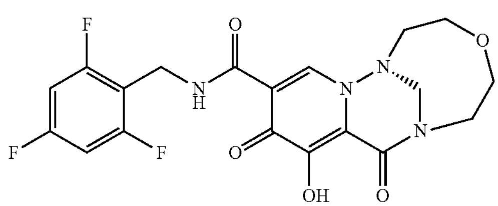 | Example 4 | 439 |
| 14B | 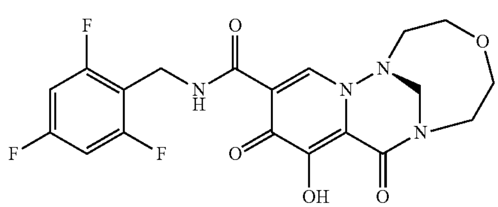 | Example 4 | 439 |

TABLE 1-continued

| Ex. No. | Structure | Preparative Method(s) Used | LRMS (ESI) [M + 1]+ |
|---|---|---|---|
| 15A | 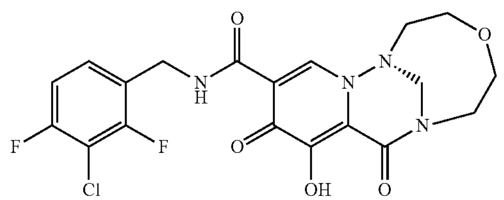 | Example 4 | 455 |
| 15B | 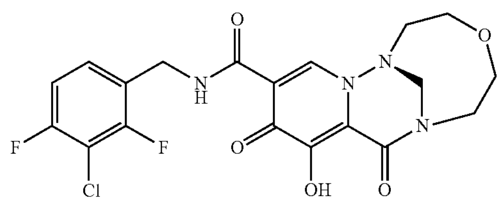 | Example 4 | 455 |
| 16A | 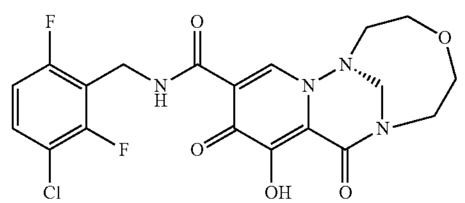 | Example 4 | 455 |
| 16B | 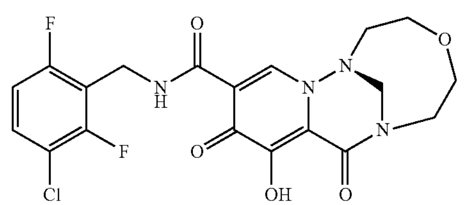 | Example 4 | 455 |
| 17A | 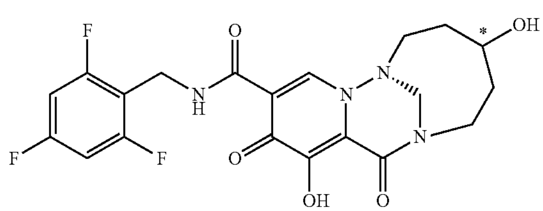 | Example 5 | 453 |
| 17B | 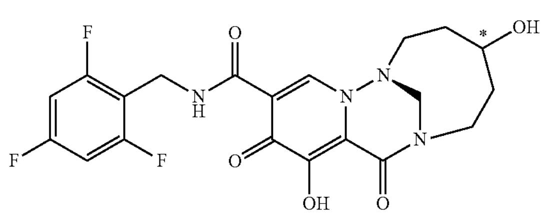 | Example 5 | 453 |
| 17C | 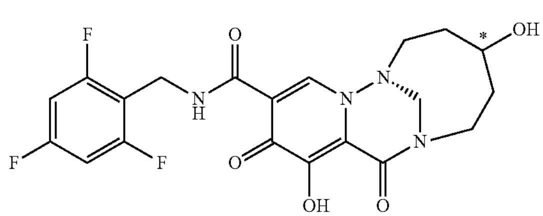 | Example 5 | 453 |

TABLE 1-continued

| Ex. No. | Structure | Preparative Method(s) Used | LRMS (ESI) [M + 1]+ |
|---|---|---|---|
| 17D | 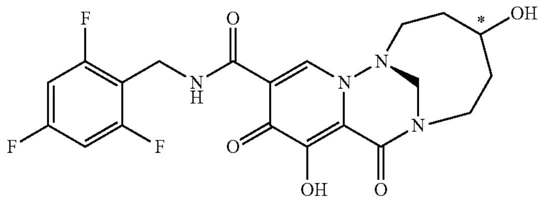 | Example 5 | 453 |
| 18A | 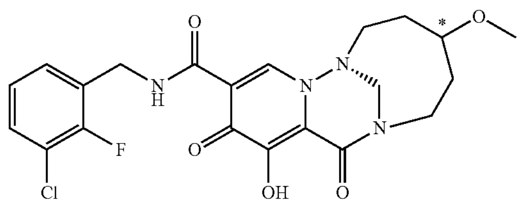 | Example 5 | 465 |
| 18B | 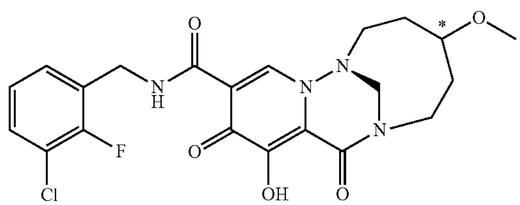 | Example 5 | 465 |
| 18C | 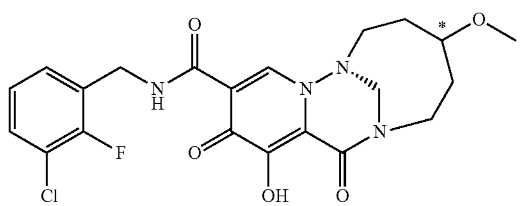 | Example 5 | 465 |
| 18D | 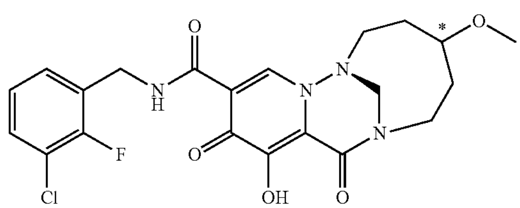 | Example 5 | 465 |
| 19A | 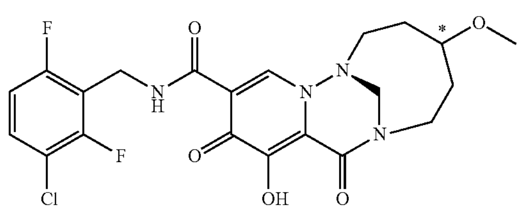 | Example 5 | 483 |
| 19B | 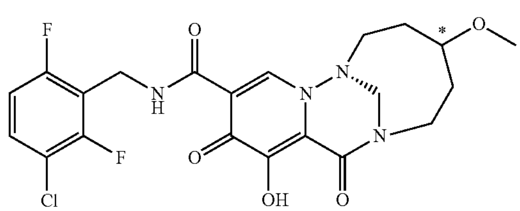 | Example 5 | 483 |

TABLE 1-continued

| Ex. No. | Structure | Preparative Method(s) Used | LRMS (ESI) [M + 1]+ |
|---|---|---|---|
| 19C | 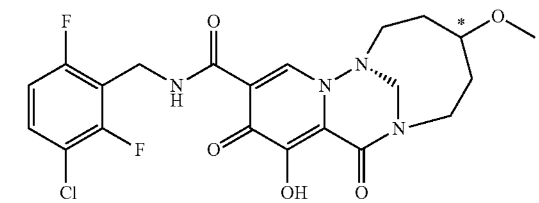 | Example 5 | 483 |
| 19D | 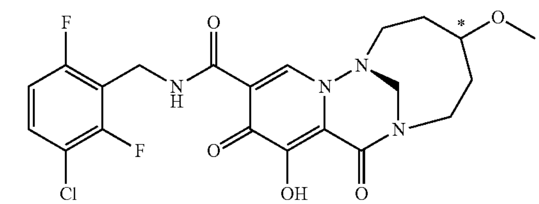 | Example 5 | 483 |
| 20A | 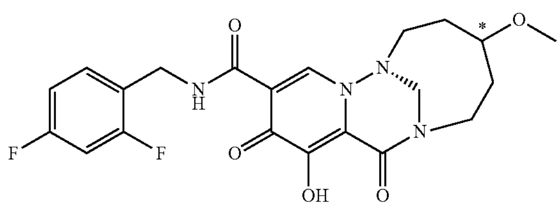 | Example 5 | 449 |
| 20B | 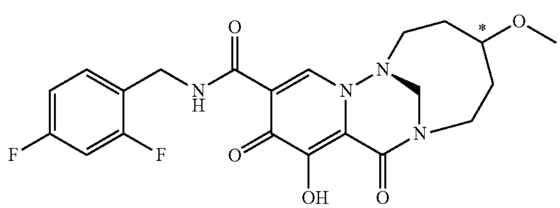 | Example 5 | 449 |
| 20C | 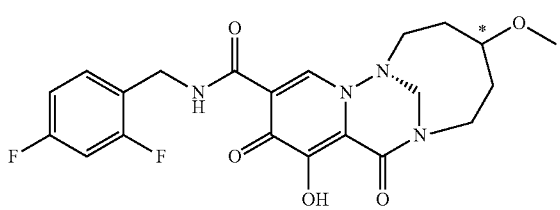 | Example 5 | 449 |
| 20D | 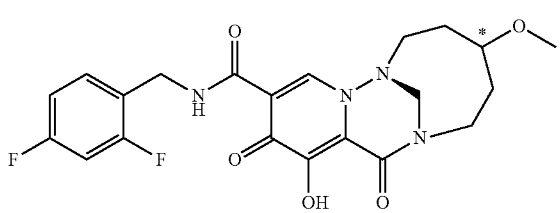 | Example 5 | 449 |
| 21A | 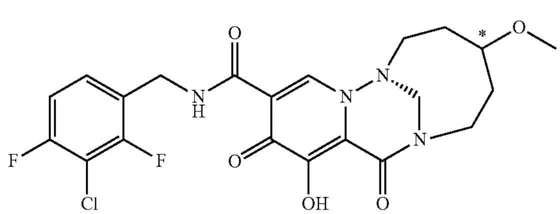 | Example 5 | 483 |

TABLE 1-continued

| Ex. No. | Structure | Preparative Method(s) Used | LRMS (ESI) [M + 1]+ |
|---|---|---|---|
| 21B | 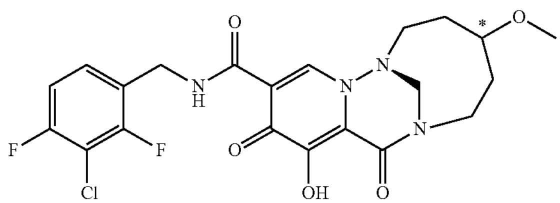 | Example 5 | 483 |
| 21C | 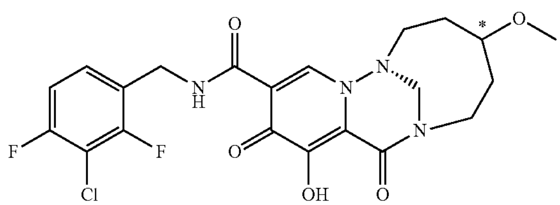 | Example 5 | 483 |
| 21D | 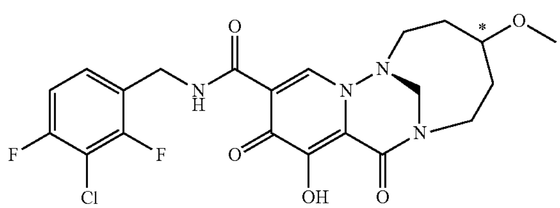 | Example 5 | 483 |
| 22A | 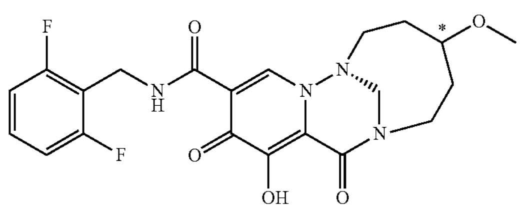 | Example 5 | 449 |
| 22B | 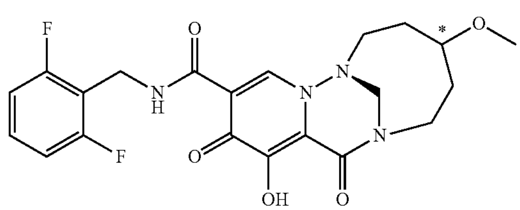 | Example 5 | 449 |
| 22C | 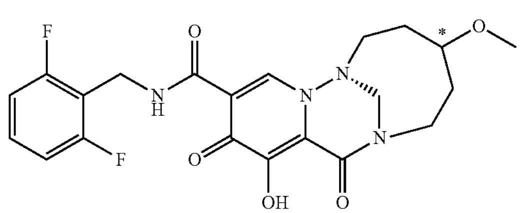 | Example 5 | 449 |
| 22D | 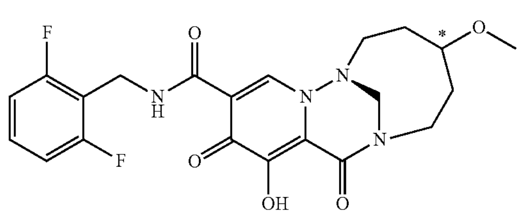 | Example 5 | 449 |

TABLE 1-continued

| Ex. No. | Structure | Preparative Method(s) Used | LRMS (ESI) [M + 1]+ |
|---|---|---|---|
| 23A | 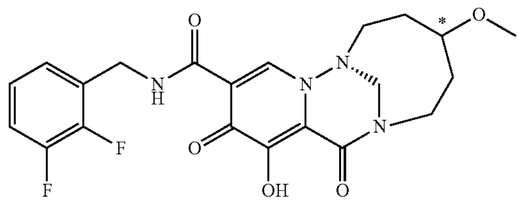 | Example 5 | 449 |
| 23B | 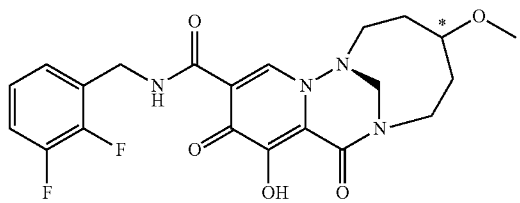 | Example 5 | 449 |
| 23C | 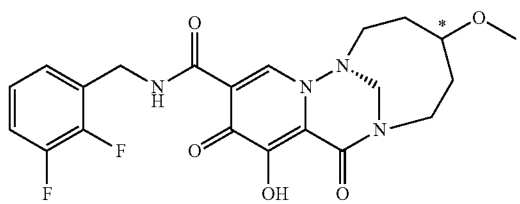 | Example 5 | 449 |
| 23D | 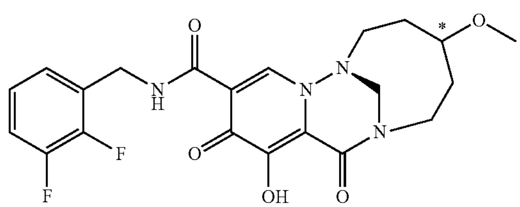 | Example 5 | 449 |
| 24A | 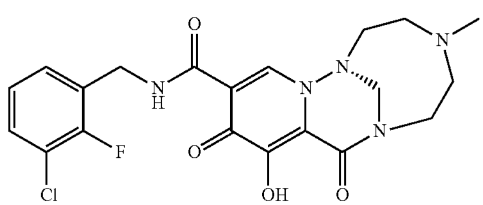 | Example 6 | 450 |
| 24B | 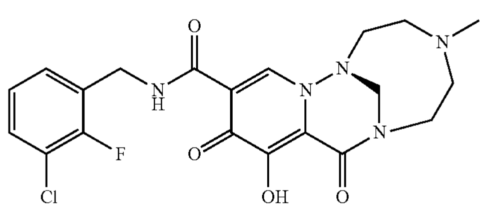 | Example 6 | 450 |
| 25A | 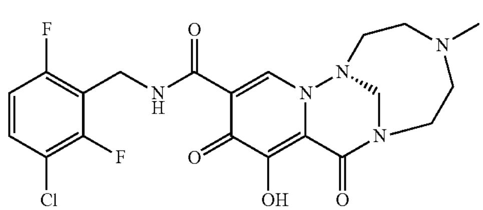 | Example 6 | 468 |

TABLE 1-continued

| Ex. No. | Structure | Preparative Method(s) Used | LRMS (ESI) [M + 1]+ |
|---|---|---|---|
| 25B | (structure) | Example 6 | 468 |
| 26A | (structure) | Example 7 | 455 |
| 26B | (structure) | Example 7 | 455 |

Assessing Antiviral Potency in a Multiple Round HIV-1 Infection Assay

The antiviral activity of the Examples herein was assessed in an assay that measures the rate of replication of HIV in cell culture, and performed according to the following procedure. HIV-1 replication was monitored using MT4-gag-GFP clone D3 (hereafter designated MT4-GFP), which are MT-4 cells modified to harbor a GFP reporter gene, the expression of which is dependent on the HIV-1 expressed proteins t at and rev. Productive infection of an MT4-GFP cell with HIV-1 results in GFP expression approximately 24 h post-infection. MT4-GFP cells were maintained at 37° C./5% $CO_2$/90% relative humidity in RPMI 1640 supplemented with 10% fetal bovine serum, 100 U/ml penicillin/streptomycin, and 400 μg/ml G418 to maintain the reporter gene. For infections, MT4-GFP cells were placed in the same medium lacking G418 and infected overnight with HIV-1 (H9/IIIB strain) virus at an approximate multiplicity of infection of 0.01 in the same incubation conditions. Cells were then washed and re-suspended in either RPMI 1640 at $2\times10^5$ cells/mL (0% NHS condition) or 100% normal human serum (NHS) at $2\times10^5$ cells/mL (100% NHS condition). Compound plates were prepared by dispensing compounds dissolved in DMSO into wells of 384 well poly-D-lysine-coated plates (0.2 μl/well) using an ECHO acoustic dispenser. Each compound was tested in a 10-point serial 3-fold dilution (typical final concentrations: 1050 nM-0.05 nM for 0% NHS condition or 42 μM-2.13 nM for 100% NHS condition). Controls included no inhibitor (DMSO only) and a combination of three antiviral agents (efavirenz, indinavir, an in-house integrase strand transfer inhibitor at final concentrations of 4 μM each). Cells were added (504/well) to compound plates and the infected cells were maintained at 37° C./5% $CO_2$/90% relative humidity.

Infected cells were quantified at two time points, ~48 h and ~72 h post-infection, by counting the number of green cells in each well using an Acumen eX3 scanner. The increase in the number of green cells over ~24 h period gives the reproductive ratio, RO, which is typically 5-15 and has been shown experimentally to be in logarithmic phase (data not shown). Inhibition of RO is calculated for each well, and $IC_{50}$s determined by non-linear 4-parameter curve fitting. Assay $IC_{50}$ results are shown in the table below.

| Example | Viking, $IC_{50}$ (0% NHS) (nM) | Viking, $IC_{50}$ (100% NHS) (nM) |
|---|---|---|
| 1A | 1.98 | 2559 |
| 1B | 1.00 | 94.7 |
| 2A | 4.04 | 4164 |
| 2B | 1.53 | 234.4 |
| 3A | 2.66 | 589 |
| 3B | 5.23 | 1885 |
| 4A | 3.45 | 9518 |
| 4B | 1.78 | 196.7 |
| 5A | 3.20 | 67.2 |
| 5B | 1.93 | 124 |
| 5C | 1.68 | 62.8 |
| 5D | 5.32 | 543.5 |
| 6A | 4.64 | 169.2 |
| 6B | 2.40 | 80.2 |
| 7A | 6.1 | 4462 |
| 7B | 2.16 | 73.9 |
| 8A | 1.03 | 1567 |
| 8B | 0.86 | 122.2 |
| 9A | 2.57 | 5621 |
| 9B | 1.15 | 196 |
| 10A | 1.89 | 8581 |
| 10B | 1.65 | 225 |
| 11A | 3.45 | 12510 |
| 11B | 2.09 | 357.8 |
| 12A | 14.28 | 10710 |
| 12B | 3.21 | 427.9 |

-continued

| Example | Viking, IC$_{50}$ (0% NHS) (nM) | Viking, IC$_{50}$ (100% NHS) (nM) |
|---|---|---|
| 13A | 2.74 | 3364 |
| 13B | 2.19 | 145.7 |
| 14A | 5.40 | 4213 |
| 14B | 1.66 | 156.6 |
| 15A | 3.70 | 10660 |
| 15B | 1.61 | 224.4 |
| 16A | 2.7 | 12280 |
| 16B | 1.2 | 247 |
| 17A | 66.1 | 1266 |
| 17B | 7.6 | 275 |
| 17C | 184.4 | 5919 |
| 17D | 25.6 | 717 |
| 18A | 3.1 | 279 |
| 18B | 2.5 | 435 |
| 18C | 3.2 | 1873 |
| 18D | 1.5 | 230 |
| 19A | 1.8 | 116 |
| 19B | 5.3 | 1875 |
| 19C | 3.5 | 245 |
| 19D | 1.5 | 300 |
| 20A | 3.3 | 88 |
| 20B | 2.8 | 371 |
| 20C | 7.5 | 606 |
| 20D | 2.1 | 212 |
| 21A | 2.5 | 2522 |
| 21B | 0.9 | 207 |
| 21C | 1.7 | 311 |
| 21D | 2.0 | 472 |
| 22A | 8.2 | 333 |
| 22B | 1.6 | 161 |
| 22C | 2.0 | 88 |
| 22D | 1.4 | 311 |
| 23A | 5.8 | 728 |
| 23B | 2.1 | 314 |
| 23C | 4.3 | 83 |
| 23D | 1.9 | 567 |
| 24A | 5.1 | 665 |
| 24B | 3.5 | 485 |
| 25A | 4.5 | 1001 |
| 25B | 2.1 | 139 |
| 26A | 6.6 | 869 |
| 26B | 3.2 | 91 |

Treatment or Prevention of HIV Infection

The Tricyclic Heterocycle Compounds may be useful in the inhibition of HIV, the inhibition of HIV integrase, the treatment of HIV infection and/or reduction of the likelihood or severity of symptoms of HIV infection and the inhibition of HIV viral replication and/or HIV viral production in a cell-based system. For example, the Tricyclic Heterocycle Compounds may be useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject, the methods comprising administering to the subject an effective amount of at least one Tricyclic Heterocycle Compound or a pharmaceutically acceptable salt or prodrug thereof. In a specific embodiment, the amount administered is effective to treat or prevent infection by HIV in the subject. In another specific embodiment, the amount administered is effective to inhibit HIV viral replication and/or viral production in the subject. In one embodiment, the HIV infection has progressed to AIDS.

The Tricyclic Heterocycle Compounds are also useful in the preparation and execution of screening assays for antiviral compounds. For example the Tricyclic Heterocycle Compounds may be useful for identifying resistant HIV cell lines harboring mutations, which are excellent screening tools for more powerful antiviral compounds. Furthermore, the Tricyclic Heterocycle Compounds may be useful in establishing or determining the binding site of other antivirals to the HIV Integrase.

The compositions and combinations of the present invention may be useful for treating a subject suffering from infection related to any HIV genotype.

Combination Therapy

In another embodiment, the present methods for treating or preventing HIV infection can further comprise the administration of one or more additional therapeutic agents which are not Tricyclic Heterocycle Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one Tricyclic Heterocycle Compound (which may include two or more different Tricyclic Heterocycle Compounds), or a pharmaceutically acceptable salt or prodrug thereof, and (ii) at least one additional therapeutic agent that is other than a Tricyclic Heterocycle Compound, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Tricyclic Heterocycle Compound and an additional therapeutic agent may be present in fixed amounts (dosage amounts) in a single dosage unit (e.g., a capsule, a tablet and the like).

In one embodiment, at least one Tricyclic Heterocycle Compound is administered during a time when the additional therapeutic agent(s) exert their prophylactic or therapeutic effect, or vice versa.

In another embodiment, at least one Tricyclic Heterocycle Compound and the additional therapeutic agent(s) are administered in doses commonly employed when such agents are used as monotherapy for treating a viral infection.

In another embodiment, at least one Tricyclic Heterocycle Compound and the additional therapeutic agent(s) are administered in doses lower than the doses commonly employed when such agents are used as monotherapy for treating a viral infection.

In still another embodiment, at least one Tricyclic Heterocycle Compound and the additional therapeutic agent(s) act synergistically and are administered in doses lower than the doses commonly employed when such agents are used as monotherapy for treating a viral infection.

In one embodiment, at least one Tricyclic Heterocycle Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that may be treated or prevented using the combination therapy methods of the present invention include, but are not limited to, those listed above.

In one embodiment, the viral infection is HIV infection.

In another embodiment, the viral infection is AIDS.

The at least one Tricyclic Heterocycle Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Tricyclic Heterocycle Compound and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| dolutegravir, Tivicay ® | II |
| doravirine, Delstrigo ™ | nnRTI |
| doravirine + lamivudine + tenofovir disoproxil fumarate, Pifeltro ™ | nnRTI + nRTI + nRTI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |

TABLE A-continued

| Name | Type |
|---|---|
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| rilpivirine, TMC-278 | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor; FI = fusion inhibitor; PI = protease inhibitor; nRTI = nucleoside reverse transcriptase inhibitor; II = integrase inhibitor; nnRTI = non-nucleoside reverse transcriptase inhibitor. Some of the drugs listed in the table are used in a salt form; e.g., abacavir sulfate, indinavir sulfate, atazanavir sulfate, nelfinavir mesylate.

In one embodiment, one or more anti-HIV drugs are selected from, lamivudine, abacavir, ritonavir, darunavir, atazanavir, emtricitabine, tenofovir, rilpivirine and lopinavir.

In another embodiment, the compound of formula (I) is used in combination with lamivudine.

In still another embodiment, the compound of formula (I) is used in combination atazanavir.

In another embodiment, the compound of formula (I) is used in combination with darunavir.

In another embodiment, the compound of formula (I) is used in combination with rilpivirine.

In one embodiment, the compound of formula (I) is used in combination with lamivudine and abacavir.

In another embodiment, the compound of formula (I) is used in combination with darunavir.

In another embodiment, the compound of formula (I) is used in combination with emtricitabine and tenofovir.

In still another embodiment, the compound of formula (I) is used in combination atazanavir.

In another embodiment, the compound of formula (I) is used in combination with ritonavir and lopinavir.

In one embodiment, the compound of formula (I) is used in combination with abacavir and lamivudine.

In another embodiment, the compound of formula (I) is used in combination with lopinavir and ritonavir.

In one embodiment, the present invention provides pharmaceutical compositions comprising (i) a compound of formula (I) or a pharmaceutically acceptable salt or prodrug thereof; (ii) a pharmaceutically acceptable carrier; and (iii) one or more additional anti-HIV agents selected from lamivudine, abacavir, ritonavir and lopinavir, or a pharmaceutically acceptable salt or prodrug thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt or prodrug thereof and (ii) one or more additional anti-HIV agents selected from lamivudine, abacavir, ritonavir and lopinavir, or a pharmaceutically acceptable salt or prodrug thereof, wherein the amounts administered of components (i) and (ii)

are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, $57^{th}$ edition (2003), the $58^{th}$ edition (2004), the $59^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection may be determined by the attending clinician, taking into consideration the approved doses and dosage regimen in the package insert; the age, sex and general health of the subject; and the type and severity of the viral infection or related disease or disorder. When administered in combination, the Tricyclic Heterocycle Compound(s) and the other agent(s) may be administered simultaneously (i.e., in the same composition or in separate compositions one right after the other) or sequentially. This is particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Tricyclic Heterocycle Compounds may be administered as a component of a composition that comprises a pharmaceutically acceptable carrier or vehicle. The present invention provides pharmaceutical compositions comprising an effective amount of at least one Tricyclic Heterocycle Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules may be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Tricyclic Heterocycle Compounds are administered orally.

In another embodiment, the one or more Tricyclic Heterocycle Compounds are administered intravenously.

In one embodiment, a pharmaceutical preparation comprising at least one

Tricyclic Heterocycle Compound is in unit dosage form. In such form, the preparation is subdivided into unit doses containing effective amounts of the active components.

Compositions may be prepared according to conventional mixing, granulating or coating methods, respectively, and the present compositions can contain, in one embodiment, from about 0.1% to about 99% of the Tricyclic Heterocycle Compound(s) by weight or volume. In various embodiments, the present compositions can contain, in one embodiment, from about 1% to about 70% or from about 5% to about 60% of the Tricyclic Heterocycle Compound(s) by weight or volume.

The compounds of Formula I may be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions may be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The unit dosages of the Tricyclic Heterocycle Compounds may be administered at varying frequencies. In one embodiment, a unit dosage of a Tricyclic Heterocycle Compound may be administered once daily. In another embodiment, a unit dosage of a Tricyclic Heterocycle Compound may be administered twice weekly. In another embodiment, a unit dosage of a Tricyclic Heterocycle Compound may be administered once weekly. In still another embodiment, a unit dosage of a Tricyclic Heterocycle Compound may be administered once biweekly. In another embodiment, a unit dosage of a Tricyclic Heterocycle Compound may be administered once monthly. In yet another embodiment, a unit dosage of a Tricyclic Heterocycle Compound may be administered once bimonthly. In another embodiment, a unit dosage of a Tricyclic Heterocycle Compound may be administered once every 3 months. In a further embodiment, a unit dosage of a Tricyclic Heterocycle Compound may be administered once every 6 months. In another embodiment, a unit dosage of a Tricyclic Heterocycle Compound may be administered once yearly.

The amount and frequency of administration of the Tricyclic Heterocycle Compounds will be regulated according to the judgment of the attending clinician considering such factors as age, condition and size of the subject as well as severity of the symptoms being treated. The compositions of the invention can further comprise one or more additional therapeutic agents, selected from those listed above herein.

Kits

In one aspect, the present invention provides a kit comprising a therapeutically effective amount of at least one Tricyclic Heterocycle Compound, or a pharmaceutically acceptable salt or prodrug of said compound and a pharmaceutically acceptable carrier, vehicle or diluent.

In another aspect the present invention provides a kit comprising an amount of at least one Tricyclic Heterocycle Compound, or a pharmaceutically acceptable salt or prodrug of said compound and an amount of at least one additional therapeutic agent listed above, wherein the amounts of the two or more active ingredients result in a desired therapeutic effect. In one embodiment, the one or more Tricyclic Heterocycle Compounds and the one or more additional therapeutic agents are provided in the same container. In one embodiment, the one or more Tricyclic Heterocycle Compounds and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound of the formula:

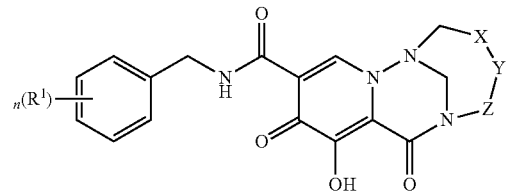

or a pharmaceutically acceptable salt thereof, wherein:

X is —$CR^2R^3$, —O— or —$NR^4$;

Y is —$CHR^4$—$CR^2R^3$, —$CR^2R^3$, —O— or —$NR^4$;

Z is —$CR^2R^3$—$CHR^4$, —$CR^2R^3$;

each occurrence of $R^1$ is independently selected from the group consisting of halo, hydroxyl, $C_1$-6 alkyl and —O—($C_1$-C6 alkyl);

each occurrence of $R^2$ is independently selected from the group consisting of hydrogen, halo, hydroxyl, $C_1$-6 alkyl and —O—($C_1$-C6 alkyl);

each occurrence of $R^3$ is independently selected from the group consisting of hydrogen, halo, hydroxyl, $C_1$-6 alkyl and —O—($C_1$-C6 alkyl);

each occurrence of $R^4$ is independently selected from the group consisting of hydrogen or $C_1$-6 alkyl;

n is an integer between zero and three.

2. The compound of claim 1 wherein X is —$CR^2R^3$, or a pharmaceutically acceptable salt thereof.

3. The compound of claim 1 wherein Y is —$CHR^4$—$CR^2R^3$, or a pharmaceutically acceptable salt thereof.

4. The compound of claim 1 wherein Y is —$CR^2R^3$, or a pharmaceutically acceptable salt thereof.

5. The compound of claim 1 wherein Y is —O—, or a pharmaceutically acceptable salt thereof.

6. The compound of claim 1 wherein Y is —$NR^4$, or a pharmaceutically acceptable salt thereof.

7. The compound of claim 1 wherein Z is —$CR^2R^3$—$CHR^4$, or a pharmaceutically acceptable salt thereof.

8. The compound of claim 1 wherein Z is —$CR^2R^3$, or a pharmaceutically acceptable salt thereof.

9. The compound of claim 1 wherein each occurrence of $R^2$ is independently selected from the group consisting of hydrogen, hydroxyl, and —$OCH_3$, or a pharmaceutically acceptable salt thereof.

10. The compound of claim 1 wherein $R^4$ is hydrogen or methyl, or a pharmaceutically acceptable salt thereof.

11. The compound of claim 1 wherein n is two or three, or a pharmaceutically acceptable salt thereof.

12. The compound of claim 1 selected from:

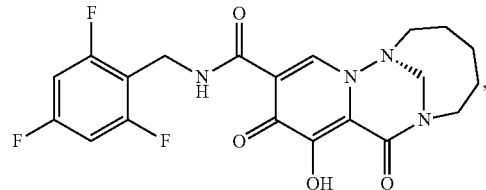

-continued
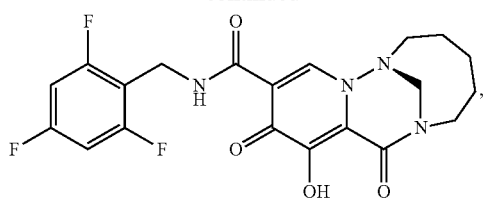
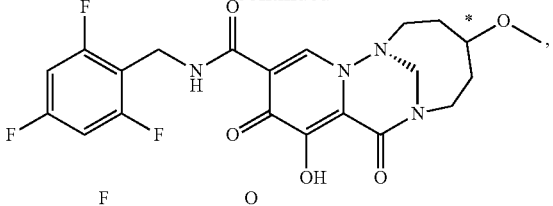
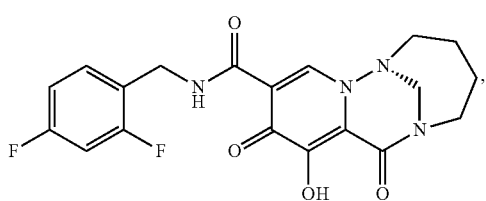
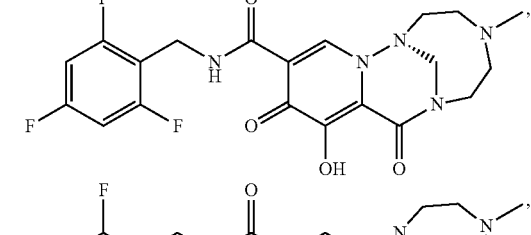
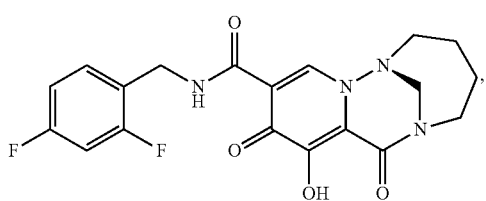
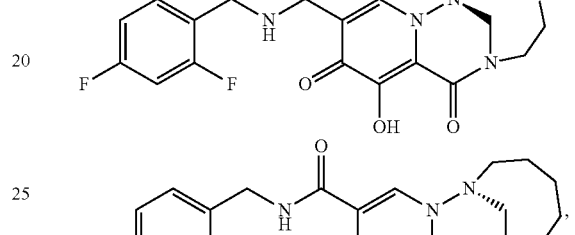
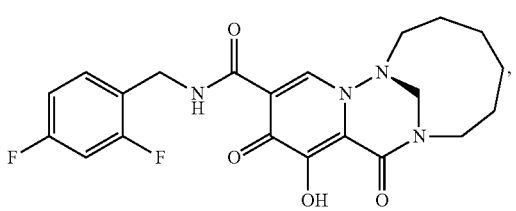
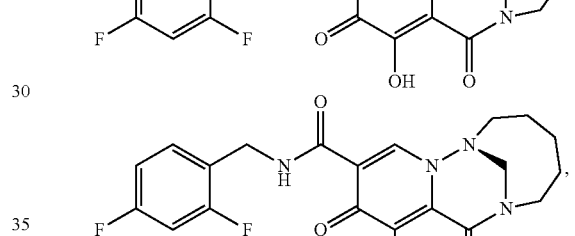
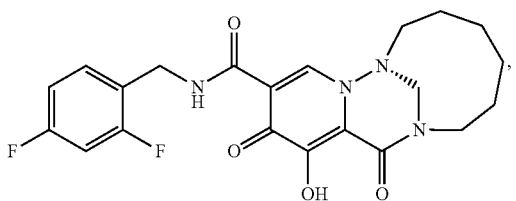
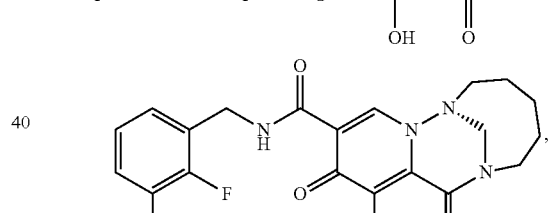
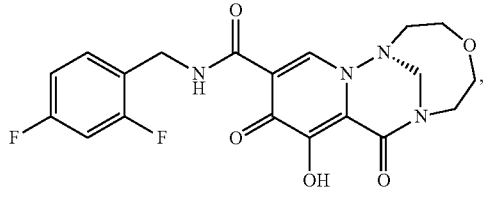
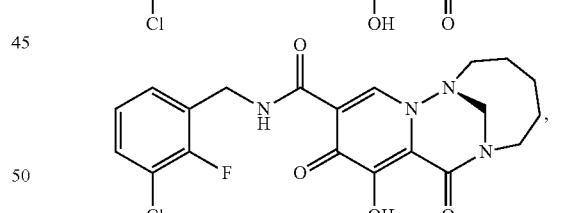
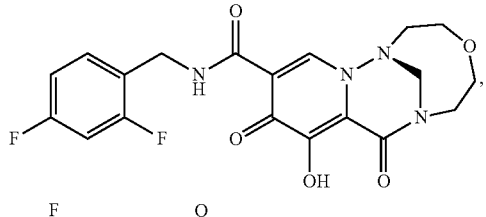
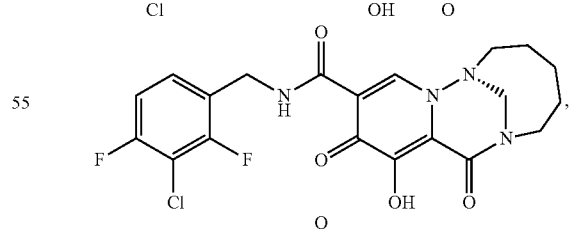
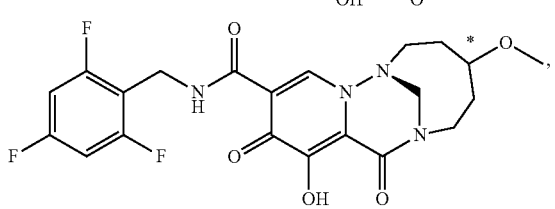

-continued
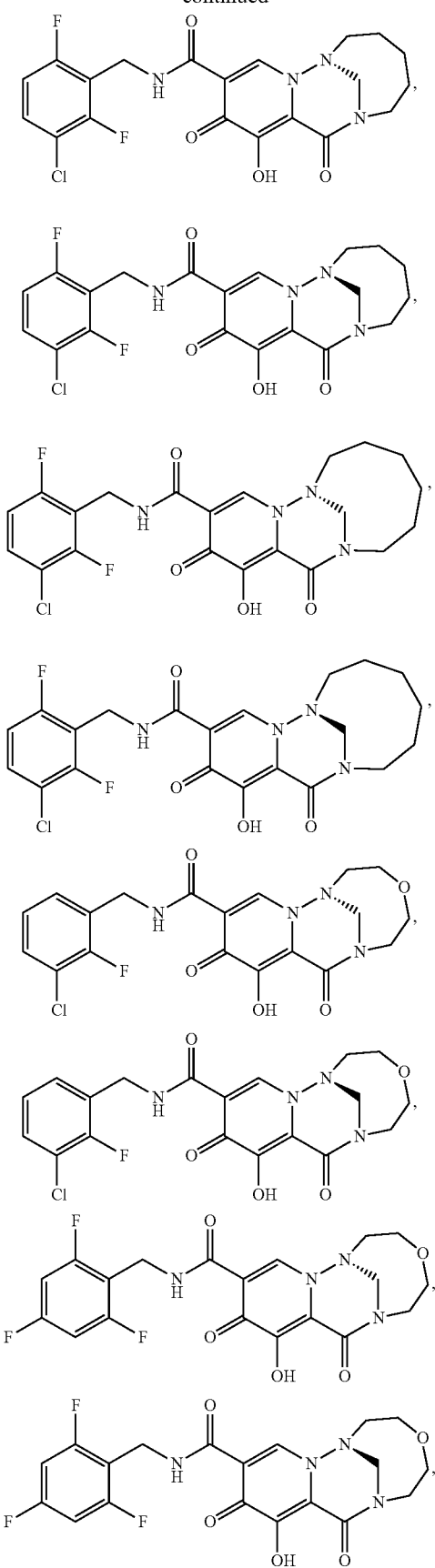
-continued
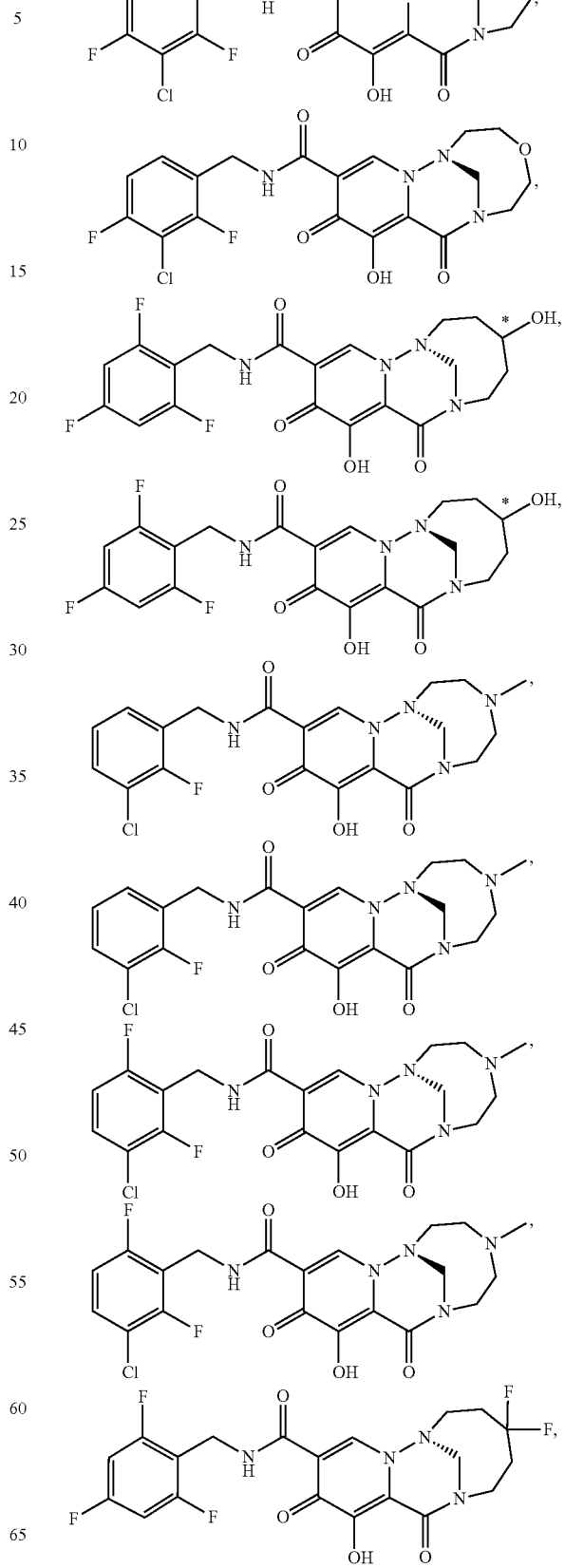

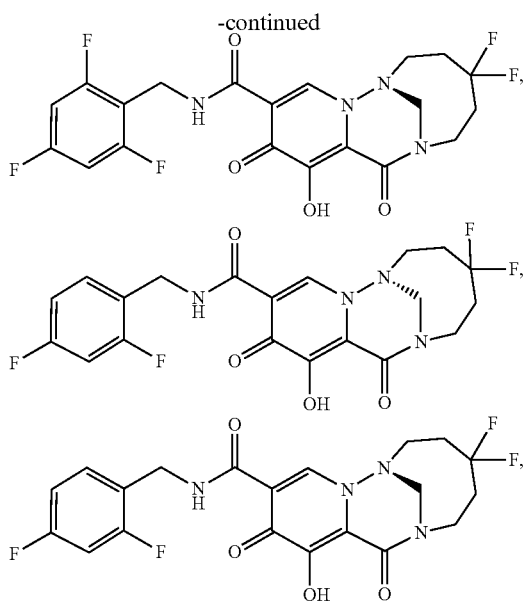

or a pharmaceutically acceptable salt thereof.

13. A pharmaceutical composition comprising an effective amount of a compound according to claim 1, or a pharmaceutically acceptable salt thereof, and a pharmaceutically acceptable carrier.

14. A method for the inhibition of HIV integrase in a subject in need thereof which comprises administering to the subject an effective amount of the compound according to claim 1, or a pharmaceutically acceptable salt thereof.

15. A method for the treatment of infection by HIV or for the treatment of AIDS in a subject in need thereof, which comprises administering to the subject an effective amount of the compound according to of claim 1, or a pharmaceutically acceptable salt thereof.

16. The pharmaceutical composition of claim 13, further comprising one or more additional therapeutic agents selected from, raltegravir, lamivudine, abacavir, ritonavir, dolutegravir, arunavir, atazanavir, emtricitabine, tenofovir, elvitegravir, rilpivirine and lopinavir.

17. The method of claim 15, further comprising administering to the subject one or more additional therapeutic agents selected from raltegravir, lamivudine, abacavir, ritonavir, dolutegravir, arunavir, atazanavir, emtricitabine, tenofovir, elvitegravir, rilpivirine and lopinavir, wherein the amounts administered of the compound of claim 1 and the one or more additional therapeutic agents, are together effective to treat infection by HIV or to treat, prevent or delay the onset or progression of AIDS.

18. A compound according to claim 1, or a pharmaceutically acceptable salt thereof, for use in the preparation of a medicament for the inhibition of HIV integrase, for the treatment or prophylaxis of infection by HIV, or for the treatment, prophylaxis, or delay in the onset or progression of AIDS in a subject in need thereof.

* * * * *